(12) United States Patent
Collin et al.

(10) Patent No.: US 11,279,933 B2
(45) Date of Patent: *Mar. 22, 2022

(54) ANTISENSE OLIGONUCLEOTIDES FOR THE TREATMENT OF LEBER CONGENITAL AMAUROSIS

(71) Applicant: Stichting Radboud universitair medisch centrum, Nijmegen (NL)

(72) Inventors: Robert Wilhelmus Johanna Collin, Venlo (NL); Franciscus Peter Maria Cremers, Malden (NL); Antonia Ingrid Den Hollander, Groesbeek (NL)

(73) Assignee: Stichting Radboud universitair medisch centrum, Nijmegen (NL)

(*) Notice: Subject to any disclaimer, the term of this patent is extended or adjusted under 35 U.S.C. 154(b) by 10 days.

This patent is subject to a terminal disclaimer.

(21) Appl. No.: 16/842,157

(22) Filed: Apr. 7, 2020

(65) Prior Publication Data

US 2020/0255832 A1  Aug. 13, 2020

Related U.S. Application Data

(63) Continuation of application No. 16/197,865, filed on Nov. 21, 2018, now Pat. No. 10,647,985, which is a continuation of application No. 15/963,229, filed on Apr. 26, 2018, now Pat. No. 10,167,470, which is a continuation of application No. 15/656,635, filed on Jul. 21, 2017, now abandoned, which is a continuation of application No. 14/342,776, filed as application No. PCT/NL2012/050275 on Apr. 25, 2012, now Pat. No. 9,771,580.

(60) Provisional application No. 61/531,137, filed on Sep. 6, 2011.

(30) Foreign Application Priority Data

Sep. 5, 2011 (NL) .................................... 2007351

(51) Int. Cl.
*C12N 15/113* (2010.01)

(52) U.S. Cl.
CPC ........ *C12N 15/113* (2013.01); *C12N 2310/11* (2013.01); *C12N 2310/15* (2013.01); *C12N 2310/321* (2013.01); *C12N 2310/346* (2013.01); *C12N 2320/33* (2013.01); *C12N 2320/34* (2013.01)

(58) Field of Classification Search
None
See application file for complete search history.

(56) References Cited

U.S. PATENT DOCUMENTS

| | | | |
|---|---|---|---|
| 6,875,736 B2 | 4/2005 | Rana | |
| 7,517,644 B1 | 4/2009 | Smith | |
| 9,487,782 B2 | 11/2016 | Rozet et al. | |
| 9,771,580 B2 * | 9/2017 | Collin | A61P 27/02 |
| 10,167,470 B2 * | 1/2019 | Collin | C12N 15/113 |
| 10,647,985 B2 | 5/2020 | Collin et al. | |
| 2005/0118625 A1 | 6/2005 | Mounts | |
| 2005/0233455 A1 | 10/2005 | Damha et al. | |
| 2009/0011040 A1 * | 1/2009 | Naash | A61K 9/5146 424/501 |
| 2009/0269755 A1 | 10/2009 | Aartsma-Rus et al. | |
| 2011/0117058 A1 | 5/2011 | Auricchio | |
| 2012/0108654 A1 | 5/2012 | Campochiaro | |

FOREIGN PATENT DOCUMENTS

| | | |
|---|---|---|
| EP | 1619249 | 1/2006 |
| WO | WO 2002024906 | 3/2002 |
| WO | WO 2009121536 | 10/2009 |
| WO | WO 2012168435 | 12/2012 |

OTHER PUBLICATIONS

Aartsma-Rus, et al., "Exonic sequences provide better targets for antisense oligonucleotides than splice site sequences in the modulation of Duchenne muscular dystrophy splicing," Oligonucleotides, 2008, 20:69-77.
Aartsma-Rus, et al., "Guidelines for antisense oligonucleotide design and insight into splice-modulating mechanisms," Mol. Ther., 2008, 548-553.
Alloca, et al., "Novel adeno-associated virus serotypes efficiently transduce murine photoreceptors," J. Virol., 2007, 81:11372-11380.
Baala et al., "Pleiotropic effects of CEP290 (NPHP6) mutations extend to Meckel syndrome", Am. J. Hum. Genet., 2007, 81:170-179.
Bainbridge, et al. "Effect of gene therapy on visual function in Leber's congenital amaurosis," N. Engl. J. Med., 2008, 358:2231-2239.
Baye, "The N-Terminal Region of Centrosomal Protein 290 (CEP290) Restores Vision in a Zebrafish Model of Human Blindness", Human Molecular Genetics, Apr. 2011, vol. 20, No. 8, pp. 1467-1477.
Cideciyan et al., "Centrosomai-Ciliary Gene CEP290/NPHP6 Mutations Result in Blindness with Unexpected Sparing of Photoreceptors and Visual Brain: Implications for Therapy of Leber Congenital Amaurosis", Human Mutation, Nov. 2007, vol. 28, No. 11, pp. 1074-1083.
Cideciyan, et al. "Human gene therapy for RPE65 isomerase deficiency activates the retinoid cycle of vision but with slow rod kinetics", Proc Natl Acad Sci, 2008, vol. 105, 15112-15117.
Collin et al., "Antisense oligonucleotide (AON)-based therapy for CEP290-associated LCA." Poster presented at: ARVO Annual Meeting, May 3, 2011, Program No. 3324, Poster No. A572.
Coppieters, et al. "Genetic screening of LCA in Belgium: predominance of CEP290 and identification of potential modifier alleles in AH 11 of CEP290-related phenotypes", Hum Mutat, 2010, 31:E1709-E1766.

(Continued)

Primary Examiner — Brian Whiteman
(74) *Attorney, Agent, or Firm* — Fish & Richardson P.C.

(57) ABSTRACT

The present invention relates to the fields of medicine and immunology. In particular, it relates to novel antisense oligonucleotides that may be used in the treatment, prevention and/or delay of Leber congenital amaurosis.

13 Claims, 5 Drawing Sheets

Specification includes a Sequence Listing.

(56) References Cited

OTHER PUBLICATIONS

Coppieters, et al., "CEP290, a gene with many faces: mutation overview and presentation of CEP290base," Hum. Mutat., 2010, 31:1097-1108.
Dorn and Kippenberger, "Clinical application of CpG-, non-CpG-, and antisense oligodeoxynucleotides as immunomodulators," Curr. Opin. Mol. Ther., 2008, 10(1):10-20.
Egholm, et al., "PNA hybridizes to comlementary oligonucleotides obeying the Watson-Crick hydrogen-bonding rules," Nature, 1993, 365:566-568.
Estrada-Cuzcano, et al. "IQCB1 mutations in patients with leber congenital amaurosis", Invest Ophthalmol Vis Sci, 2011, vol. 52, 834-839.
Franchi et al., "Identification of 4370 expressed sequence tags from a 3'-end-specific cDNA library of human skeletal muscle by DNA sequencing and filter hybridization", Genome Research, 1996, vol. 6.1, pp. 35-42.
Frank, et al., "Mutations of the CEP290 gene encoding a centrosomal protein cause Meckel-Gruber syndrome," Hum. Mutat., 2008, 29:45-52.
Friesen and Darby, "Specific RNA binding proteins constructed from zinc fingers," Nature Structural Biology, 1998, 5:543-546.
Geib and Hertel, "Restoration of full-length SMN promoted by adenoviral vectors expressiong RNA antisense oligonucleotides embedded in U7 snRNAs," PLoS One, 2009, e8204.
Gerard et al., "Antisense Oligonucleotide-Mediated Exon Skipping Restores Primary Cilia Assembly in Fibroblasts Harbouring the Common LCA CEP290 C.2991+1655g>A Mutation", Investigative Ophthalmology & Visual Science, Mar. 2012, 1920-1920.
Gerard et al., "AON-Mediated Exon Skipping Restores Ciliation in Fibroblasts Harboring the Common Leber Congenital Amaurosis CEP290 Mutation", American Society of Gene & Cell Therapy, Molecular Therapy-Nucleic Acids, Jun. 26, 2012, vol. 1, e29.
Gorman, et al., "Stable alteration of pre-mRNA splicing patterns by modified U7 small nuclear RNAs," Proc. Natl. Acad. Sci. USA, 1998, 95(9):4929-34.
Govindaraju and Kumar, "Backbone-extended pyrrolidine peptide nucleic acids (bepPNA): design, synthesis and DNA/RNA binding studies," Chem. Commun., 2005, 495-497.
Goyenvalle, et al., "Rescue of dystrophic muscle through U7 snRNA-mediated exon skipping," Science, 2004, 306:1796-1799.
Hammond, et al., "Genetic therapies for RNA mis-splicing diseases," Trends Genet., 2011, 27:196-205.
Hauswirth, et al. "Phase I Trial of Leber Congenital Amaurosis due to Estrada-Mutations by OcularSubretina Injection of Adena-Associated Virus Gene Vector: Short-Term Results," Hum Gene Ther, Oct. 2008, vol. 19, pp. 979-990.
Helou, et al. "Mutation analysis of NPHP6/CEP290 in patients with Joubert syndrome and Senior-Loken syndrome", U Med Genet. 2007, 44:657-663.
Hollander et al., "Mutations in the CEP290 (NPHP6) Gene are a Frequent Cause of Leber Congenital amaurosis," American Journal of Human Genetics, American Society of Human Genetics, Sep. 2006, vol. 79, No. 3, pp. 556-561.
Hollander, et al. "Leber congenital amaurosis: genes, proteins and disease mechanisms," Prog Retin Eye Res, 2008, vol. 27:391-419.
Hollander, et al. "Lighting a candle in the dark: advances in genetics and gene therapy of recessive retinal dystrophies", J Clin Invest, 2010, vol. 120, 3042-3053.
International Search Report in PCT/NL2012/050275 dated Aug. 28, 2012.
Jahns, et al., "Stereochemical bias introduced during RNA synthesis modulates the activity of phosphorothioate siRNAs," Nature Communications, 2015, 6:6317.
Kinali, et al., "Local restoration of dystrophin expression with the morpholino oligomer AVI-4658 in Duchenne muscular dystrophy: a single-clind, placebo-controlled, dose-escalation, proof-of-concept study," Lancet Neurol., 2009, 8:918-928.
Koenekoop, et al. "Genetic testing for retinal dystrophies and dysfunctions: benefits, dilemmas and solutions", Clin Experiment Ophthalmol, 2007, vol. 35, 473-485.
Lebherz, et al., "Novel AAV serotypes for improved ocular gene transfer," J. Gene Med., 2008, 10:375-382.
Li, et al., "Gene therapy following subretinal AAV5 vector delivery is not affected by a previous intravitreal AAV5 vector administration in the partner eye," Mol. Vis., 2009, 15:267-275.
Littink, et al. "A novel nonsense mutation in CEP290 induces exon skipping and leads to a relatively mild retinal Phenotype", Invest Ophthalmol Vis Sci, 2010, Vo. 51, 3646-3652.
Maguire, et al. "Age-dependent effects of RPE65 gene therapy for Leber's congenital amaurosis: a phase 1 doseescalation trial", Lancet, 2009, vol. 374, 1597-1605.
Maguire, et al. "Safety and efficacy of gene transfer for Leber's congenital amaurosis," N Engl J Med, 2008, vol. 358, 2240-2248.
Morita, et al., "2'-O, 4'C-Ethylene-bridged nucleic acids (ENA) with nuclease-resistance and high affinity for RNA," Nucleic Acid Res., 2001, Suppl. 1: 241-242.
Nielsen, et al., "Sequence-selective recognition of DNA by strand displacement with a thymine-substituted polyamide," Science, 1991, 254:1497-1500.
Perrault, et al. "Spectrum of NPHP6/CEP290 mutations in Leber congenital amaurosis and delineation of the associated phenotype", Hum Mutat, 2007, vol. 28:416-416.
Schmid and Jelinek, "The Alu family of dispersed repetitive sequences," Science, 1982, 216:1065-1070.
Simonelli, et al., "Gene therapy for Leber's congenital amaurosis is safe and effective through 1.5 years after vetor administration," Mol. Ther., 2009, 18:643-650.
Smith, et al., "An increased specificity score matrix for the prediction of SF2/ASF-specific exonic splicing enhancers," Hum. Mol. Genet., 2006, 15:2490-2508.
Stone "Leber congenital amaurosis—a model for efficient genetic testing of heterogeneous disorders: LXIV Edward Jackson Memorial Lecture", Am J Ophthalmol, 2007, vol. 144, 791-811.
Suter, et al., Double-target antisense U7 snRNAs promote efficient skipping of an aberrant exon in three human beta-thalassemic mutations, hum. Mol. Genet., 1999, 8(13):2415-23.
Valente, et al. "Mutations in CEP290, which encodes a centrosomal protein, cause pleiotropic forms of Joubert syndrome", Nat Genet, 2006, vol. 38, 623-625.
Van Deutekom, et al., "Local dystrophin restoration with antisense oligonucleotide PRO051," N. Engl. J. Med., 2007, N. Engl. J. Med., 357:2677-2686.
Vandenberghe, et al., "Dosage thresholds for AAV2 and AAV8 photoreceptor gene therapy in monkey," Sci. Transl. Med., 2011, 3:88ra54.

* cited by examiner

A Wild-type *CEP290*

B LCA mutant *CEP290*

C LCA mutant *CEP290* + AON

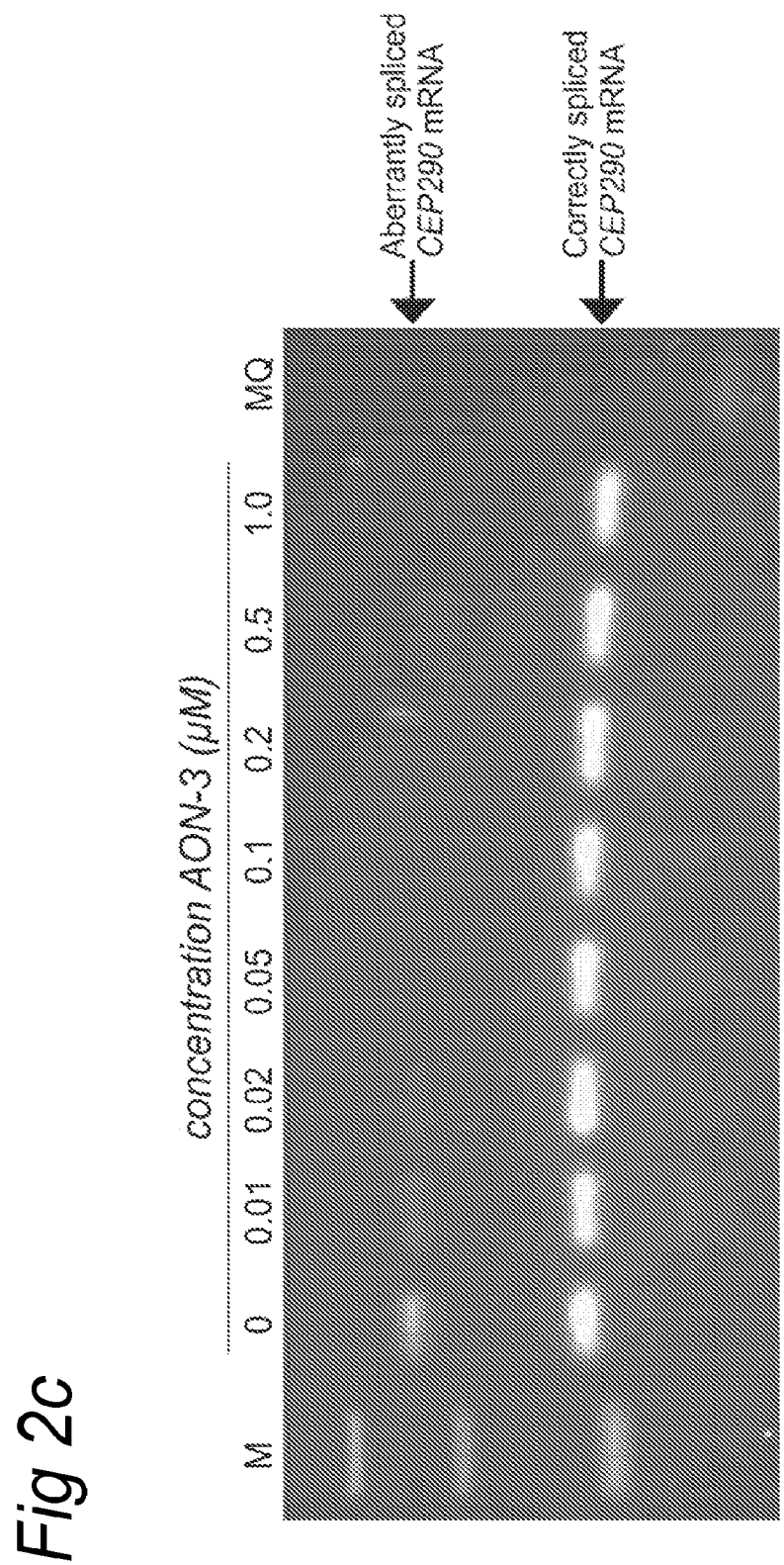

SEQUENCE LISTING

```
<160> NUMBER OF SEQ ID NOS: 21

<210> SEQ ID NO 1
<211> LENGTH: 93203
<212> TYPE: DNA
<213> ORGANISM: Homo sapiens
<220> FEATURE:
<221> NAME/KEY: 5'UTR
<222> LOCATION: (1)..(909)
<223> OTHER INFORMATION: Intron from 318 to 882
<220> FEATURE:
<221> NAME/KEY: exon
<222> LOCATION: (910)..(1011)
<220> FEATURE:
<221> NAME/KEY: Intron
<222> LOCATION: (1012)..(1183)
<220> FEATURE:
<221> NAME/KEY: exon
<222> LOCATION: (1184)..(1261)
<220> FEATURE:
<221> NAME/KEY: Intron
<222> LOCATION: (1262)..(2652)
<220> FEATURE:
<221> NAME/KEY: exon
<222> LOCATION: (2653)..(2722)
<220> FEATURE:
<221> NAME/KEY: Intron
<222> LOCATION: (2723)..(3025)
<220> FEATURE:
<221> NAME/KEY: exon
```

-continued

```
<222> LOCATION: (3026)..(3072)
<220> FEATURE:
<221> NAME/KEY: Intron
<222> LOCATION: (3073)..(5430)
<220> FEATURE:
<221> NAME/KEY: exon
<222> LOCATION: (5431)..(5574)
<220> FEATURE:
<221> NAME/KEY: Intron
<222> LOCATION: (5575)..(10998)
<220> FEATURE:
<221> NAME/KEY: exon
<222> LOCATION: (10999)..(11052)
<220> FEATURE:
<221> NAME/KEY: Intron
<222> LOCATION: (11053)..(11651)
<220> FEATURE:
<221> NAME/KEY: exon
<222> LOCATION: (11652)..(11672)
<220> FEATURE:
<221> NAME/KEY: Intron
<222> LOCATION: (11673)..(11796)
<220> FEATURE:
<221> NAME/KEY: exon
<222> LOCATION: (11797)..(11949)
<220> FEATURE:
<221> NAME/KEY: Intron
<222> LOCATION: (11950)..(12340)
<220> FEATURE:
<221> NAME/KEY: exon
<222> LOCATION: (12341)..(12523)
<220> FEATURE:
<221> NAME/KEY: Intron
<222> LOCATION: (12524)..(13181)
<220> FEATURE:
<221> NAME/KEY: exon
<222> LOCATION: (13182)..(13271)
<220> FEATURE:
<221> NAME/KEY: Intron
<222> LOCATION: (13272)..(15778)
<220> FEATURE:
<221> NAME/KEY: exon
<222> LOCATION: (15779)..(15901)
<220> FEATURE:
<221> NAME/KEY: Intron
<222> LOCATION: (15902)..(16847)
<220> FEATURE:
<221> NAME/KEY: exon
<222> LOCATION: (16848)..(16971)
<220> FEATURE:
<221> NAME/KEY: Intron
<222> LOCATION: (16972)..(21050)
<220> FEATURE:
<221> NAME/KEY: exon
<222> LOCATION: (21051)..(21220)
<220> FEATURE:
<221> NAME/KEY: Intron
<222> LOCATION: (21221)..(21940)
<220> FEATURE:
<221> NAME/KEY: exon
<222> LOCATION: (21941)..(22103)
<220> FEATURE:
<221> NAME/KEY: Intron
<222> LOCATION: (22104)..(23473)
<220> FEATURE:
<221> NAME/KEY: exon
<222> LOCATION: (23474)..(23574)
<220> FEATURE:
<221> NAME/KEY: Intron
<222> LOCATION: (23575)..(23646)
<220> FEATURE:
<221> NAME/KEY: exon
<222> LOCATION: (23647)..(23734)
<220> FEATURE:
<221> NAME/KEY: Intron
<222> LOCATION: (23735)..(25071)
<220> FEATURE:
<221> NAME/KEY: exon
<222> LOCATION: (25072)..(25184)
```

```
<220> FEATURE:
<221> NAME/KEY: Intron
<222> LOCATION: (25185)..(27034)
<220> FEATURE:
<221> NAME/KEY: exon
<222> LOCATION: (27035)..(27119)
<220> FEATURE:
<221> NAME/KEY: Intron
<222> LOCATION: (27120)..(27654)
<220> FEATURE:
<221> NAME/KEY: exon
<222> LOCATION: (27655)..(27797)
<220> FEATURE:
<221> NAME/KEY: Intron
<222> LOCATION: (27798)..(30358)
<220> FEATURE:
<221> NAME/KEY: exon
<222> LOCATION: (30359)..(30523)
<220> FEATURE:
<221> NAME/KEY: Intron
<222> LOCATION: (30524)..(30865)
<220> FEATURE:
<221> NAME/KEY: exon
<222> LOCATION: (30866)..(31015)
<220> FEATURE:
<221> NAME/KEY: Intron
<222> LOCATION: (31016)..(33035)
<220> FEATURE:
<221> NAME/KEY: exon
<222> LOCATION: (33036)..(33151)
<220> FEATURE:
<221> NAME/KEY: Intron
<222> LOCATION: (33152)..(35118)
<220> FEATURE:
<221> NAME/KEY: exon
<222> LOCATION: (35119)..(35221)
<220> FEATURE:
<221> NAME/KEY: Intron
<222> LOCATION: (35222)..(35311)
<220> FEATURE:
<221> NAME/KEY: exon
<222> LOCATION: (35312)..(35542)
<220> FEATURE:
<221> NAME/KEY: Intron
<222> LOCATION: (35543)..(39205)
<220> FEATURE:
<221> NAME/KEY: exon
<222> LOCATION: (39206)..(39379)
<220> FEATURE:
<221> NAME/KEY: Intron
<222> LOCATION: (39380)..(45217)
<223> OTHER INFORMATION: Aberrant exon included in mutant CEP290 mRNA
      position 40902-41209 mutated nucleotide A>G in LCA patients at
      position 41034
<220> FEATURE:
<221> NAME/KEY: exon
<222> LOCATION: (45218)..(45329)
<220> FEATURE:
<221> NAME/KEY: Intron
<222> LOCATION: (45330)..(48241)
<220> FEATURE:
<221> NAME/KEY: exon
<222> LOCATION: (48242)..(48447)
<220> FEATURE:
<221> NAME/KEY: Intron
<222> LOCATION: (48448)..(49384)
<220> FEATURE:
<221> NAME/KEY: exon
<222> LOCATION: (49385)..(49536)
<220> FEATURE:
<221> NAME/KEY: Intron
<222> LOCATION: (49537)..(51377)
<220> FEATURE:
<221> NAME/KEY: exon
<222> LOCATION: (51378)..(51489)
<220> FEATURE:
<221> NAME/KEY: Intron
<222> LOCATION: (51490)..(52729)
<220> FEATURE:
```

```
<221> NAME/KEY: exon
<222> LOCATION: (52730)..(53185)
<220> FEATURE:
<221> NAME/KEY: Intron
<222> LOCATION: (53186)..(54272)
<220> FEATURE:
<221> NAME/KEY: exon
<222> LOCATION: (54273)..(54437)
<220> FEATURE:
<221> NAME/KEY: Intron
<222> LOCATION: (54438)..(55718)
<220> FEATURE:
<221> NAME/KEY: exon
<222> LOCATION: (55719)..(55826)
<220> FEATURE:
<221> NAME/KEY: Intron
<222> LOCATION: (55827)..(56043)
<220> FEATURE:
<221> NAME/KEY: exon
<222> LOCATION: (56044)..(56178)
<220> FEATURE:
<221> NAME/KEY: Intron
<222> LOCATION: (56179)..(57364)
<220> FEATURE:
<221> NAME/KEY: exon
<222> LOCATION: (57365)..(57631)
<220> FEATURE:
<221> NAME/KEY: Intron
<222> LOCATION: (57632)..(58262)
<220> FEATURE:
<221> NAME/KEY: exon
<222> LOCATION: (58263)..(58370)
<220> FEATURE:
<221> NAME/KEY: Intron
<222> LOCATION: (58371)..(58986)
<220> FEATURE:
<221> NAME/KEY: exon
<222> LOCATION: (58987)..(59186)
<220> FEATURE:
<221> NAME/KEY: Intron
<222> LOCATION: (59187)..(61821)
<220> FEATURE:
<221> NAME/KEY: exon
<222> LOCATION: (61822)..(62035)
<220> FEATURE:
<221> NAME/KEY: Intron
<222> LOCATION: (62036)..(62987)
<220> FEATURE:
<221> NAME/KEY: exon
<222> LOCATION: (62988)..(63125)
<220> FEATURE:
<221> NAME/KEY: Intron
<222> LOCATION: (63126)..(64298)
<220> FEATURE:
<221> NAME/KEY: exon
<222> LOCATION: (64299)..(64520)
<220> FEATURE:
<221> NAME/KEY: Intron
<222> LOCATION: (64521)..(64872)
<220> FEATURE:
<221> NAME/KEY: exon
<222> LOCATION: (64873)..(64995)
<220> FEATURE:
<221> NAME/KEY: Intron
<222> LOCATION: (64996)..(70290)
<220> FEATURE:
<221> NAME/KEY: exon
<222> LOCATION: (70291)..(70436)
<220> FEATURE:
<221> NAME/KEY: Intron
<222> LOCATION: (70437)..(70767)
<220> FEATURE:
<221> NAME/KEY: exon
<222> LOCATION: (70768)..(70923)
<220> FEATURE:
<221> NAME/KEY: Intron
<222> LOCATION: (70924)..(73571)
<220> FEATURE:
<221> NAME/KEY: exon
```

```
<222> LOCATION: (73572)..(73695)
<220> FEATURE:
<221> NAME/KEY: Intron
<222> LOCATION: (73696)..(78101)
<220> FEATURE:
<221> NAME/KEY: exon
<222> LOCATION: (78102)..(78236)
<220> FEATURE:
<221> NAME/KEY: Intron
<222> LOCATION: (78237)..(79438)
<220> FEATURE:
<221> NAME/KEY: exon
<222> LOCATION: (79439)..(79525)
<220> FEATURE:
<221> NAME/KEY: Intron
<222> LOCATION: (79526)..(81222)
<220> FEATURE:
<221> NAME/KEY: exon
<222> LOCATION: (81223)..(81387)
<220> FEATURE:
<221> NAME/KEY: Intron
<222> LOCATION: (81388)..(82196)
<220> FEATURE:
<221> NAME/KEY: exon
<222> LOCATION: (82197)..(82319)
<220> FEATURE:
<221> NAME/KEY: Intron
<222> LOCATION: (82320)..(83196)
<220> FEATURE:
<221> NAME/KEY: exon
<222> LOCATION: (83197)..(83369)
<220> FEATURE:
<221> NAME/KEY: Intron
<222> LOCATION: (83370)..(86499)
<220> FEATURE:
<221> NAME/KEY: exon
<222> LOCATION: (86500)..(86641)
<220> FEATURE:
<221> NAME/KEY: Intron
<222> LOCATION: (86642)..(87803)
<220> FEATURE:
<221> NAME/KEY: exon
<222> LOCATION: (87804)..(87877)
<220> FEATURE:
<221> NAME/KEY: Intron
<222> LOCATION: (87878)..(88470)
<220> FEATURE:
<221> NAME/KEY: exon
<222> LOCATION: (88471)..(88565)
<220> FEATURE:
<221> NAME/KEY: Intron
<222> LOCATION: (88566)..(91783)
<220> FEATURE:
<221> NAME/KEY: exon
<222> LOCATION: (91784)..(91863)
<220> FEATURE:
<221> NAME/KEY: Intron
<222> LOCATION: (91864)..(92802)
<220> FEATURE:
<221> NAME/KEY: exon
<222> LOCATION: (92803)..(93033)
<220> FEATURE:
<221> NAME/KEY: 3'UTR
<222> LOCATION: (93034)..(93203)

<400> SEQUENCE: 1
atttgaagtc ctcgttccac gccttctcat catcctgaac accgagctct gggactccgg      60
cggagaatct aaacgtaaag catcacccac ggtcgtgaac tgtaggctct cctggcatcc     120
gggatcttat tctggccttg gcggagttgg ggatggtgtc gcctagcagc cgctgccgct     180
ttggcttgct cggaccattt ggctggacc cagagtccgc gtggaaccgc gatagggatc     240
tgtcagggcc cgcggccggg tccagcttgg tggttgcggt agtgagaggc ctccgctggt     300
tgccaggctt ggtctaggtg ggtggatcct tgtaagcagg attagcgagt cactccacgc     360
```

```
tcaggttctt tagcctgagg gcccgtgtgc cacagcatag ctaccccgcc cttccagcct    420
cgggtcccta atactgcctt gcttcggttc cagtttccgc cgcacaactt cactcattcc    480
aaatgttaat ttctgcgttt tttttcagcc ccaattctgt ttctccaaat cagggatgat    540
tgtcggcctt ccacagaccc tcgcgcttgc caggattagg gtgttcgcgc cattgtggg     600 tagggtgtg gaggaaggga tccagaaatc ttaagtatta acttagatta gtgttagcaa     660
ggaagccgtc acattttatt tagccggac actctgacag tttgtgccga ctgctatttt     720
tgatcaaggc tattttgccc acttgtctat tttgtggccc aattgtctgt tttgctaaca    780
tcagaaagtt ataatgaaat aatctgcaaa aaatgtaagg tgctagaaaa ccaataatac    840
tgtgtacctt gaaatgcta atatacacct gttttgttac agaggtggag cacagtgaaa    900 gaattcaag atg cca cct aat ata aac tgg aaa gaa ata atg aaa gtt gac    951
          Met Pro Pro Asn Ile Asn Trp Lys Glu Ile Met Lys Val Asp
          1               5                   10 cca gat gac ctg ccc cgt caa gaa gaa ctg gca gat aat tta ttg att      999
Pro Asp Asp Leu Pro Arg Gln Glu Glu Leu Ala Asp Asn Leu Leu Ile
15                  20                  25                  30 tcc tta tcc aag gtgcttaatt ggtcaataat aatagatata tacattaact         1051
Ser Leu Ser Lys tatgattaat ttattaataa aatatgaatt tattttttc agggacaact ataattgtca    1111
caatctggaa gtgttcttat attttgcttg aaggttataa aatataaaac agttgctttt   1171
ctgtttactt ag gtg gaa gta aat gag cta aaa agt gaa aag caa gaa aat   1222
              Val Glu Val Asn Glu Leu Lys Ser Glu Lys Gln Glu Asn
              35                  40                  45 gtg ata cac ctt ttc aga att act cag tca cta atg aag gtttgtatgt      1271
Val Ile His Leu Phe Arg Ile Thr Gln Ser Leu Met Lys
50                  55                  60 agtaggtttt aactataggt ttggctatta gtggaactat aaaaatctgt tcttatataa   1331
ggtaatcttt gtgaaaatac ctggtaatat ctacatcacc actaaaaaat gcaatatatt   1391
taaatgtgaa ttaagtattt tagtgtataa acattgcta gtttctactt aaagtttcta   1451
aaagggtgtg taggggaaat agaatgagta tgttgaaaag taacataagg aaatatatct   1511
tgaggtccaa atgacaaatg cagacaatga ctgctatagg gatttgttaa gaggggaaat   1571
gatttaagag atgtcagaag acttcacaaa ggatcaatac tgaggagtag tgttagataa   1631
gtggaaggca atgcagtggt aagatagtaa gggaattcta gagctgttgg ttaccataaa   1691
taaatactga gaacaggaaa tatgtttatt ctttatattt gaggaaacaa ggtgcagcaa   1751
gtttgtagca gactgtagag aaaacaaatc ttgggtaagt actttgagat aggttgttga   1811
gggccttaaa ggtgtatttt atgctatcag caattgagaa ggcagtaaag gttttcgaaa   1871
cacaattgat aggtacaaaa atacacctta agaaggcaaa actgagtata ttatgtagga   1931
caaactgaag gaaattggag ctttgtagac atcacattat agcggagttt aaacctgaaa   1991
ttatggatta gaataatagc aattggaaca gaaaaaagt agtggaaaga cattacaaag    2051
ggagatgttg cattactgga tataagactt gaggacttga ggtaaaaagg gaatcaaaa    2111 atgtttcatg ctattaaaaa tctagaaatt gtagtcttaa gtaagaaaat tgcctggcat   2171
ggtggctcac gtctgtaatc ccagcacttt gggaggccaa gcaggagga ttgcttgagc    2231 ctgggagttc aagactagcc tggataatat agtgagtcct tgcctgtacg aaaaaatttg   2291
ccgagcatga tggcacacca agcatgatgg cacgccaagc atgatggcat gcacctgtag   2351
tcccagctac tcaggagact gagatgggaa gattgcttga gcccaggagg caggaggttg   2411
```

```
cagtgagctg agattgtgcc actgcactcc agcctgggtg acaaagtgag gccctatctc      2471
aaaagcaaaa aaaacaaaaa caaaaaccaa aaactatttta ttcagcaaat atttactgaa      2531
cgtctccatg tgccagccat tgctggcact aaggatcata acaaataaaa cagaattttt      2591 atttcagtg cttacattcc agtataaagg catattgaaa taacctttt ttaatgttta        2651 g atg aaa gct caa gaa gtg gag ctg gct ttg gaa gaa gta gaa aaa gct      2700
  Met Lys Ala Gln Glu Val Glu Leu Ala Leu Glu Glu Val Glu Lys Ala
              65                  70                  75 gga gaa gaa caa gca aaa ttt g gtaagcacct tggaaaaagt ttattatggt         2752
Gly Glu Glu Gln Ala Lys Phe
            80 attaaataat gaattccatt tgttcattaa actgtagaaa attaaattat attctataaa      2812 atatatatat tcagtttatt tttaatatat aacatttaat aataaatatt tctagactcc      2872 tattttatgg atctgccata taatactttt tgttaccta taatcatgat ggactcttt        2932 aaaagaatta attttgttat tgaaatttat ttaaaagttt gttttgtggt aactaatcaa      2992 ttaaaacgtt tttctttttt tttaaaaaaa tag aa  aat caa tta aaa act aaa      3045
                                        Glu Asn Gln Leu Lys Thr Lys
                                                85                  90 gta atg aaa ctg gaa aat gaa ctg gag gtatgtcttt ttgtattccc               3092
Val Met Lys Leu Glu Asn Glu Leu Glu
                    95 taggatgtaa ttgtcattaa ttttattttg aattgttttc aaatttaaa attattgttg       3152 gctggaaaaa ttataaggat gattgtaatc atggttattt gtttattctg tatatgttct      3212 acatgcctat tatgtgcctt atatagtact aaggactgag catatggttg tgaacaaaat      3272 aagaagttaa ctgctggatg gagcttatag tcttgggaaa tatacagaaa gattactagt      3332 aactgaggtg gagggtgggt ggggatttga ggaatagtga cgaaagggtg ttatagaagt      3392 aattttttgac aaagctgaag gctaaaatat gaatgtattg ttgaagaaca aaatacattg    3452 agattcctga gaaggtagga atgtgataca aatggatcag cctttgaaag gaggaatacc      3512 cttttccttt gtgttaggag aggaggatga gtggatgagc gtgggaagag tggatgtgta     3572 tagaggcttt tatgtttgta ggcataatgc ttggaagttg aggggttggt gatgacatct     3632 tctgttaaaa agagtgggaa atggtgtggt cacattttaa ggaaattagg taaaatttga     3692 aatatattgg agacaggact ggagagttgg ggatctggag tcagacagat ttgagttcta     3752 gtcctgattc ttctactcgt taactctctg aacttggatg acctattgtt tttgattgta     3812 tatccagctc ctgggaaaat gccaagcact ttcaataaat actaaatgaa ttatggagtt     3872 ggatcagttc tgtgttagtg tttagctagg tagctgctgt agaatagaag ggtagcacag     3932 ttgaagatat tggtaggaaa gtggttgaag tgatgattat gaagtcttaa ctgaatagat     3992 aaaatcaaga ttggggttgg gtgggcagaa gggtagggat atggagggag aagatgaggg     4052 gttagagtgt cctgtgaggt cgaaggacag gcatagtggg aataattgaa agaatgttct     4112 ggttggacaa ggatctgatg tgggtgtggg agtgagagac tatagtgaat tcaagaaaaa     4172 aatagactag aacaaaagtt atgtggagat tgcttagtgg gcatttgata gacatctgtg     4232 ggccacatgc ttaaattccc agtgcatttt gcggagttac tggaaggttg gtggcttgtt     4292 tctaccatga gtaggtaaag atggagagca ggatattttg tgagaaagca gctgaagttt     4352 ctataggatg atggaggaat gataggaatg atcacctgaa gttgcagggt ggggtaaacc     4412 tagaagcacc aacaccttct tctgacccctc atgtatttgg aatctgaaag aatgagcacc    4472 ttccaattga aagagttcca agggcattag tatactaaag gatccaaatt gcagctaagc     4532
```

```
caaggagatg gaaaggagga ttcagtaaag aatctgagga tgtgaaatat taatttatct    4592
tggaagagaa ttttagagag cacaatggaa tgcttttgg aggagagaaa gagtaagaac    4652
aatttggtta aggtagagga ataacagaac tataaggtga agaaatgaat gtgagacaca    4712
ttagatgacc aaatgatttg atgttcttgg ccatgacctg aattaacaag actgtgaggt    4772
aaaatggatt taatcggcta caaatcttaa gataaccaaa acctgagctg tttaatatgg    4832
tagcactagc actaaccact tgtagctatt tatatttaca ttggttaaaa ttaaaatgaa    4892
aaatttagtt cttcagttgc actagccaca cttcaaatgc ccgaacatag ctacatgtag    4952
cgagtggcta ttgaactgga cagcactgac agcatgtcca ttatgctaga aagtcctatg    5012
ggacagcact ggtctaaaca gtgcatggta tgagagaaag ggcaggttaa ggcactcagc    5072
ttcactgact ggggtggaga ttctgatggt ttgtactcag gttccagatc cctgaggctc    5132
aggaaccttt gcagtttagt ctggttacct gtggcccagt ggttacaaca gaatgattaa    5192
cagtcaattc tttgcatctc tgggtggctc aggaaaaatt taaggagtta ttagctgtga    5252 actaaccta agtaagttaa attaaaaaaa aaaagttct taagctaata tgattttaaa    5312
tatctgcact gaagtataat gcaaatttaa attcagcata attatttgct tgttgttgac    5372
tcatttgaac ctcaaaatat aatgggatta atttatactt tgggtttatt actttaag     5430 atg gct cag cag tct gca ggt gga cga gat act cgg ttt tta cgt aat       5478
Met Ala Gln Gln Ser Ala Gly Gly Arg Asp Thr Arg Phe Leu Arg Asn
100             105                 110                 115 gaa att tgc caa ctt gaa aaa caa tta gaa caa aaa gat aga gaa ttg        5526
Glu Ile Cys Gln Leu Glu Lys Gln Leu Glu Gln Lys Asp Arg Glu Leu
                120                 125                 130 gag gac atg gaa aag gag ttg gag aaa gag aag aaa gtt aat gag caa        5574
Glu Asp Met Glu Lys Glu Leu Glu Lys Glu Lys Lys Val Asn Glu Gln
        135                 140                 145 gtaaagcact ttttttttcc atgaatcttc actgttcaag ttacctggct ttttattatt    5634
attggtaaca atatcaattt ttatattgta tgttatattt gaaaaatgat gtacacttat    5694
ctctaaggtt ttatatcact gttcattttg tcatcaccaa ttttaaaata taatggtact    5754
tctagtgaat atgacttgaa gattaattct ttatatttgg aagtacattt ttctcaggac    5814
atcaaacttg ttacctaaaa ttaatgcttt tgtctggaag attggtatca agtaactaat    5874 agatttcat aaagaagtga tctttctagt gccatagttt attttgggta aaagttatat    5934
ttgttcattt caatgtattt atatgattag tagattcgca aatgaatctt cgatatatt     5994 caataatggt taattaaata tcttgttttt ggttgtacct tattttatgt gagatatata    6054
tatatatgta tagttttga aaagttgtgt tcatgtcagc agtttataaa tcacatattt     6114
aaaataacat ttttaatgca tagtttttat tacctcgtta ttccttgtta taaactaata    6174
attcttgcag tgttcacttg aatttagttt taggaaaaaa gttttttgca gatcaacttg    6234
tatttcctgg aagaaaattt cctatttac ctcagcttcc tatttaatgt attatttatt    6294
tatttactta acatttattt gttttttatt tcacctgaac tgttagtaaa cttagtaaaa    6354
tttggtgcct acatgtggta actgtcctgt cccttatact cagaaacgtt ttccacccttt   6414 gtgtcccttta ggtcattgtt gtgttatatt ccattttatt tattttgtcc attgttctct   6474
cagaaattga gggtcataca ttttaagaaa acaatgatat gctatttaag agaatgtatc    6534
ataaattgat ttgtaaggaa aagtatcccc attcttcatg tatgtatttt actctaaaat    6594
gttgaagaat catatagaag ttagctatga aaacaatgtg gtagagaaag tatggatcga    6654
```

```
tgccacttaa atgttaggaa gaagctctta gagcattatc tgtttagcta actgcaaaac      6714
atagcagaca tgtggatttt ttaatagtca tcaaggatct aacttataat atacactggt      6774
agaattgctt aggggatgt ctgtggtttt ctggactttt gttcttctat atagacctgt       6834
atcagttgac ttatcattca taccacacac ccttagctaa tcagaactac cttgtccatt      6894
tatatcttag actattgtct tttttcatag tcacacacag agaaaacttg aatatatggc      6954
ctgtgttcct ttttggctgc tcaattcctt gagatgaaat atgggtatgg gttgctttgg      7014
caattacttc tttgccgtta accagtcatt cagttttatt gagtctttac agcataccag      7074
aggctgctag ttactagtga tatagtgggc aactatgttc tggttctcaa gaatattcat      7134
agtcaataat aagcataaca tagtgataat atgatactta gggagataca taaggtcata      7194
ttctggcata ctctggagag agataccgta atcagccttg aggtgcagga tgtgatctgt      7254
aaactgagac ctgaagtata gttagactgg taagaggaat gaggatatat atggtggtta      7314 ataaagaac attctgggta gaagatatag catttgctaa gacctagagg taagagatgt       7374
tatggagtat ttaggaaact acagttattc attttgactg aaatataagt gaaaatagct      7434
ttcatagagt ccttactatg tgccaggcac ttcatatgca ttaattcatt attgcttatt      7494
tgatacttgt catatgagat agttgtcatt tctgccatga tacagatgaa gaaatggaga      7554
cacagaaaga gtaattgccc atggttgcac agcttataaa tggtaaaggt aggatttgaa      7614
aacagtctta ctcaagagtc tgtgctatct tgccttccca gttttatttt ttatgatcct      7674
ctggagagat aagcaagggc cagttcctaa tgaatttggt tcttttcctg aaaggagcca      7734
gtgaagagtt tgagcacag gatatcatga tcagatctat actttaaaag tttactgtac       7794
tttgtagaga gtggattgaa aagggccaag actagtaagg aaacatttgt gttaattcag      7854
ggaagtgcta atgatggcat ttgcctgaga aagacaagtg tgagagaagt agatgtaatt      7914
ggatgtggtg aatgtaattg gttgttggag gagagggagg atggagagtc tgcctaattt      7974
tgtgggttgg gccactaaat aggtagatag tgccattcat taaggaggaa cacaagagga      8034
atttggaaag cttgagatta tttcagtttt gtagatgttg agtttgaggt tcttctgggc      8094
atattcaaaa agggtatctg tggatatgga attcacaaga gaccctgtac agatgatgag      8154
gatttatgaa tcatcaatgt agacattatt gaagccagag aagtgattgt aaggcacgtc      8214
tctgagaaat gtctaataaa gcaatgaaat aggaagagtg cttcaaggaa aagctcaaga      8274
aaggagaaac agagtgtgat gtttgagaag acaagggaaa aaacattaa tagcattaaa       8334 tgctttagca ttaagttctt ggcttctctt cttgtaaaaa tttcccaatt cagaacacag      8394
tgggattatt aactttcaat tgataataat aatgataggc aaacttctaa aatttgtatt      8454
gtagtttgca ttttattata aactttcttt aaattttat tttgaaaat gtcatatctt        8514 cataaagatt gtaagaaaca cactgttggt gttaatgtaa attagttcaa ccattgtggg      8574
agacagtgtg gcaattcctc gaagatctag aagcagaaat accacttgac ccagcaatcc      8634
cattactggg tatatacccca aaagaatata atcattttc ttataaagat acttgcacac      8694
atatgttcat tgcagcacta ttcacaatag caaagacatg gaatcaaccc aaatgctcat      8754
caatgataga ctggataatg aaaatgtgga acatatacat catagaatac tatgcagcca      8814
tcaaaagaga atgagaggtc aagcgtggtg actcatgcct acagtcccag cactttggga      8874
ggccgaggca ggcagatcac ttgaggtcag gagttcaaga ccagcctggc cagtatggtg      8934
aaaccccatc tctacaaaaa caaaacaaaa caaacaaaaa ttaactggtc atggtactgt      8994
atgcctgcag tcccagctac ttgggaggct gaggcaggag aatgacttga acccagaagg      9054
```

```
cagaggttgc agtgagctga gatcgcacca ctggactcta gccttagcaa caaaactaga   9114
gtttgtctca aaaaaaaaaa aaaaaaaaaa ccggaacaag atcatgtcct ttgcagggac   9174
atgggatgga ggtggaagcc attatcctca gcaaactcac acaggaacag aaaaccaaac   9234
actgcatgtt ctcacttata agtgggagct gaacaatgaa aacacatgga cacatggtgg   9294
ggaacaacac acactgggac ccgtcaaggg gtcgggtgg gagaacatca ggaagaatag   9354
ctaatggatg ctgggcttaa tatctaggtt atgggttgat ctgtgcagca agccaccatt   9414
gtacacattt acctaagtaa caaacctgca catcttacac atgtacccca gaacttaaaa   9474
gttgatggga aaaagaaaaa caataaccac ccacataccc ttcatataga ttcaccagtt   9534
cttaatgttg tgccaacttt gctttatctt tttgtcagta tttttacaca cacatgtatt   9594
tctctgtctc ttgtttgttc aatcacattt tttgctgagt catttaagag ctaattgcag   9654
atatgatact ttgcacttaa atatttcagc ttgtctgttt gaaaagaaa gatgttctcc    9714
tacaatgaac acaatataat tgtcatgctc aggaatttta atattgattc aacaccatta   9774
tctagtccat aatgagattt cttctaatgg cccaataata tccttcagtc tccccacctc   9834
caatatccaa agttctgtca aggatcacat actacatttg gttctttatt atagactttt   9894
taaatatcgt tgtataccat tgtgattcta tcgtctcctt taataaagag gagaaccaga   9954
aaaatgaaag gtcataagag gaatgaggtt tggagaatag gtgaaaaaag gcatcataat  10014
gtttataata atgtttgcct gttcagagaa acaagaatca cagataaagt cacttatatg  10074
tagataagag aatgctgtat tactttttgc tattctattc actgatcatt tttctaagaa  10134
ctctgtatgc ttcttgttta actcttatgt cagcatgtat gagaaaactg agttaaagag  10194
atgttaagta actcattcat gctttactag aaattggttg atgagggaca taaacctagg  10254
ccggtgtgat tttagattgc ttcttttaac cattgtgttg tattgcctta tatttctaag  10314
taatttatgt tcactgagag caaataatag tctagctatg acttagaaaa gtaaaataaa  10374
gatgttgggc agaaaaccat tttattaggg gttttttgg aggagcagat taatttgttt   10434
ctgtattctt tggttagttt gtgtgtgtgt tctttttaat tctttaaaat gaaactgttt  10494
aatccttaaa tccttaagtt ttgaaaattt tggcctatta tttatgtgtt aggttgatat  10554
taaatcctta atagctttaa cattttctac tttgttagag aggatttaaa atttaagtag  10614
ataagctgaa tatctggctt tatattaaat tactgctgat ggccaggcac agtggctcat  10674
gtctgaaatc ctagcacttt gggaggttga ggcagatgga tcacttgagg ccaggagttc  10734
aagaccagcc tggctaacac agtgaaaccc cgtctctact aaaaatacaa aaattagcca  10794
gttatggtaa tgcatgccag taattccagc tactcggtag gctgaggtgg gagaattgct  10854
tgaaccggga ggcagaggtt gcagtgagcc gagatcgcac cactgtactc cagcctaggc  10914
gacaaagact ttgtctcaaa aaaaaaaaa attactgctg aatttatct tcttcttatt    10974
tattttttt tttactatt ttag ttg gct ctt cga aat gag gag gca gaa       11025
                        Leu Ala Leu Arg Asn Glu Glu Ala Glu
                                 150             155 aat gaa aac agc aaa tta aga aga gag gtaaaaaatt ttagtagttg           11072
Asn Glu Asn Ser Lys Leu Arg Arg Glu
        160             165 tggtggttca acaaaggtac ttattaaaat aagtacctaa gtttacataa atttatattt  11132
taaccaggac tggagtcttc taagtaactg atgttttcag actgatttta tggtatgact  11192
ttgtctcagg gaaatagaaa acaaagcaaa atgtgaggcc attaagtatt acattcatct  11252
```

-continued

```
caggtctatg cgggtaaatc ttttttttgtt gttttataag ccattctttg ctagttttct      11312
aattgaatag atgactggat ttctattctt atttctctta cccagaatcc tttaaaattt      11372
tttgttactt gtggaatctt ataaattctg attatcattt ggttctactg agccaaataa      11432
tgtttgtaca ttgtttattc tgatagaagt tcttaagttt ctaacataat tgaaatatta      11492
tttgttttgg tagataatta gtattctttc tttggttatt caagataata tgcatcattt      11552
tcccaaaatt ttttttgtttt ctttagtttc tgattattat ttttaattat gtattacctt     11612
tctcatttct aattaccgtt ttcctgtcct tttctgtag aac aaa cgt cta aag         11666
                                              Asn Lys Arg Leu Lys
                                                              170 aaa aag gtgaggcttt aagtgtggtg aaatcttggg aatttaaaat atgttgtgag        11722
Lys Lys agcactattt agaggatatg attttgttat tctgaatagt tttgtaattg aatgttgtgt      11782
ttggttacct tcag aat gaa caa ctt tgt cag gat att att gac tac cag       11832
              Asn Glu Gln Leu Cys Gln Asp Ile Ile Asp Tyr Gln
                  175                 180 aaa caa ata gat tca cag aaa gaa aca ctt tta tca aga aga ggg gaa       11880
Lys Gln Ile Asp Ser Gln Lys Glu Thr Leu Leu Ser Arg Arg Gly Glu
185             190                 195                 200 gac agt gac tac cga tca cag ttg tct aaa aaa aac tat gag ctt atc       11928
Asp Ser Asp Tyr Arg Ser Gln Leu Ser Lys Lys Asn Tyr Glu Leu Ile
            205                 210                 215 caa tat ctt gat gaa att cag gtaaaatggc tagaagtcaa ttcagagcaa          11979
Gln Tyr Leu Asp Glu Ile Gln
                220 tggttcctaa aaactttaat ttcattacaa tgtaaatata atatttagcc ctacatgtaa     12039 attccctggt ataaatctgt cactatgtac ttgtaaaatg tgaaataaat tacatctttg     12099 aagttgcaac ttttttagcca tttttatatt tgcctgtctt ggtcattaag aacaattgag    12159 gtccttatgt actatttttct tgattcaatt tgatttaatt ggtcaatgcc aattagtaaa    12219 ggtctataaa gaattctctt tttttctaga ggacacttat ggctgcgttt aattttaatt     12279 tggtttaaat ttcagttttt ttaaaattac ttttttaatta tagtgtcttt aacttttta    12339 g act tta aca gaa gct aat gag aaa att gaa gtt cag aat caa gaa atg     12388
  Thr Leu Thr Glu Ala Asn Glu Lys Ile Glu Val Gln Asn Gln Glu Met
     225                 230                 235 aga aaa aat tta gaa gag tct gta cag gaa atg gag aag atg act gat      12436
Arg Lys Asn Leu Glu Glu Ser Val Gln Glu Met Glu Lys Met Thr Asp
240             245                 250                 255 gaa tat aat aga atg aaa gct att gtg cat cag aca gat aat gta ata      12484
Glu Tyr Asn Arg Met Lys Ala Ile Val His Gln Thr Asp Asn Val Ile
            260                 265                 270 gat cag tta aaa aaa gaa aac gat cat tat caa ctt caa gtaagaatta       12533
Asp Gln Leu Lys Lys Glu Asn Asp His Tyr Gln Leu Gln
                275                 280 cttttagaat aacttattta ttcagacttc atattatctc attactattt atttgacact     12593
agaaagtact ttttctagga tgtgaatttt tgtctgtctt tttaatagtg taatatcttg     12653
tcatgttggt atatttgtcc atatgtgttt ctccaatcac ctcacaaaca ctaattttg      12713 caatttagga tatataaatg atacttgaat gaatgtgtag atagcagtca ttatgggggtt   12773 ttctataaaa gactactgaa atcctgtggg atcataacat ttcattttat cttaaaataa     12833
atacattata aatgtattag aaaccaatac attgttcagt atttatgtgg attaaatttg     12893
tttaaaaggt agaataatgt ttaaaaataa aatttttctag taatgaaaga taattatgca    12953
```

```
attataagat gcagaaacta ttaaatgtca cctataattc caggatgact tcaatgataa    13013
atacacatat gtaatgtaat gtatccgtat gtatgtgtat ataagtatga atacgtatgt    13073
gtgtgtatgt agatatattt atatatataa tgtatatgta aatatgcaca ggtgtaaata    13133
tatgttacat cagtttgcaa caactcttga aataactttg tcttttag gtg cag gag     13190
                                                      Val Gln Glu
                                                          285 ctt aca gat ctt ctg aaa tca aaa aat gaa gaa gat gat cca att atg     13238
Leu Thr Asp Leu Leu Lys Ser Lys Asn Glu Glu Asp Asp Pro Ile Met
        290             295             300 gta gct gtc aat gca aaa gta gaa gaa tgg aag gtattttttt tcaattgaca   13291
Val Ala Val Asn Ala Lys Val Glu Glu Trp Lys
    305             310 taataacttt ttctttttgt attttagatt taaattttag tcttatttt ctttaaatgt    13351 cttatactgg tttataacac gtttattagg gttttaaac ataagtttat tttatttatt    13411
ggttagaaaa gctctagaac tgtccttttt gatctctagc taatttgtta ttgaatgacc   13471
tctttcacat caatgagttt aactttaaac ttttgatag aagtctaact ccaaaatata    13531
tttggcatct aaaatatata attcgaaata taatttaaat tttttactt aactcatagt    13591 taccttatat acattagtta aatagttgca ggtttaattt tagttttct aactaaatgt    13651 caggttcatc agtgggaatg ggaataagca aagggatcag aataacttgg gaagccttt   13711 caaaatacac ttttcttcct caccaccact ctccaacctt aaccaaattg tcaggcctta   13771
ccatattaga agctgggatt atgatggttg tatacttgaa aaacatcaga gattattctg   13831
aatgaataat tctaattta aaaactatca cttctagagt cattgctttc tagtatggtt    13891
cacataaatc ttgtgggcag tttggaactg gttagcatct agggagctca gataacctat   13951 atttaaaca aaagcattag caatggaaat aaggcctata gaatcagtca tgtctccata    14011
aactttatat aaagggccag acagtgaata ttttagacca cctggtctct gctataacta   14071
aactctgctt atagcatgaa agcagccatt gacaatacgt aaatgagtga gcaaggtggt   14131
tttccggtaa aatttttattt acaaaagcag atgggaggcc agatttgacc tttgggccat  14191
agtctaccaa cccctggaaa aaacagttgt ctttaccaga ttgaatgttg gcagggtaaa   14251
tggtgacatg ttatatgtat tctgtacttt gttttgactt aataccattt cataattatt   14311
ttatatcagt acgtatagta ttgctgttct tttttaaaggc tatgtaattt ttcttttat   14371 acaggtgtta atttgataat ttgtgaagtt tatgaagttt ccaattttgg ggttgtaaac   14431
tgttttaatg aatatcctta tatatgttat tttgcaaatg tacaagtata tctgtggaat   14491
aaattgctgc aagtgttgta attgtcatgt atgttgcaaa tacattctaa cagtttgtca   14551 cttttttgc tttatggcat ttttttgctgt gaaatatttc tttttatgct tagttaaatt   14611
tattattttt taatgacttt tgacatttgt tataatgaga aaggcttctg agtataaact   14671
tgttttctca tcttttctcc taatatcttg ttttgttttt gttttgtttt ttgtttttga   14731
gacagagtct cactcagttg cttaggctgg agtgcaatgg tacaatctca gctcactgca   14791
aatgccacct cctgggttca ggtggttctt gtgcctcagc ctcctgagta gctgggatta   14851
caggcatgtg ccgccatgcg cagctaattt ttgtagtttt agtagacatg gggtcacact   14911
gtgttggcca ggctggtctt gaacccctgg cctcaagtga tcctcctgcc tgggcctccc   14971
aaagtgctgg aattacaggt gtgactctgc ctggccttt tttacattta aatcttcgaa    15031
acatataatt cattttgatg taaggagtat catgtggatt caacagagct actctgttgt   15091
ccaaacatct tttattgatt atttcatctt ttattgaatt gattgatcta ttttctagca   15151
```

```
gtgtatactt gttttaattt gtgtatgttt taatatctaa aaacgttatt attttttctgc    15211 ttttagactt ctttatgaat attttttaatg tgaattatag aactggcttg tccagttctt    15271
aaaaaatatc ttgtggattt ttattgggta tgtgttaaag ttataaattg ttttatagat    15331
tgatttagga taaaccttttt tatgttattt ggtccttcta gctaaagaac acaagatacc    15391
ttttctttca ttcattcaag atattttatg cctcttggtt gcattttaat gcatacttca    15451
taaagatcaa ttgtataaaa cttttcacag ttgtatggaa gtacttcttg tttataaatg    15511
agttttgaaa ggttgaaata tttttaaaga ttgaattata aaaaagaaa attcggtata     15571 tatttttaaaa tcattttcta tttgaatttc aggttgtata tacaaaagga acagagatta   15631
tgccagtagt tgctcatact ttctcatttc aaataatttt tattttctgt atcataaatc    15691
tactaacggt gttattattt tatgataatg aagaatgttt tattaacttt cctttttgcat   15751
```

| aacagattct attgtgttta tttctag cta att ttg tct tct aaa gat gat gaa | 15805 |
|---|---|
|                                  Leu Ile Leu Ser Ser Lys Asp Asp Glu<br>                               315                 320 | |

```
att att gag tat cag caa atg tta cat aac cta agg gag aaa ctt aag     15853
Ile Ile Glu Tyr Gln Gln Met Leu His Asn Leu Arg Glu Lys Leu Lys
    325                 330                 335 aat gct cag ctt gat gct gat aaa agt aat gtt atg gct cta cag cag    15901
Asn Ala Gln Leu Asp Ala Asp Lys Ser Asn Val Met Ala Leu Gln Gln
340                 345                 350                 355 gtaaaatctt aacagaattt tgtttatcaa ccagttttat tacagttgga actctgaacg    15961
atgtctttta tttattatat catcagtgcc tagtgtagcg gctggtacta ccaagtgtat   16021
aataatgtct tttgaaattt cttctaccac ctggtcccaa taaaaaatta gaattaagtt   16081
tagatcacgg attagactta gaactagagt tactgtgttt attttttctat gtttatgtgg   16141 atagtacaca cattgttttg gttagaaatt atttaacaag aaatgattaa aaacttttag   16201
aaatttaaaa taattttata ctcttttaag gttatttttta ctgtatctta gtcctaacat   16261
accctataca atgtgaaata agctaaaagc atggttataa tttgactgtg ctacctatt t  16321 tattttttagt gaaaataacc caaataaaag gaagtaatac ttttattatt tgtgctgtag   16381
ttatagtcca caagtaagaa gatgatttga aaagtgtatg ctgaataaga acaattacag   16441
gggacaacat ttttttaataa agtacgaaag gggaaaaagc taagttgaat aaaagagaaa   16501
gcacagagca aaacagaaac atacaaaatg gtaaaaaggt ggaattgaat ggaggatgag   16561
gaaagtaaca tataaggaag tatagaagcc ataaacatta gggagttctg gaaatcctat   16621
tttccagagt gttagccatt atatccatct ttcagtattg gagtaacagc agtgtaccta   16681
tcattgtgta ttacagttga agtgtacaaa atggtaaaag gcatacttgt acccacaaga   16741
aaatatgttc tacagtcttg ttgaaaaaaa tcagacgtac ttttttcctt acctttttag   16801
```

| gttaatattc atgaagggat atatattgtt ttaaaatatt ttatag ggt ata cag | 16856 |
|---|---|
|                                                              Gly Ile Gln | |

```
gaa cga gac agt caa att aag atg ctc acc gaa caa gta gaa caa tat    16904
Glu Arg Asp Ser Gln Ile Lys Met Leu Thr Glu Gln Val Glu Gln Tyr
    360                 365                 370 aca aaa gaa atg gaa aag aat act tgt att att gaa gat ttg aaa aat    16952
Thr Lys Glu Met Glu Lys Asn Thr Cys Ile Ile Glu Asp Leu Lys Asn
375                 380                 385                 390 gag ctc caa aga aac aaa g gtattttat aaatatatag ttattttata           17001
Glu Leu Gln Arg Asn Lys
                395 tacaattatg tttttaacga ctttattttt attaaaataa aatgtcaagt caatattgag   17061
```

```
ttttctccat ttgaatttta tattttcaaa aaattgtaca agatatttat tattatactt    17121
atattactag tgcttacatt tgtaaatgat ggatgcattt tctattattt ttctcctctg    17181
gtgaaaatta cattaacgtt tattaccagg tcactggtat gaaagaaatg aaaaattgtg    17241
atacaattat ttttatttaa ctttttataa ttaacaaaga atggaagata ataaaattt    17301 gaccagtgta acagcattgc agatagtttt cagaggtaat ttcacattaa tcttacccaa    17361
attaatgttt catcatattc tccttaccct gagccatatt accttttta acacatcaaa     17421 ttctatgaat ataagttctt acaatatctg tgttgttata tttccatagc actacatact    17481
atagttatgc cagggcacac tagtgcgaac tgttcatggg aaattcatgg acatgtttat    17541
tataattggt gactatgtat atatgtatac actacattta tacacacgcg catggaatca    17601
ctatttcttc ttcatgtcat atatatatac atatatacac atatatatac atgtcatatg    17661
tgtgtgtgta tatatatata tttgtatata tgacatgaag aagaaatagt gattccgtgc    17721
acatatgtgt gtgtaagtgt agtgatgtgt ttgcaggtac ggttgtaatt tcaaaaatga    17781
agcaaaagcc ttgctcagga gataattgaa ccaatactta aaggaagtaa aggagtgaaa    17841
catgcagatg gctctaagca gtgggaataa gttcaaaggc agtaaagcag gagtgtacca    17901
atcatgtctg agaacaacaa agaagtcttt ttggctggag tagagtcagc aagtgaggca    17961
gtgataagac cagagaggta aacagaggcc atatcatatg gggccttata gttcattgtg    18021
cagacttggc ttttaagtga aagggacac cggggaaagt ttctgaagat agaaatgata    18081
taatttgact taggctgtgt ttgcagtaga ctgtaggagt ggtaaataag aatcagggag    18141
acctgttaga agactattgc aataatctgg agaaaagtga tggtggtttg gggcatggtg    18201
gtagcagtgg agttactgga tgcagcagtt ctggatgtat tttgaaagtg ataaaaatgg    18261
aatttgctaa cagatcagat gtaggatgtg agagagagag aactcttggt ctgaaccaaa    18321
agttttggtc atggtggggt tgtgggaaga gcaggttgag agataatcag gtacttaatt    18381
ttagacatgt taggtttgag atgcttatta gacattcaag tgaaggtgtt aagtaggcac    18441
ttgtatataa aagtttaagg tttaggacaa caatctaggc taaagatatg tttggtaact    18501
gtctctgtaa aagtaattga aataatgagg ctggctaaga tcaccaaggg agtaaatgta    18561
ggttaagaag aaaaatctaa agagcttcta ctttagcagc tggggagata aaaaggagct    18621
accaaaggag actgaaaagg aaagcccaga gagctaggag gaaaagcagg agtatggaga    18681
gccctgaaaa ccacatgagg aatgtaacca aggaagaaga aacaactgct ttcagagctg    18741
tgttcattgc tgctgatagg tcaagatgat cactaaaagt tgactattgg acttagcaat    18801
ggtcattttt ggttcaagag aaaatgggta gagaggaaat gtaataaaga aatataggaa    18861
ccctttccca ggactgtttc tataaagaga aggagaaaac aaggtggtag cttgagggaa    18921
aagagggatt aagaaaacat ttttctcttt aagatggaag aaataactca tgattttagg    18981
ttaataggag agctccatta aagaagaaac attaatgaat caatgaagtg gagagagaga    19041
acttctggaa caataatatt tttaagaatg caatgggatg ggatcctagt gtgccagtga    19101
agaggttggc cttaactagg aacacagagt tcatccataa ttgtagaaaa gaaggtagag    19161
tgtatagata tcgatgtagg tggcttggta gacatcctgg taatgggaat ttgtggaagt    19221
tctaaactgg ttgctgcttt tttctcagtg aacaagggag caaggttctt agctgaaggt    19281
gaggatagga gaagatgttt cataagtttg aggagaaaga agagaagtga agtataaaa    19341 tggtcatctg aaagattgaa gacgtggaga atgtggtatg actgttgagt aacttcaaga    19401
```

-continued

```
gcccacgata tatatatgta tttctattta tgtgtttatt atatttgtat cagaacactt    19461
tgaaagtagt ttaaactgct ttaaaaggat gactaatagt atggattgtg cgtattctaa    19521
ttactaggag aaaaagtggc aattgatctc tgctgtcaaa taaggaaaag gacttatctg    19581
ataacacttt agtcagtccg tagttatata atccctaaag ctcacagaag gtgtgtgtac    19641
tagactgtac tctacatctt gaacttaact tgtaaaacgt aatggctaat ggtattcttc    19701
cttcataaga ttaggattag gtttagttat caggaacaga gagctgaaga ataatggcaa    19761
aatcaagata gacattttat tctcatctat gtaatggcct agaattaagc attccagggt    19821
gttgccttca tctgccccat ccaaaatgga tggaatgcag ctttatctca tgtctgtgtc    19881
ccaaacagca agacagagga agaggggcaa gagttaaaag catgtgctga aggataggca    19941
ggtaaatata gtgtttattg tgtagggcca tgtggaagaa tgataggaga atagatatgt    20001
ggatggaagg gagaatagat actggggac  aactcagcct gtgtcatgtt ccacagctta    20061
gatgttagct ccagacagct gtgctcattt cttaaaaact tttgtgatct caaacgtact    20121
agttttatgc ctaagtccaa tattaaatat ataacctata tattagtaaa tgcttataat    20181
gaatgagtgt gagaatgatc tgtcaatcaa ttttggaatg atagcaatat tatgttttgg    20241
tcttttaaca atttagtaag atattacaag taggcattta ggaagttttt agcttagttt    20301
ggattaaatt tagctgcaag tgacagaaaa atcaagcata atacaataat ttaaacaaga    20361
tagaaattta tttctctata atatagacaa agttgaagca actagggcag gatttgtgtg    20421
acagatgctc aaatatcccc tatcaggaac cctgtctctt gttgctgtgc ctatctcaac    20481
atgtggtttc taactcatgt gaagttgcca ccctcatatc catgtggatt tcagctagca    20541
ggaaggagga aagagaagag agattactcc tttattttaa aaacattttt tttttttttt    20601
ttgaaattca catatgaact ttgcgtttat attccattac tgacatgacc acacatagct    20661
gcttgtgtgt aagtggaaat ttagttcttt atttcaaatg gccacgtgtc aagctaaaaa    20721
tccatagttt tagtacagtg gacaaaaggg aggttaaata ttaggaacag ctagcagtct    20781
gtatcacaat gatcattttt tgtaaagcag tattttgcaa ccttttaaaa tccatacccc    20841
ttcagctaag aaggttttac tgaacttcag ttttttagta aattgtatta gtaaaaccaa    20901
aacaaaactt tcatcttaca aatataaaat gacaacttta aaggattttt ttttaatggc    20961 ataccactt tcttgccacc atgttgggat cactgatttg aaggaataag tagtcaattc     21021
aattcatgat ttttgttttt actctgtag gt gct tca acc ctt tct caa cag     21073
                                    Gly Ala Ser Thr Leu Ser Gln Gln
                                                        400 act cat atg aaa att cag tca acg tta gac att tta aaa gag aaa act     21121
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa     21169
Lys Glu Ala Glu Arg Thr Ala Glu Leu Ala Glu Ala Asp Ala Arg Glu
                425                 430                 435 aag gat aaa gaa tta gtt gag gct ctg aag agg tta aaa gat tat gaa     21217
Lys Asp Lys Glu Leu Val Glu Ala Leu Lys Arg Leu Lys Asp Tyr Glu
            440                 445                 450 tcg gtatgtattt ttatcttgtc attcaaggag cttagaatta ttcttgccat           21270
Ser tcacagacta ttctgtgcta tttactgcat accatttaaa aaacattcca taagtatctt    21330
ttgataaaga ttatcctcat taatttatac taaaactattg aaacctttga gcatttactt   21390
tttgccagaa ttgttttcaa acttttgatc acagtgattt gtccaaataa tcagttttgg    21450
```

```
tgaagcagca ggattacttt tttttattat ctgtgttcat tgggccacca tgtagatgtg  21510
acaccactgg ccaatttgac agaatttatg acaggaacat actgtgtcaa tacaacctgc  21570
tctccacttt ttatactttt tcattggtta caactaattc aagcaactaa tgacttactt  21630
attctactgg tattgctgat ttgcttttac taattctttt agtattttgg taagtgtttt  21690
ttatatgtaa tgcatattca gagtcacttt gcctttagga tattatactg gaaagtttta  21750
actgttgcat attacatcat tattattact ggatttggtt tataaaagca caataaaaaa  21810
ccagtgtaat gatataaatt ataggcatat gtacattttc ctttagactt agtaaaaaaa  21870
aaatcatgaa cttgataaat ttattcaagt aaaccatgtt atattttaaa ttaaattgga  21930
tatttttcag gga gta tat ggt tta gaa gat gct gtc gtt gaa ata aag     21979
        Gly Val Tyr Gly Leu Glu Asp Ala Val Val Glu Ile Lys
                455                 460                 465 aat tgt aaa aac caa att aaa ata aga gat cga gag att gaa ata tta    22027
Asn Cys Lys Asn Gln Ile Lys Ile Arg Asp Arg Glu Ile Glu Ile Leu
            470                 475                 480 aca aag gaa atc aat aaa ctt gaa ttg aag atc agt gat ttc ctt gat    22075
Thr Lys Glu Ile Asn Lys Leu Glu Leu Lys Ile Ser Asp Phe Leu Asp
        485                 490                 495 gaa aat gag gca ctt aga gag cgt gtg g gtaagccatg ttttaagtta        22123
Glu Asn Glu Ala Leu Arg Glu Arg Val
    500                 505 catagtttgc gcaacctgat ttacaagtct tttttttaa tttaaatttt gtttattatt   22183
atttattaag tagtttaatg cttttttcaa atgcttttat aaaacattta atacaaataa  22243
aagtggagct aacctgattg aagtggaatc agatttatg gggttggagt ggtgggtggg   22303
cagggctgga acattgcttt atttggtcta gcatctcctc agtaatagct gcttgtttaa  22363
aaagatgaaa gttattaat accacatatc agagattaac cttttttttt cccaacaaaa   22423
gtagggtctg tattacccat gtttgtttgc aaaatgctct tgtaacagat gagatattta  22483
aacttcttgc tctgtgttgt gattctcctg cctctgcctc ctgagtagct gggattacag  22543
gtgtgcacca ctatgcccgg ctaattttg tattttggt agagatggga tttcaccatg   22603
ttggctaggc tggtctccaa ctcctgacct aagtgatcc acccgccttg gcctcccaaa   22663
gtgctgggat aataggcatg agccaccgcg cctggcctgt taaaatcttt taaagatttt  22723
taagtacttg attttataa tttagactac ttacgtttta ctttgttcga gtattttaag   22783
gagtaattag taatatagct tgagagttta tatatttatt ttaataaata gcctattagt  22843
taatattact aatttgagtg ttatgatagt gcagactaag ttgctgcttt aaaatgaaaa  22903
taaatatcta aatatcaatt tcattattgc taaatttcat ttaatgcttt cttagttaaa  22963
aatgatcatt tgtaaaaact attatctaaa gaaaagacaa atagacaaat aagtatttta  23023
tacagatata tatgtgtgaa aagtatctaa cttggatccg tagttgtgct aggacccaa   23083 attagacttc tgatcaactt ggactatcag atcacagcct tctgatcaac ttggactatc  23143
agatcacagc caagaatctg gaagttccta aagtgacctt ctggcccgtc taggtagctg  23203
tcatagacat catatttct gtgcttaaaa agctccaaat cttggtttat aatttcattt   23263 aggttttgt taggatttcc attaataatt gtgataaaat tttaacttgg gttacagttt   23323
aaatatctgg aaaattcttt cacagaaagt tacctcattc ttcagtgata ctggctaagt  23383
gaattataac cagttgcttg atggtatatg acatttttgc agcttatttg aatgttttta  23443 agttttaat tatattgctt tctattgtag gc  ctt gaa cca aag aca atg att    23496
                                   Leu Glu Pro Lys Thr Met Ile
                                   510                 515
```

```
gat tta act gaa ttt aga aat agc aaa cac tta aaa cag cag cag tac    23544
Asp Leu Thr Glu Phe Arg Asn Ser Lys His Leu Lys Gln Gln Gln Tyr
            520                 525                 530 aga gct gaa aac cag att ctt ttg aaa gag gcaagtgtgg tagtcagttg       23594
Arg Ala Glu Asn Gln Ile Leu Leu Lys Glu
            535                 540 attattttct ggctgaact atagagaaat actaataatt tatactttgc ag att gaa    23652
                                                        Ile Glu agt cta gag gaa gaa cga ctt gat ctg aaa aaa aaa att cgt caa atg    23700
Ser Leu Glu Glu Glu Arg Leu Asp Leu Lys Lys Lys Ile Arg Gln Met
            545                 550                 555 gct caa gaa aga gga aaa aga agt gca act tca g gtatactcag           23744
Ala Gln Glu Arg Gly Lys Arg Ser Ala Thr Ser
560             565                 570 ttattctaaa cctttaaaaa gaattattga taagtgagtt gtctggatat gaaattattt   23804
gtgtcttagc tgtttttgct gttctattgt ggatctgcta caaatttaat aaatgacaat   23864
aataacctga aggagataag tgagtgtcag tgggttcagt cctgaatctg aaatagacaa   23924
aaacaaaaca aaacaaaata acaaaaacca agcaaacaaa aagaaaaaa accttagaat    23984
tatggaattt ttgaaaagtt ttatagtata gtattttaat ttctagacag caccaatatg   24044
ttgttattaa taataataaa acttagtagt ttttatgtta atatatgtta ctcaacattt   24104
tcccttccct taaggactat gcattgaaaa gcttttcttg taagttatta ttattattat   24164
tattattaat atttgagatg gagtctgtct tgttctattg cccaggctgg agtgcactgg   24224
tgcgatcttg ctcattgcaa cctccgcctc ccgggttcta gtgattcttg tcttcagcc    24284
tcctgagtag ttgagactac aggcgtgagc caccacgcct gacttatttt tgtattttta   24344
gtagaaacag gtttcacca tgttggccca ggctggtctt gaactcctga cctcaagtga    24404
tccatccact ttggctcccc aaagtgctgg aattataggc gtgagccacc atgcctggcc   24464
ttaaattatt cttttctaag tgaaagtaat gttttattga atataaatta acatcttct    24524
tgggtttatt ttacttgagc taaagagaac agttggttaa gttttataat agccattgca   24584
gtgctttttt gtaagaagac cacacagaag gactgtcttt ttcacttgcc ccaaatcccc   24644
aagcacgtat atgagtaata gcagagtggt tcttttagc attatgattt ctataataca    24704
tccaaaactt tctcaagaaa aaacttcatg atttattagt acaataatca gtttactcat   24764
tactcatcat ttatatttac tttatatgtc tttaactgg tgcttattaa gtagcacttt    24824
aatatagaat aggcaaagaa tggtagagaa gatgaaattc aaaaattagg ttctcacatt   24884
attaatagtt cattaaaagt gagctaaatg agaagcttgt attggctatg tagaattttg   24944
gagggatttt ggaaacaatt attctacctt tgcattaaaa cttgattgta ggttttaaga   25004
attaaagtgt tggaatagta ggagggttat tttaatgttt ttagtttgtt aattctctta   25064 tatatag ga  tta acc act gag gac ctg aac cta act gaa aac att tct    25112
            Gly Leu Thr Thr Glu Asp Leu Asn Leu Thr Glu Asn Ile Ser
                            575                 580 caa gga gat aga ata agt gaa aga aaa ttg gat tta ttg agc ctc aaa    25160
Gln Gly Asp Arg Ile Ser Glu Arg Lys Leu Asp Leu Leu Ser Leu Lys
585             590                 595                 600 aat atg agt gaa gca caa tca aag gtaatagtaa agtattgcaa agagagtaaa    25214
Asn Met Ser Glu Ala Gln Ser Lys
            605 ggaaaatatt tttttttttt tttttttttg agacggagtc tcgctctgtc tcccaggctg   25274
gagtgcagtg gcgcgatctc ggctcactgc aagctccgcc tcccgggttc atgccattct   25334
```

```
cctgcctcag cctcccaagt agctgggact acaggcgccc gccaccacgc ccggctaatt    25394
ttttgtattt ttagtagaga cggggtttca ccgttttagc cgggatggtc tcgatcttct    25454
gacctcgtga tccgcccgcc tcggcctccc aaagtgctgg gattacaggc gtgagccacc    25514
gcgcccggcc aggaaaatat ttttattgtg ttttcatttc ttcccccttt atctcattct    25574
tgaacatcta atcttattat tgttgttaaa taagtagagg gaaatatttg cttatttaac    25634
ctgttgattc aaagattgat taatgagaca ttatttactc tgaatacaga ttaggagttc    25694
agataaagca gagctgctgc ataggagatc atcattcaat accccacagt cagatcagaa    25754
tgagacagaa gagaatatga ccataggatc attatcaaga atgttatctg aaattcacca    25814
tagtgtagaa agtggaatgc atccttttgt ccctttaact agactttctt catccatgca    25874
agttaaagag aattcaactc cagaaactat acaataaga gagattttta aagcaccatg    25934
tctgcagtct tcaagaaatc tagaatcgtt agtcagcacc tttagtaggg aaagccatga    25994
agaaataaat gacatatgcc ttttttctga tgactgtatg aagaaggtgt caagaagcca    26054
tcaagcacta gagaagacta gttttgtaca aaaaagcaat tcatctttc atggcttatc    26114 aacagcttca gacataatgc agaagttatc acttaggcaa aaatctgcaa tattttgtca    26174
acaaattcat gaaaatagag ctgacatgga taaatcacaa gtagcaacat tagaagaaga    26234
acaggttcat tcccaagtaa agtatgctga tatcaatttg aaagaagata taataaaaag    26294
tgaagtaccc ttacagacag agatattgaa aaataagctt aaggttaatc ttccagaccc    26354
tgtgtctatt actgcacaat caaaattatc tcagataaat tctcttgaaa atcttataga    26414
acagttacgg agagagctag tatttcttag atctcaggtg agttttctc caaattatat    26474 ttctgtggtt gttctttat gacgtctcta acaaagttct gtaacaatta tagttagaat    26534 attttgttt gcactttaac atcagttata cacattgtac ttttaaaat ctaaaatgca    26594 gtacattgat atgaactcat tgacttgtct aatttattaa attttcttt agaatgaaat    26654 catagcacag gaattcttga tcaaagaagc agagtgtaga aatgcagata tagagcttga    26714
acatcacaga agccaggcag aacaggtagt gtaaaggcag aacattaaaa gagatgattg    26774
tggtactaaa gacaaaaacc gttatatctt tttgcctctt accatggatg ttgggagagg    26834
gagaaagtgg gattaagatc accatctgct ttactgttta gatttagtt tattttatg    26894 attgctgcta tgtcttcata gctcgttttt tttgttttgt tttgttatac ttaattgatc    26954
aaacttttct taacttgaaa attatagact tgtgatattt tgttgaaaaa aatcaatttt    27014
attctctctg cttttttcag aat gaa ttt ctt tca aga gaa cta att gaa aaa    27067
                        Asn Glu Phe Leu Ser Arg Glu Leu Ile Glu Lys
                                610                 615 gaa aga gat tta gaa agg agt agg aca gtg ata gcc aaa ttt cag aat    27115
Glu Arg Asp Leu Glu Arg Ser Arg Thr Val Ile Ala Lys Phe Gln Asn
620             625                 630                 635 aaa t gtaagttaca attatctttt acttttctgt tcttattttt cctatactta    27169
Lys aaatcatggg cctaaaaggg cgttaacaca ttctctgttt tctaatctgc tttactccta    27229
attacctctg tactgtatat acttcagtct gtcactatcc agttgatttg ccttgctgtt    27289
ttcattgtga gagaatgtta ctaatatgaa ttttttgtga gaatatataa ctccttttc    27349 ttgtgtgttc ttcaatcaaa atgaagttag aacaccaaat ttaaaatact ttaatataaa    27409
gcatagttta agttaaggca gaagtatgcc ttatatacgt gtgtatatgc acgtgatata    27469
aataggtctg tcatttaact caactattca cgttggattt atagttgaat tttttgtat    27529
```

```
gtttatttac atttggattt ttccaatgat gtctttggta tatgtgaaat atttgtcatc    27589
tgtatagcat agtgtaaatt gtgaaaaaga tctgatcatc aatgagaaa  actgtgtaat    27649 tacag ta  aaa gaa tta gtt gaa gaa aat aag caa ctt gaa gaa ggt atg   27698
          Leu Lys Glu Leu Val Glu Glu Asn Lys Gln Leu Glu Glu Gly Met
                640                 645                 650 aaa gaa ata ttg caa gca att aag gaa atg cag aaa gat cct gat gtt    27746
Lys Glu Ile Leu Gln Ala Ile Lys Glu Met Gln Lys Asp Pro Asp Val
            655                 660                 665 aaa gga gga gaa aca tct cta att atc cct agc ctt gaa aga cta gtt    27794
Lys Gly Gly Glu Thr Ser Leu Ile Ile Pro Ser Leu Glu Arg Leu Val
        670                 675                 680 aat gtaagttatt ttttcatgt taatgttttt ccctatcac tttagagaga          27847
Asn ttttctgctg tgtacagatc tccatagttt ctgatgagat attttagtc atttgaatca    27907 ttgtttccct gtatgtaaag tgtagttttt cttgagctgc tttcaatact tttcttctac    27967
caattggata attgttatta atctgtcttc aagttcactg acatttttcct ctttatctgt    28027 gttcttttgg ttcaagggtc agcttgagac cttgaggagt ttttacacc gactttggag     28087 ctcgtttttg ctgactcttt tcttattggg attttccttt cacttatccc atggctttgg    28147
gctgtatcct gtggttttct agatgagaaa gatgatagat ctctgcaatt gcaccctgcc    28207
ctatgactaa atctttaaaa atggcaaagt caatctttgc tggtcctgtc ttccgtattt    28267
gaggggtttt ttcccaaaat ctgcttgctt ttgttcattt tctagaacat ctaggtagtt    28327 tttttttcatt cattttttat ttatgggagt gtagatctct taggaactta tgccatcaga   28387
agtattatga aatggcttta ttctaaatgt ttaaagattt actcattgct acaagaaaga   28447
tttagccatc actaatattc tatatatatt taccatatag ggacttgaga atttcacagg   28507
attcagtatc tgtatataaa cttgaataat atacacattt tagattgtta atatttaagt    28567
atatgtcatt tatgttatct gaacatattt agcgtacatt gtcatattat ttcccaaatt    28627
tgtgcttgat ttcaaatggg aaaaaaattc ttattattta ttgaattgtt tttttaaaaa    28687
aatcatgatt aatcagtaat tggatacttt ttaaaataac actataattg ttaacagaga   28747
atgagagtga tactggtatg ttaaaaactt cctgaggcaa gaaaataatt tgattcccat    28807
tatatctttc tcatactgac tttccttctc tgattggtga ttttgttttg cctctgccac    28867
tttgaatgtc taaatgatt ctttatgctt tttttatgtg aacatctttt gtccgtgatg    28927
atgcccacta ctgatactgt gtcccagatc aaacttaatt ttccaagggc agctctactt    28987
agtgaccaaa tgaaaacaca gtgaatagcc caagaaatcc taacttctat ttatgttgac    29047
aatctctgga ccttcctgaa gccactgttt gcatagactt catttacttt tatccgggat    29107
tgtcattgtt ttttcagatt cataggccct atctgaaatt cacaaatcac ctagcaatac    29167
ttctctaaga aatcttcaga atccatgaca atttagacca gacaatgctg gattatgcac    29227
ttcagttcac tttttgttac tacaaggtat ttttcagtgc ccccaacagc tatcttaact    29287
cattctcatt ttaccaaagt ccatgtagac acggcactat tcctcaatga gacaactaac    29347
tagaccacct tgttgtcagt cagagtacct tcctctacct acttttatct tcctttatatc    29407 ctctttgagt tagtataagt tattactctg catgacctgc tctaatctcc ttcagggggaa   29467 ggcttttaca aatctactac ctagagttaa accccagatc accttcctga gtaggagatt    29527
gcatttggtt ctattcattt taccttattt ggcttctacc ttcacttttt aagacttact    29587
ttgcctttaa cagttttttc catacagttc atctaaagtc caaatatatt tattagatgt    29647
```

```
gtgcattgtg tgtatatact tagatatgcc actgttggag atttcgggcc agtgatgcca    29707
ctctgataat attttaatat ttgacatatt attttgctt actcattatt cttagataat    29767
atcatgttat gataccttgc ctttattttt atttatgctt caactatgtg gagaggaagc    29827
actgaaaaat tcacttaatt gaatgttgta ttgatcaatt gttcaatatt gtattccatt    29887
cctttgcgca tgctttgaat gcaggtgcta tataatttca gagaaaaata cctcattttg    29947
actgtacaaa aacccatgt agggagcaga gctcacattg ttttcccctt ttagagacaa     30007
gaaaactaag atacagagaa tttaagtcac ttgcccagct gttaagtgac tgattaaaat    30067
ttgaaccctg gtcatcttat tcccgtctgg ttgttttct agtctaccag tctattaaga     30127
ttagctaggt gttttttaat tgttttaatg aagtaattac tatgcttggt aatgtaaatg    30187
aaagttttat agattcataa ataagaattt gaattggcat actttattat catgcttggc    30247
aatgaaaata ggaaaatgct taaatgtcca ttttatttaa agacagactg ttttttacta    30307
tgattttact gtttttctcc acatttctaa tatataatat aaatttgcta g gct ata     30364
                                                          Ala Ile
                                                             685 gaa tca aag aat gca gaa gga atc ttt gat gcg agt ctg cat ttg aaa      30412
Glu Ser Lys Asn Ala Glu Gly Ile Phe Asp Ala Ser Leu His Leu Lys
        690                 695                 700 gcc caa gtt gat cag ctt acc gga aga aat gaa gaa tta aga cag gag      30460
Ala Gln Val Asp Gln Leu Thr Gly Arg Asn Glu Glu Leu Arg Gln Glu
    705                 710                 715 ctc agg gaa tct cgg aaa gag gct ata aat tat tca cag cag ttg gca      30508
Leu Arg Glu Ser Arg Lys Glu Ala Ile Asn Tyr Ser Gln Gln Leu Ala
720                 725                 730 aaa gct aat tta aag gtgagaattt tattaaataa agaaaatgc taaacataag       30563
Lys Ala Asn Leu Lys
735 aatgtagatt taataggaaa ttttttaattt tttaaaaaga atgctttatg agaaaatgcc   30623 ccttgaatta attctttcaa tattaagaaa ctggatttct cttataaaat tataagtgga    30683 aaataagtgc cttataagat tgaaaagaat acaaaaattc taaatctcat acctaggcat    30743 ttctaagcag aaactgaagt atggttgagg taaaattcct ggcagggcat tcacatatct    30803 gtcaatttgt cttctttgg gtgtaagagt tgtgattctc attgctggat ttttttttcc     30863 ag ata gac cat ctt gaa aaa gaa act agt ctt tta cga caa tca gaa       30910
   Ile Asp His Leu Glu Lys Glu Thr Ser Leu Leu Arg Gln Ser Glu
       740                 745                 750 gga tca aat gtt gtt ttt aaa gga att gac tta cct gat ggg ata gca      30958
Gly Ser Asn Val Val Phe Lys Gly Ile Asp Leu Pro Asp Gly Ile Ala
755                 760                 765                 770 cca tct agt gcc agt atc att aat tct cag aat gaa tat tta ata cat      31006
Pro Ser Ser Ala Ser Ile Ile Asn Ser Gln Asn Glu Tyr Leu Ile His
            775                 780                 785 ttg tta cag gtattgaaaa ttttgttaca ggtattgaaa attttacatg              31055
Leu Leu Gln tgaataacaa aaatcattgg tagtatgttt ctttatgttt ttattttat tttactttat     31115 tttaatttt ccatcaccaa agcatgcaga tagtactttt ctcaatattt agtcttcatg     31175
tattcctgag ttctcaaaat agtaacagtg aaatatattt tttatggatt ttgatgttag    31235
atggattata aataaaagca atttatacca ttcattccat tcatctgcat gagcagcatg    31295
ttcatacatc ttgttcgcac acctgtcatt catgtgaaat atatggttca caagcagaac    31355
aacaagcagc tattataaag cagtgttaag taaatgagca cttttatttc ttgctgggtg    31415
```

```
gaaaacaaaa gaataaagtc tgtcaaggct ttttagtgtc atgatagaat tgttcccctt    31475
tttgcattca caagtaaaaa ctactttttt tttgagacag agcctcactc tgtcactcag    31535
gctggagtgc agttgcgcta tcttggctca ctgcaacttc cacctcctga gtttaagtga    31595
ttctcatgcc tcagcctcct gagtagctgg gactacaggc atgcatccct ggctaatttt    31655 tgtattttt tttagtagag atggtgtgtc gtcatattgg ccaggctggt ctcaaactcc    31715
tggtctcaag tgattcgcct gccttggcct cccaaggtgc tagggttaca gacgtgagcc    31775
actgcacaca gccataagca aaaacttcta aaccaaatta ttcttcatct ttgtcttccc    31835
tttacgcaat aaaatgttaa tctaccacca aagaggaaag ggtactctac tatactacct    31895
gccctgggtt tctcagtttt gctgtctata taatggtcgt tatgaatgtc ctaatgacag    31955
atccttttca ttattttatt tgaaatttga ctatctataa catcacatac attataaata    32015
taattacaaa tatatgttca gaatcaatga aaatatattt ttgattatat gggccactat    32075
ttctctctgc taggtgatcc atttgtgagt atacttgagt tataattatt aagtactcat    32135
ttttattttg gaaattacag taattcatct ttttctcaat attgggatttt ttattattat    32195 tttatgttgt ctaaggacag ccttaactac ttattagaat attgctttgt atgtgatatt    32255
attattttta aatgtataat tttaacatta ttatttctct tatttacctg aggtatagga    32315
acactatcag caaatattgg tagtatggca ttgtcgtatt ttttgagata aaattcatga    32375
tttttaatct ttgtataaga aatatatcag aagtttgtag tagattagag agtaccaact    32435
gggagtctga aaagctgtcc aaagtggcaa acaggtact tagactctca atcctaaggc    32495
tgtatagagc tataaacgtg gcaagacctt tggagtcaga cagacccaaa ctcaaatgtt    32555
ggatccatgt atatggaaag cacctgacaa caagcctagc atatgtactt ggtaaaaatg    32615
attgccaagt gtagtgttaa tgagttttg gatattgagt aagttattta aatttcaatt    32675
tcatctttaa aatgaaataa ttggaaagga taatttgagt gagggtatga aattatgtgt    32735
tcataagaga gggtatgtgg ccgagtgact agaggcgagt ttataactat tctatctaat    32795
aaaactttgt aatctggtaa tttgtgtgct aaaaataact ttacctgttg tatagtactc    32855 ttttttatg ccttaaacta aagtgttcaa aatatcatgg aaaaatgatc tgtgttgctt    32915 acagattgg tgacttttaa cttctcctata atgttgtcag aatatgaatt tatactttca    32975
aattcagcat ttattctatt gtgttttttt ttgcattctt atttctaaac cacttttcag    33035 gaa cta gaa aat aaa gaa aaa aag tta aag aat tta gaa gat tct ctt       33083
Glu Leu Glu Asn Lys Glu Lys Lys Leu Lys Asn Leu Glu Asp Ser Leu
790             795                 800                 805 gaa gat tac aac aga aaa ttt gct gta att cgt cat caa caa agt ttg       33131
Glu Asp Tyr Asn Arg Lys Phe Ala Val Ile Arg His Gln Gln Ser Leu
            810                 815                 820 ttg tat aaa gaa tac cta ag  gtataggtat tagcaaaact ataaatataa          33181
Leu Tyr Lys Glu Tyr Leu Ser
            825 ttgcagtata ttcttgttaa ttgtgaaagt aacgtaagaa taatttatgt tttgttcttc    33241 ccttcttctt cttcctttgc aattgtattt ttttttactc tggtaactac tgttaggaac    33301 ttatttatgg agacagtgta gcttaatgat tacattaagc ctgggattat cctgcctggg    33361 tttgagtcat ttaacgtttg ctttttgtaa gagcttgagc aagtcatctt acctatctgt    33421 gtctcagttt ccttatctgt aagttacttt gtaagtaata ccctttcat aggattattg    33481 taaaacgtaa atgaattatt agatgaaaat gctcggacta gtgtgtggca catatgaaca    33541
```

```
gtttgtaaat gttagctgtt gttagcatca ttcatcatca tcacaatcat cattgttcat   33601
atatgtttat agggaactaa catatttctc cttatttctg tcatctcatc taaatcaata   33661
gaatgatttc cttaatagga attagaatac ctaatcaaag gtgatttaaa cactaagaat   33721
aattattatc tgacctaacc agaaccacaa agctagttgt agggcaggtc atatttgaag   33781
gttgttgtta tcgcctatga tggttgtaaa atagctgcat gaattcaaga aagatgatgt   33841
gcccattgaa gaagaggagc attttttttct acatagcttt tattttttaaa taaacatttt   33901 tttctggtga tacctggcag acattgactc cgatctcatt tgctagaatt ggatcacatg   33961
tccaagtctg aaccattcag ttgcaaagag aatgataccg ctatactggg tttatgccaa   34021
gaacattaca catgtttgtg gaatgctcat gtgtagacaa cagtgtctta cacaacttca   34081
aaaaaataat ttatatataa atatgtttta aattacttttt taaattcaca agaatttatg   34141
gtatacaaca tggtgttcta tatatgtata tactatgcta tacaacatgg tgttctatat   34201
atgtatatac tatgctatac aacatggtgt tctatatatg tatatactgt ggaatggcta   34261
aatcaagcta cttaacatat gtattacctc gcatactttt tttttttttt ccttgagaca   34321
gagtcttgct ctgtcaccca ggctggagtg cagtggcgct atcttggctc actgcaacct   34381
ctgcctcctg ggtccaagtt attttcttgc ctcagcctcc caagtagctg agattacagg   34441
catgtgccac cacgcctggc taattttttgt attttttggta aagacggagt tttgccatat   34501
tgtccacgct agtctcaaaa ttcctagcct caagcaatct gcccaccttg gcctcccaaa   34561
gtgctgggat tacagcatac ttcttcttat ttttttttttt ttttgcacta agaacactta   34621
aaatttactc tcttagcaat tttaaagtat ataatatact gttattaact ttggtcacta   34681
ttttaattag acttaagatg tgtttgtatt caaattattt tgtaagcatt taacacccaa   34741
atttgagagt ggggtcagaa tgttggaatt tgatttctag aattagtata gggtattatt   34801
ttcctacttt ttttctgtgt tcaataaaat gtttataaga ttcagcttca attatattat   34861
aacccattta gtggtgaatc agggaagaat gaaaataatt tgataacttt gttgccttgc   34921
atttatttaa aaaatttttta attctaggct aaacccttttt taaatgaaag tttaacttct   34981 tgtgtttttca gatactgaat agctatgata cctcttgtgt tgagaaaact ttaaatttgc   35041
ataatctgaa gttatctttt cttataaaca ttttattagg tttacagtat tgtcttttg   35101 ttttgttttg tttttag t gaa aag gag acc tgg aaa aca gaa tct aaa aca   35152
              Glu Lys Glu Thr Trp Lys Thr Glu Ser Lys Thr
              830                  835 ata aaa gag gaa aag aga aaa ctt gag gat caa gtc caa caa gat gct   35200
Ile Lys Glu Glu Lys Arg Lys Leu Glu Asp Gln Val Gln Gln Asp Ala
840             845                 850                 855 ata aaa gta aaa gaa tat aat gtaagtaaaa cattttttaac attagtatgc       35251
Ile Lys Val Lys Glu Tyr Asn
                860 aatattgtac aaagtaggat agctagattc aacaagtaat atggatgtgt ctttgtgcag   35311 aat ttg ctc aat gct ctt cag atg gat tcg gat gaa atg aaa aaa ata   35359
Asn Leu Leu Asn Ala Leu Gln Met Asp Ser Asp Glu Met Lys Lys Ile
        865                 870                 875 ctt gca gaa aat agt agg aaa att act gtt ttg caa gtg aat gaa aaa   35407
Leu Ala Glu Asn Ser Arg Lys Ile Thr Val Leu Gln Val Asn Glu Lys
880                 885                 890 tca ctt ata agg caa tat aca acc tta gta gaa ttg gag cga caa ctt   35455
Ser Leu Ile Arg Gln Tyr Thr Thr Leu Val Glu Leu Glu Arg Gln Leu
895                 900                 905                 910 aga aaa gaa aat gag aag caa aag aat gaa ttg ttg tca atg gag gct   35503
```

```
Arg Lys Glu Asn Glu Lys Gln Lys Asn Glu Leu Leu Ser Met Glu Ala
            915                 920                 925 gaa gtt tgt gaa aaa att ggg tgt ttg caa aga ttt aag gtacatctga      35552
Glu Val Cys Glu Lys Ile Gly Cys Leu Gln Arg Phe Lys
            930                 935 ttcttatttt gcttttctg  actatgaaaa atttcaaata tgcagaagat aggatggtat   35612
caataatgct catcacctga attaatagtt aacatttatt aacattttgt cataattgct   35672
tcttctgatt tttgtgggat gtttgaattg cagacattcc tccectaaat atttaatgta   35732 cccttttgaa aaaggctttt ttctttaact aaccatagta actttattat acctaacaaa   35792
atgacagtaa ttttctaata tcgcctaata ccctgattat agtcacattt tttacatttt   35852
ttgatcaaag aataagcatt tggatgttac atctcataaa tcttttaat  atagaatccc   35912 cttggttttc ttttctcca  aaaaatgttt gaagatgtat ctaactttg  tgtgtgtgtc   35972 attttacttg ttcctgtgtc ccttgtatta ctaaagtta  ggtcagaacc ctaagttaca   36032
ttcaggttta acattttttg gcaagaatac ttcataagta gtgttctata ctttatattg   36092
catcacttca agagtatctg gttgttccat gttttgtaat tgattactct gttaaggaaa   36152
agacaagcag accaagtatg gtggctcatg cctataattc caacattttg gaaggcccag   36212
gcaggaaaat ttcctgagcc cagaccagcc taggcaatat agtgagactc cgtctctaca   36272
aaaaatgttt ttttttttgt ttgtttgttt taattagct  tggtgtagtg gcacatgctt   36332
gtaatcccag ctacctggga cattgaggtg ggaggatcgc ttgagcccag gaagttgggg   36392
gctgcagtga gctgtgatca tgtgccactg atctccagcc tatgtgcctg tataacagag   36452
cgagtctctc tcttaaaaga aaaaagaag  aagaagaaga agaaaagata accatatacc   36512
tccattatta agcaatttag ctaactggtg atattttggt accatacaaa taacaaatta   36572
tttgtcagtc ctaatgattt tagcatctgc tgatgattgt tgcctaaccc aattattaaa   36632
agttgcaaac atcataattt tctagttata ttatgcactt acatttatta acagacatgc   36692
ttttgtaaaa taaatagcgt ttcctcatta gcccaggcta tttgtttatc ttgaagttta   36752
gctcctacta caaaggcaag ataaatgctt ttctctttaa ttaccagttt tcagaataca   36812
cacttggtgt actctgcact acctgctttt tttgtcccct ccgctttctc ttttttaagt   36872
atcagattag actcacagat tttaaatat  tccatgtgtt ttagttggag tcatattctt   36932
ttgtctcaac tttagccaaa gagagtcctt taaagttgac tcttatattg tcttgacaaa   36992
aattcattag tcttttgaac gaagcctcaa agcttgactt gttttctagc ataagatgtc   37052
ttagacttac ctacatactt catgcccata cttggaataa accatttctt taaagagccc   37112
aggttccttt tagtggggaa ggcatttaga taccaaaaac tggccactgg gcatcattgc   37172
tctcagagta tcattgccac tagtctctca gtagacaagt tagaaaaata tgtatatatt   37232
taaaccatga gttcatattg ttatttccag tttaattata acattatggg gtaagtaaat   37292
agtatcggat ttttactaag cttctttgat tttgcacttg tatttttttc ttacatagaa   37352
aacctttatt attaacatta aaatatttgt tttatcctac aatatacata caataatttg   37412
aaaaataata cttgaattga tattaatagt aacaacaaca gcactgctgc caaacatagt   37472
ttaaagtttt atttcaggtc ttattttctt cagaatatat cttgctgaga atgtataggc   37532
aaagtattct acacttactt gaaataattg tcttcatgcg gttatgttat acatttgata   37592
tatagttagg ctcattgtt  ttttcattt  ttattttag  ggattttttt cctttattga   37652
attttaatat atacaatatt tatatatgca aaatatttaa tcagagaaat cttaattctg   37712
```

```
gtcttacgcc tttcatatta ttctgctcca ccctctgtag gtaacttatt atctttctca    37772
tgtttccttt ttggaaacat aaacaaagac aagacaggtt acatgacatg tatacccttc    37832
tgcacctagt tttatacctt accttgtagt ttatttttaa gcatgtaaat gttcaatgtt    37892
catgactaaa tttggacagg atcataggaa cacagaattc aaagtgaaat taaaatgggc    37952
ttgggttctt tactttccac tttaaaggtt gtaatgggtg atgtcaggct aataaaccta    38012
ttttcagctt gatctaaagc ttaatactga gcatcaagaa attctttaat aaatataagt    38072
gatatttatt cagacatgta ataaggaaat gttcatgtct tattttgtg ttagattttt      38132
ttagaatcta cttttgttag agttttataa atacagttag tgtttgagat agaaagagaa    38192
aagaattagt tttcttcctc ttctacctgc tcatgaactt gattttttc tcccaacaat      38252
tgaagagcca agaaaaaggg agattcttaa gagatgggaa atagaatctc atctacccct    38312
gtttccccca gaacagtgaa actgaatctt aagggtaaga tagaatagtg tgtacttaac    38372
ttagatggag aagaaaggct gccaaaatga gatctgaagc gctattacaa atatttccat    38432
cgttactgta cttcagaatg aattacaacc gtaagttttt ttacttcctc attcataaat    38492
ttgattattc cttataccac ttctcagctt tcatcattct ttattgtact tttctatgta    38552
atgtttgcct attatacagc aacttaagag aactgtaagt ttggacattt cattttggtg    38612
ttgataatag aatatctttg aatagttcta tagttgatga gtagaaccat gaaccaagta    38672
acttaaagtc cttgatgtta tttattacag agaactataa tagaagctct cccgctaatg    38732
tttccatcat gtgtacaaaa agttttcttg ttattaaagc tagtccgttt aacttacaat    38792
aagcataaat agctaagctg tgaaagttac ctgtgataat gctaattttc ccatttatta    38852
aaaggcaagt tgttttccga tcataagaaa tttagaaaag ccatccaaag ataaattccg    38912
agtgatatat tcctgctgtt tgttatgttt tctcaaatta attgagtttt attttacaat    38972
gacaggagtt attaaagtat tttatttta ttatgattaa gattttcaaa gtaacatttc      39032
ttatatgaaa gaaattatgt taatgcatgt ttttcttaca tgggaaatca tatattttaa    39092
aaatgatttt aaaattcgtt ttactttaag ttgtattatc tttctcaaaa gtggctagtg    39152
cttgaccaga aaaaagaca ccagcataac tcagtgtatc tttatttaca tag gaa         39208
                                                                Glu
                                                                940 atg gcc att ttc aag att gca gct ctc caa aaa gtt gta gat aat agt    39256
Met Ala Ile Phe Lys Ile Ala Ala Leu Gln Lys Val Val Asp Asn Ser
            945                 950                 955 gtt tct ttg tct gaa cta gaa ctg gct aat aaa cag tac aat gaa ctg    39304
Val Ser Leu Ser Glu Leu Glu Leu Ala Asn Lys Gln Tyr Asn Glu Leu
        960                 965                 970 act gct aag tac agg gac atc ttg caa aaa gat aat atg ctt gtt caa    39352
Thr Ala Lys Tyr Arg Asp Ile Leu Gln Lys Asp Asn Met Leu Val Gln
    975                 980                 985 aga aca agt aac ttg gaa cac ctg gag gtaagtttgt gtgattcttg           39399
Arg Thr Ser Asn Leu Glu His Leu Glu
    990                 995 aaccttgtga aattagccat ttttcttcaa tattttgtg tttgggggga tttggcagat     39459
tttaattaaa gtttgcctgc atttatataa atttaacaga gatataatta tccatattat    39519
tcattcagtt tagttataaa tattttgttc ccacataaca cacacacaca cacacaatat    39579
attatctatt tatagtggct gaatgacttc tgaatgatta tctagatcat tctcccttagg   39639
tcacttgcat gatttagctg aatcaaacct cttttaacca gacatctaag agaaaaagga    39699
gcatgaaaca ggtagaatat tgtaatcaaa ggagggaagc actcattaag tgcccatccc    39759
```

```
tttctcttac ccctgtaccc agaacaaact attctcccat ggtccctggc ttttgttcct    39819
tggaatggat gtagccaaca gtagctgaaa tattaagggc tcttcctgga ccatggatgc    39879
actctgtaaa ttctcatcat tttttattgt agaataaatg tagaattta atgtagaata    39939 aatttattta atgtagaata aaaaataaaa aaactgagag agaatatcat aagttacaat    39999
ctgtgaatat ggaccagacc ctttgtagtt atcttacagc cacttgaact ctatacctt     40059 tactgaggac agaacaagct cctgatttgt tcatcttcct catcagaaat agaggcttat    40119 ggatttgga ttattcttat ctaagatcct ttcacaggag tagaataaga tctaattcta    40179
ttagctcaaa agcttttgct ggctcataga gacacattca gtaaatgaaa acgttgttct    40239
gagtagcttt caggattcct actaaattat gagtcatgtt tatcaatatt atttagaagt    40299
aatcataatc agtttgcttt ctgctgcttt tgccaaagag aggtgattat gttactttt     40359 atagaaaatt atgcctattt agtgtggtga taatttattt ttttccattc tccatgtcct    40419
ctgtcctatc ctctccagca ttagaaagtc ctaggcaaga gacatcttgt ggataatgta    40479
tcaatgagtg atgtttaacg ttatcatttt cccaaagagt attttcatc tttcctaaag     40539 attttttttt ttttttttg agatggagtt tcattctgtc acccaggctg agtgcagtgg     40599
cacgatctcg gcttaacgct tactgcatcc tctgcctccc agattcaagc agttctcctg    40659
cctcagcctc tgagtagctg ggattacagg tgtgcaccac cacaccagct aattttttt     40719 tttttttttt tttttttgag gcagagtctc gctctgtcac ccaggctgga gtgcagtggc    40779
gccatcttgg ctcactgcaa gctccacctc ccgggttcag gccgttctcc tgcctcagcc    40839
tcctgagtag ctggtaccac aggcacccac catcatgccc ggctaatttt ttgtattttt    40899
agtagagatg gggtttcacc ttgttagcca ggatggtgtc gatctcctga actcgtgatc    40959
cacccgcctc ggcctcctaa agtgctggga ttacagatgt gagccaccgc acctggcccc    41019
agttgtaatt gtgaatatct cataccatcc cctattggca gtgtcttagt tttattttt    41079 attatcttta ttgtggcagc cattattcct gtctctatct ccagtcttac atcctcctta    41139
ctgccacaag aatgatcatt ctaaacatga atcctaccct gtgactccca tgtgactccc    41199
cgccttaaaa actgtcaaaa gctaccggtt acctgaaggg taaaagtcaa gtcccctact    41259
tacctcatgt catctagagc aagagatgaa ctagctgagt tttctgacca cagtgttctt    41319
tcttatgtat gttcttttgt acgtgctctt ttctatatat agggaaccat ttctctcttc    41379
cagttgtttt gctcagtgaa tttctattcc tgtttcaaaa cttgttcagg cattacccttt    41439 tttttcttaa gcatacttt tttaatggaa caaagtcact cctgtctaca ctagttctgc      41499
atcttataca taggttttgt acatagtaca tatttatc acatcaaatt atatgtgttt      41559
acatatctgt cttccttaat ggaatataag tcttttgata taaggaacta tttaatttgt     41619
ttctgtgtgt tgagtatctc ctgtttggca cagagttcaa gctaatacat gagagtgatt    41679
agtggtggag agccacagtg catgtggtgt caaatatggt gcttaggaaa ttattgttgc    41739
tttttgagag gtaaaggttc atgagactag aggtcacgaa aatcagattt catgtgtgaa    41799
gaatggaata gataataagg aaatacaaaa actggatggg taataaagca aaagaaaaac    41859
ttgaaatttg atagtagaag aaaaaagaaa tagatgtaga ttgaggtaga atcaagaaga    41919
ggattctttt tttgttgttt ttttttttga aacagagtct cactgtgttg cccaggctgg    41979
agtgcagtgg agtgatcttg gcttactgca acctctgcct cccaggttca agcgattctt    42039
ctgcttcagt ctcccgagta gctggaatta caggtgccca ccagcacggc cggctaattt     42099
```

```
agtagagaca gggttttgcc atgttggccg ggctggtctc aaactttgga tctcaggtaa    42159
tccgccagcc tcaacttccc aaagtgctgg gattacaggc atgagccact gtgcccagcc    42219
tgtttttttt tttttaaagg agaccagtga agtttcagga ggagggaaag aaaatttaga    42279
gttactaggg agagagtgat gaagataaga gatgaaagtg gtaataaggg aaatagcaaa    42339
atatcagggt aggtgggaga aaaagagatt tgtaacaaac aataggatta tcctgtgaaa    42399
aaggatgaaa ggaagaaaaa aatggataga aagatattta aaacaccctc agcctcctgt    42459
tttccctcct gtgtattcat agtatataaa actataatta tgtactttac ttaaaaaata    42519
tattattatt accttatcgt gcttatttaa tcatagcatg tcctcttttt agtctcatta    42579
ccctgtttgt attattcttc ataacactta atacctgaca ttgtattata tattggctta    42639
ttttccaggt actccactca aatataagtt ctaggatata atttatttat cactgaaatc    42699
cattgcttag agtacctggc atgtagtaaa taggcattct gttttttcaa ataaaaaata    42759
aaggaactta agatatatat ttatgttata tcgccagcct ttttcctcac agctctattc    42819
tgttgtacag aattacctac tttacaattc ctgtgtttca aggggatctc aaatttaacg    42879
tgtccacaat gaactcctga tttctgtttc tctcctagtc attcttattt caatatatgt    42939
tcagttacct aaccagctag tcaaggcaga tactttagag ttattctgta gtcattcttt    42999
ttccctacca ttttgttttt ccaaatgtaa tttatgtgtg tcttcttcat cctcgcagct    43059
ctaacccttg tccaaaccag catcatcact catctggagt tccacaatgt ctttctggct    43119
agtttccctg atttctctat tgaccccttt attctccaca gtgcagccag aatgattgtt    43179
taaaacttcc tccttaaaat ctttaaattg ttttcttttta tacgttaagt taaattccag    43239
ttccttgtct tggcatgcca tgccctgcct ggtgtggccc ctgatggtct ctccaacttc    43299
atgttttact actattgact cttatttttg cttactctgc ttgggtgctc cagtcctcca    43359
aatcatttcc tgctccaatc atttcaatca ttttttcctc tcagatctta tagtattcca    43419
aatgctttct tcctttggag catctgggtt tactaataaa tacttcgtac ctcacagttc    43479
agcttaaata tcaattattt ggtggttaag acatccttca accgctctat ctaaatgttc    43539 cttttctatta ttcactggct cagtactctg tttttatttt cttctaaat gtcaacttttt    43599 tttttttga gtcagggtct cactgttgcc caggctcgag tgcagttgca caatcatagc    43659
tcattgcagc cttgccctcc tgggatcaag taattctccc acctcagcct ccaaaatagc    43719
tgggattaca ggtatgcatc accatgctca gctaattttt tgtgtttttt tgtagagatg    43779
aggtctcact tgttgcccca ggctggtctc aaactcctgg actcaagtga ttctcccacc    43839
tcagcctccc aaagtgctgg ggttacaggt gtgagccact gcacctggtc gatactgact    43899 ttttttttttt tttgagatgg agttttgctc tgttgcccag gctagagcgc agtggtgtga    43959
tctcagctca ctgcaacctc cacctcccag gttaaaggga ttcttctgcc tcagtctcct    44019
gagtagctgg gattacaggc aagtgccatc atgactggct aattttttgta tttttagcac    44079 tatgtttagt actgtgttgg ccaggcttgt ctcgaactcc tgacctcaag tgatccaccc    44139
acctcagcct cccaaagtgc tgggattaca ggtgtgagcc accgtaatcg ccaacattg    44199 acatttttag tagactttt gtttgtttac ttgcttatta tctgctgcct tccacactct    44259
ggcgaaatcc tgccacccac ccacacacac ataggcactg aatgggcaga actctgaagg    44319
ccagaatttt atatttcttt tcactgtaaa catcatcatc tgtcactgat ggcacactag    44379
gatgctcagc aactgtgtgc atgaaggaag taagcactag tttgtgaagg ctgcaaaact    44439
cttgagtatt ctaagagttt tggccaaaat gaatgtacag ctttagtggc agaagctaat    44499
```

```
actcagaaat tgaggccgta tattggataa cacaggattt ggatgattat tttaaaataa    44559
tattttacat tgtatatatg tgtgtgtgtg tgtgtgtgtg tgtgtgtatg tgtgtgtgtg    44619
tgtatatata tatgtatgta tgtgtattag tccgttctca tgctgctatg aagaaatacc    44679
tgagactggg taatttataa aggaaagagg tttaattgac tcacagttcc acagagctgg    44739
ggaggcctca gaaaacttaa cagttatggc agaaggggaa gcaaacacat ttttcttcac    44799
atggtggccg gaattagaag aatgtgagcc gagcaaaggg gaaagcccct tataaaacca    44859
tcagacatcg tgagaactta ctattatgag aatagcgtgg gggaaaccac ccccacgatt    44919
caattacctc ccaccaaatc cctcccatga catatgagga ttatgggaac tatgattcaa    44979
gatgagattt gggtagggac acagccaaac catatcagta tgtatatgta tacaagtatt    45039
atatatatat gtatgtgttt gtatgcatac atgtattata tatggaggaa attctaatttt   45099 tgtaaaaaac tggattgtga gttttaagga gatgttatat aaagttaaga caatgtcatt    45159
ttgtggtatt ggtctgaatt acaatgtagt ttcttagtga tattttttcct ttattcag     45217
```

| tgt | gaa | aac | atc | tcc | tta | aaa | gaa | caa | gtg | gag | tct | ata | aat | aaa | 45262 |
|-----|-----|-----|-----|-----|-----|-----|-----|-----|-----|-----|-----|-----|-----|-----|-------|
| Cys | Glu | Asn | Ile | Ser | Leu | Lys | Glu | Gln | Val | Glu | Ser | Ile | Asn | Lys |       |
|     |     |     | 1000 |     |     |     |     | 1005 |     |     |     |     | 1010 |     |       |

| gaa | ctg | gag | att | acc | aag | gaa | aaa | ctt | cac | act | att | gaa | caa | gcc | 45307 |
|-----|-----|-----|-----|-----|-----|-----|-----|-----|-----|-----|-----|-----|-----|-----|-------|
| Glu | Leu | Glu | Ile | Thr | Lys | Glu | Lys | Leu | His | Thr | Ile | Glu | Gln | Ala |       |
|     |     | 1015 |     |     |     |     | 1020 |     |     |     |     | 1025 |     |     |       |

| tgg | gaa | cag | gaa | act | aaa | tta | g gtaagtttta tgactctgat aatataaaat | 45359 |
|-----|-----|-----|-----|-----|-----|-----|---------------------------------|-------|
| Trp | Glu | Gln | Glu | Thr | Lys | Leu |                                 |       |
|     |     | 1030 |     |     |     |     |                                 |       |

```
gattaacatc taataatgaa tatttcttat ttaaagttcc ttttttatgc tagattaaaa    45419
ggaagtattt tgactaaaaa aagaaagaac tttctgccta ataatttaac ttaggcagat    45479
gaataatcct gtacttaacc ccaccaaagt ttagttttca gtccttaagt tagatttgtt    45539
tctaatgaaa tcatatatgt taaaaattta tgactaagta ttagctactt tgaaccgttt    45599
aacaattaaa actgatgata ttttattaat ggtattatga gttctttcac tgagtgcaag    45659
ttatattagt tatatatcac ttgatatttt taaattaaaa gataccagga aacagcaaag    45719
aaaatgtgaa aagaagttgt atttctcata gttttactac tatattactg tatattttg     45779 ctcctatatg cttacatatt ttatatattt taaattatta taaacatggt tttatactgt    45839
atttagatag taatatcaaa aatatttta tggccggcgc agtggctcac acctgtaatt     45899
ccagcacttg ggaggctgag gagagcagat cccctggggt caggagttcg agaccagcct    45959
ggccaacatg gcaaaacccc atctctacta aaagtacaaa aattagccag gcgtggtggc    46019
agttgcctgt aattccatct actcaggagg ctgaggcagg agaattgctt gaacctagga    46079
gtcagaggtt gcagtgagcc aagatcatac cacagcactc cagcctaggc gataagagtg    46139
agactccgtc tcaaaaaaaa aaaaaattt gttttattca tcatacttat aaatacttat     46199
acaatagcct aatgtgtttg agtgattaaa tcactagctt tttatatttt tgctattgct    46259
tatagtgcca cagtgaacat tttcatgtat atctaacaga gatattactg tctcagaagg    46319
tattgaaatc tttgttgctc tcattagagt tttccatatt aattttttcaa acagttatat    46379 agtttataag attttcataa ttttatctca tatattgtgc ttcataattt tcaaataaat    46439
ttgctgcttt cgataatgta ttttcatgta tttgtttcct agacgttaga gctattcaag    46499 gttttttatta ctaaatagag ctgttctctt aaattggtaa tgagatactt ggtttagaga   46559
agcctaacac tgggaaatct tacataagct acttttagaa atgtaatttt tagctcaata    46619
```

```
agagattaaa tatgaattga cttttgtgta gtatttgcat ggaagaaggt accatttaaa   46679
tgaagacatg agagtattac gtacaatttt agtaggttct ttttatttta tcatctttat   46739
ttttaataaa tgctgaattc cctacagaaa ttctttaatt tttacatatc ttgatctctt   46799
tcatatatgg atttatatca ccgaagtttt aagagtgttt ccctattccc tgttgccctt   46859
atatctttgt ttaaaaatgt cacatcatta gctttttttc atctaggaat ttgttagtgt   46919
tgggctgttg tgctctaccc tctctttaag aaaactccaa acccaaaaac atacaagatg   46979
gctagtctgc ttcagccttt gtgatgtgct tttctcttct aatcagagtt tagcacaata   47039
cagaatggag aaggactcct ttatatattg gtatttattg cagtattttt ctacatggtg   47099
cctaaggtta cttgaatgag tctttattcc ataatgaact gatttactaa tgcttttagc   47159
acctgttagt gatccattat tgttagttac ttgattactg cttgccacag ctattctaaa   47219
ataatacatt ttaaagataa atacagaaca taatgaagta cttttttaaaa ctgagataga   47279 gaccaatttt tttttcagga aatgtatatt actttgagaa aactcagtta taaaacttga   47339
acttatgaag ctggaaaaac aggaggggggc attattggta ttgtaaaagg ctgtttacaa   47399
agtgagttgc tgcttagttc ctttaagtaa ttggctaccc taaacacatc agttttaagt   47459
tgctgaaaag caaaacactc taccaaattt tgttttttttt ctagaccatg tttacaaagc   47519
aaaagtatgt tttcttcccc cccctcaaa aaatgactaa tgacactcct atgcgatgcc   47579
tttttatggt aaattgaggc ttttagttct ctttccattt agccacagac ttttgtgtcc   47639
aaagacaagc tgcgtaactg catatataag gttaaggcat aactactaat aaaagaatgt   47699
aaaatatttg atattaggtc tgtacaaaga ccaaataata ctcatgatta gacaagatta   47759
tatttggtag aatctatcca tcatatggct tcagatttta cttttcagct tggctttgtg   47819
agactttaaa aatcaagtca ttgcacttat attcacaaag tcacattgct ttactgcatt   47879
gcttctcata cagtttatct cctttcagta aaatgtttac ttgccatttt taaaatttct   47939
tatatgtgac acttctacac taagtccttt atgttgttag ttccacaatt ctgtgaggaa   47999
taggtttttt ttttttaatca tttgattgat gaagaacatt aagttccaca gagattaaat   48059
ggtacaggca tcacacaggc aggaagtaac agagctaaga ttagagtcca ggtctgatgg   48119
aattcagaaa gctaatgtgc tttccatgga actataatgc tttctaatat acagcatcta   48179
aaatatctga ggtaatttta atataaacag catgagattg acttaaatat tattgcatgt   48239 ag gt    aat gaa tct agc atg gat aag gca aag aaa  tca ata acc aac   48285
   Gly  Asn Glu Ser Ser Met Asp Lys Ala Lys Lys  Ser Ile Thr Asn
        1035              1040              1045 agt gac att gtt tcc att tca aaa aaa ata act  atg ctg gaa atg        48330
Ser Asp Ile Val Ser Ile Ser Lys Lys Ile Thr  Met Leu Glu Met
1050              1055                  1060 aag gaa tta aat gaa agg cag cgg gct gaa cat  tgt caa aaa atg        48375
Lys Glu Leu Asn Glu Arg Gln Arg Ala Glu His  Cys Gln Lys Met
1065              1070                  1075 tat gaa cac tta cgg act tcg tta aag caa atg gag gaa cgt aat         48420
Tyr Glu His Leu Arg Thr Ser Leu Lys Gln Met Glu Glu Arg Asn
1080              1085              1090 ttt gaa ttg gaa acc aaa  ttt gct gag gtttgatatt ataagtttta          48467
Phe Glu Leu Glu Thr Lys  Phe Ala Glu
1095                     1100 tcatacaatt atagaataaa gaattagttt tggtagacat tgtattattg ttaagtggtt   48527
tgtctggatc tctgaaatat cttattaata tagtgcctat gttttgtgta ataaataaat   48587
aaaagattta aatctgaatt gtttaaaagg aaagcagata tttctgtaag ttttttctcac  48647
```

```
caatgttata ttattagatt taatttatga aatgttattt actaaacaat ggaattgcct    48707
ttcaccacca tcccttcatt taacaaatat ttattcattg cctattacat gtcagaccct    48767
gtgttgggac tggcagtata gcaagaaaca aaatagacaa taatctctac tttcagggac    48827
tttacattct aattggtggt tttatatatt tttgatgtgg tcagaatcat taaactgtgt    48887
ggcagtaaat atagtttgca agtatttaac aatttatgat taaacacaac tcttacagtg    48947
tttgcttacc ttgagattta atatattttc aaagcattta tatcattttt gttttaacta    49007
tgtcactaaa tctatatgag taagatttta ttaactcatt tggatttatt tatagatgat    49067
acaattgaag taaatatata tgagcagatt gcattctaag caaagtaaga atattgcaag    49127
ttcagatatt attagataat gagttgccta ataaaaatga cttttggtgg attggaatat    49187
aaccagagtt tccatagttt gtttctgatt ctttcatatt ttttaccctc cttcagtctg    49247
ttcttaacac ttcacactta atataatatg tgaactaagg ccaagtaaag aggattgcag    49307
tactttaaaa gctaaattac aaagaaaacc tcaccaaaaa ttgatgtatc tgaacatttt    49367
ttgttacatt tccttag ctt acc  aaa atc aat ttg gat  gca cag aag gtg    49417
                   Leu Thr  Lys Ile Asn Leu Asp  Ala Gln Lys Val
                           1105                1110 gaa  cag atg tta aga gat  gaa tta gct gat agt  gtg agc aag gca       49462
Glu  Gln Met Leu Arg Asp  Glu Leu Ala Asp Ser  Val Ser Lys Ala
1115                1120                1125 gta  agt gat gct gat agg  caa cgg att cta gaa  tta gag aag aat       49507
Val  Ser Asp Ala Asp Arg  Gln Arg Ile Leu Glu  Leu Glu Lys Asn
1130                1135                1140 gaa  atg gaa cta aaa gtt  gaa gtg tca aa gtaagtgcat ataagcattt        49556
Glu  Met Glu Leu Lys Val  Glu Val Ser Lys
1145                1150 tagccatttg actagatgta tcttctttaa tttgtcttta agaaacccaa ttacaggtat    49616
acaattctta gtagtaattg atactgattt ctttttataa gaacaggatt aagtaatatt    49676
aagatcggtt ttaacagggt taaataataa tattgacgag aataatattg ttaaagagga    49736
agtgacctct caagatttgc attttttaga gttcaggaat attattgcag aaaggtccag    49796
ttcctccaca tattgatttt ttggggaagg ggtgatggag gaggaatggt tgtttattgt    49856
atttaaactt aagtttcttc attttaataa gggagtaata gtacctcttc tacctgtttc    49916
ataaggttgc tgtaagaata taataaaaaa ttcagatttt gatttagttt acatttatcg    49976
ggcatctact atgtactagt cacggtgcaa ggtattaaac atatattgac ttgtacaatt    50036
atacttaacc ttgaggttat attttttgttt tcattttaca tgaagaaata tgcccagcta    50096
gtttagaaca caaatatat ataaggagta aatactgcgt gctggctggg cgtggtgaca    50156
tgtgcctgta gccccagcta ctcgggaggc agaggcagga gaatcgcttg atcccgggag    50216
gtggaggttg cagtgagccg agatcgcgcc actgcactcc tgcctggtga cagagcgaga    50276
ctctgtcaaa caaacaaaca aacaaagaaa aacaaaacaa aaaaccgtg tgccagctat    50336 atgctgtatt tcattctct tttgtaatta ggtgatattt cagtagaaaa gtataaggag    50396
cacttagtta atctgtcaag cataaatagt aaaaatattt tatggcctac tcataaaaat    50456
ataaccattc ctttggagcc ttgatagttc tcttgggaat atcagttttt gacatctttt    50516
tcactatgaa agaccctttt ttttaaaaaa attgatcctt tcttctcatg gacctctttt    50576
gatataaact aacttataat agttcatttt aatcatattt tgttaatcat gcaactggca    50636
atgagagcct ctcatcagta tgaggaaacc tgccttatct ataatactga actaaaatta    50696
```

-continued

```
ttctaaccca aagcaaagaa actttacatt ttgctttgcc tgtattagct tatcacagta    50756
ttcatgaggg aatttgaagg acttattacc attaggctat ctcttttttt ttttttttgt    50816
aattttatta aatgcatgtt ttgtttcttt tcacattact gataacttgt agattaaaac    50876
aaatcaaaac atgcattaat ccatctaagg atcctagaaa ttttacattt ctgtgttctt    50936
aactgtgtga tggtcttaga taaatgtact aaataccttc tcctagcata ttccaaatta    50996
tgacaataaa tgttttatgg aaaaaagtat gggaacagaa gttctttggc tatatacatt    51056
tggaaaatac tatatagtaa gtatgatttg agataattat atatgataga acctctggga    51116
gcactgaata tatgttagga atattcaaga gggaggaggg atgttgagaa tgaagttttt    51176
tttatatagc aaacatgata acctctgatg gaattatgtt tcatgaaaca gtttaggaaa    51236
tcctgtttta atatttcata caaagaagag atagatgctg aaaacgaatg gctttttgaa    51296
aaagggtcta gaaattttga attttggcat ttacttagaa agtgtactta attgttcctg    51356
aaatacctta tcatttccta g a ctg  aga gag att tct gat  att gcc aga      51405
                        Leu Arg Glu Ile Ser Asp  Ile Ala Arg
                                    1155             1160 aga caa  gtt gaa att ttg aat  gca caa caa caa tct  agg gac aag       51450
Arg Gln  Val Glu Ile Leu Asn  Ala Gln Gln Gln Ser  Arg Asp Lys
   1165                  1170                 1175 gaa gta  gag tcc ctc aga atg  caa ctg cta gac tat  cag gtatgtcag     51499
Glu Val  Glu Ser Leu Arg Met  Gln Leu Leu Asp Tyr  Gln
   1180                 1185                 1190 tattggctct tctacataga atccacttttt ttccctaaat ttacattaga tgttgggagt   51559
gggatatgtt atactttttg tttgtttcga gataggtgtct cattctgttg cccagggtgg   51619
agtgcagtgg tacattcaag gctcattgca gccttcacca cctgggttca ggtgatcctc    51679
ccacctcagc ctcttagaca gctgggacta caggcacgtg ccaccacacc taatttttt    51739 gcatttttttg tagagacagg gtttcaccat gttgcctagg ctggtcccaa actcctgggt   51799
taaaatgatc tgcccaccctt gacttcccag aatgctggga ttacaggtat gagccaccat   51859
gctgggccat tgttacattt ttaatcaaaa gatataccaa ccagaggctg ttattcttgt    51919
tagttggaac ctgattagaa agctctttaa tttgaaatat tgttcagtaa tccagtacag    51979
catttaaatg cctatagatg aattatgctg ctgatcaaaa ttaggacact gagaattgta    52039
gttagtaaat cttaataac aatattttct cttgtattta tatgtaactt tttacatatt     52099
cttacgttat atatgttggg aattataaaa acatacacat tgtcctgatc agtattatgt    52159
tacttgcaat ggaggttaaa aaaaaactgt aacagtcagg catggtggct cacgcctgta    52219
atcccagcac tctgggaggc cgaggcaggc ggatcacgag gtcaggagtt cgagaccagc    52279
ctgaccaata tggtgaaacc ccgtccctac taaaaataca aaagttagcc aggcgtggtg    52339
gcatgtgcct gtaatcccag ctacccagga ggctgaggca ggagaattgc ttgaacccgg    52399
gaggtggagg ttgcagtgag ccaaaatcac gccattgcac tccagcttgg gtgacagagt    52459
gaaactctgt ctcaaaaaaa aaaaaaaaaa acaccagtaa catacccact gttattcagt    52519
tacatttgga ttttaagttt gtttgattct aggttttttc ttttacagtt ctttggtaat    52579
tatttgtatt aaagcaaagt tacattttg tagatctcat gtgccactgt gttaaaactt     52639
tgcttagtaa attgtgaatt ttaaatctgt gataactttc actggaaaaa tttgaaactt    52699
actacaaata tatattttt ttaatatcag gca cag tct gat  gaa aag tcg ctc     52753
                                  Ala Gln Ser Asp  Glu Lys Ser Leu
                                                1195 att  gcc aag ttg cac caa  cat aat gtc tct ctt  caa ctg agt gag       52798
Ile  Ala Lys Leu His Gln  His Asn Val Ser Leu  Gln Leu Ser Glu
```

```
Ile Ala Lys Leu His Gln His Asn Val Ser Leu Gln Leu Ser Glu
1200            1205            1210 gct act gct ctt ggt aag ttg gag tca att aca tct aaa ctg cag      52843
Ala Thr Ala Leu Gly Lys Leu Glu Ser Ile Thr Ser Lys Leu Gln
1215            1220            1225 aag atg gag gcc tac aac ttg cgc tta gag cag aaa ctt gat gaa      52888
Lys Met Glu Ala Tyr Asn Leu Arg Leu Glu Gln Lys Leu Asp Glu
1230            1235            1240 aaa gaa cag gct ctc tat tat gct cgt ttg gag gga aga aac aga      52933
Lys Glu Gln Ala Leu Tyr Tyr Ala Arg Leu Glu Gly Arg Asn Arg
1245            1250            1255 gca aaa cat ctg cgc caa aca att cag tct cta cga cga cag ttt      52978
Ala Lys His Leu Arg Gln Thr Ile Gln Ser Leu Arg Arg Gln Phe
1260            1265            1270 agt gga gct tta ccc ttg gca caa cag gaa aag ttc tcc aaa aca      53023
Ser Gly Ala Leu Pro Leu Ala Gln Gln Glu Lys Phe Ser Lys Thr
1275            1280            1285 atg att caa cta caa aat gac aaa ctt aag ata atg caa gaa atg      53068
Met Ile Gln Leu Gln Asn Asp Lys Leu Lys Ile Met Gln Glu Met
1290            1295            1300 aaa aat tct caa caa gaa cat aga aat atg gag aac aaa aca ttg      53113
Lys Asn Ser Gln Gln Glu His Arg Asn Met Glu Asn Lys Thr Leu
1305            1310            1315 gag atg gaa tta aaa tta aag ggc ctg gaa gag tta ata agc act      53158
Glu Met Glu Leu Lys Leu Lys Gly Leu Glu Glu Leu Ile Ser Thr
1320            1325            1330 tta aag gat acc aaa gga gcc caa aag gtaaacattt aaacttgatt        53205
Leu Lys Asp Thr Lys Gly Ala Gln Lys
1335            1340 ttttttttta agagacagta tcttgatctg tttcccaggc tggagttcag tggtgcaaac 53265
atagctggaa ctcctgggct caagggactc tctagcctca gcctcctgag tagttgtagc 53325
tggcagtaca ggtgcacacc accatacccta cctaatttttt aaaatttttt aatttttttt 53385
gtagagacaa ggtctcactt tgtcacccag gctggccttg aactcctggc ttcaagtaat 53445
cctcctgctt tggtctctca aaagtgctga gattacaggc atgagccact gtgcccagcc 53505
aattttaaat tcattatctt caaaagagtt acatgataat ttcttaatat atgcctatat 53565
gaaaaatgct taagatacaa attccaatta tgattcatta atttagattt tataacttag 53625
cagtgttggc tatttgaatg tctattatac gtaaaaataa aattaggctt ttctaaccaa 53685
agattttagt gggaatgttc agattgtata atagcaaaga atttaattca ctataggaaa 53745
atttatatta attaaacact aattattata tttaaacatt gtagtagtta tcagttgatt 53805
tctactgttc ataattatct ttgatctaca agtagtgggc ccacatttac ttttaatatg 53865
gtttaatctt catttagaaa gaattaaatg aaaaataatt atcttgcaac tacatcctgt 53925
tctctaggct agaaacattt aggatttctg ttttttgaaag taataccaaa gttccaatga 53985
cctgcttata gtcagtgttc aataaacgta taacaaatga aagtgaatat tagtgatgtc 54045
cattccaaca taatttgaag atttttattg taaaatccca catatttgta gaaaagtcta 54105
tggaaatcct aaataagatt ttgtcatgta gtttgacaaa agataacatt gtgtcttatt 54165
ttattttaga atggccatta ctttcaatta aaatcattat catcaatgga ggaatgttat 54225
ttgttaatat agcatttata tttgtgtata taaattgtaa atcttag gta atc aac   54281
                                                   Val Ile Asn
                                                   1345 tgg cat atg aaa ata gaa gaa ctt cgt ctt caa gaa ctt aaa cta       54326
Trp His Met Lys Ile Glu Glu Leu Arg Leu Gln Glu Leu Lys Leu
```

```
                     1350               1355              1360
aat cgg gaa tta gtc aag gat aaa gaa gaa ata aaa tat ttg aat        54371
Asn Arg Glu Leu Val Lys Asp Lys Glu Glu Ile Lys Tyr Leu Asn
            1365                1370                1375
aac ata att tct gaa tat gaa cgt aca atc agc agt ctt gaa gaa        54416
Asn Ile Ile Ser Glu Tyr Glu Arg Thr Ile Ser Ser Leu Glu Glu
            1380                1385                1390
gaa att gtg caa cag aac aag gttttatttt atatttattt cattttttc        54467
Glu Ile Val Gln Gln Asn Lys
                1395 cctaagttttt tttttttttt tttttttttt gagatggagt ctcactctgt cgcccagact  54527
ggagtgcagt ggcgtgatct cggctcactg caagctctgc ctcccgggtt catgccattc   54587
tcctgcctca gcctcccaag tagctgggac tacaggcacc cgccaccgtg cctggctaat   54647 ttttttgtatt tttagtagag acggggtttc accatattag ccaggatggt cttgatctcc  54707
tgacctcatg atccgcccgc ctcggcctcc caaagtgctg ggattacagg cgtgagcccc   54767
taagatttta aacaagaata ttgcacaaat gactatgtta tccttctaat taagtgcacc   54827
ttccattact aattgattat ataataattt gttttttatt ttctaaacta ttctaaaaat   54887
tcatatttat ttagctttta taacagtagt cttaatctta aaaacggcaa tacataagca   54947
acctcatttg gtaagttaat ttttatttttg atattggtta tttgactttt cacagttcca  55007
cgtttctact ggctctcact gatagagtaa gaagtcagct tcttatagaa taagtatat    55067 acttcagaga cagatgaaat tcgtcaaaca tatgactgtc tcagagattg ttccccctgc   55127
ttaaattgtt cttaccctag atacctttgg tatttacact gtcagtgcct gcaggtctta   55187
gctcaaatgt cttaccttat cagtgtatcc ttcaccagcc acctaatata caacagtaaa   55247
tcctactatc cagattccta aatagagatt aattaactta attttctcc aaagtgcttg   55307 taaccttctg acgtattaca tacttactgg tttattattg actgtctttc cttcgccaga   55367
atgcaagttc cgtggtgaca cggacttggt tttgtttact gccatgtttg tatttcctag   55427
aatgatgctt ggcacataat atatgtcatc aaatatcttt cgtatagctg aacggatgga   55487
tggatggatg gatggatgga tggatagact gaaatcctta cttcacatct gcctttgtga   55547
tcttacacaa gttacttcac ctctctgagt ttgtattttt ttccataaaa ggaaaataat   55607 tacagttttct tcaatgtgtt gtgaggatta gataagaaaa tatatataaa atgcctgtta  55667
tgtgcctgat gtcttcgtgt atgtgtctga cacaaattgt cctttttta g ttt cat    55724
                                                          Phe His
                                                          1400 gaa gaa aga caa atg gcc tgg gat caa aga gaa gtt gac ctg gaa        55769
Glu Glu Arg Gln Met Ala Trp Asp Gln Arg Glu Val Asp Leu Glu
                1405                1410                1415 cgc caa cta gac att ttt gac cgt cag caa aat gaa ata cta aat        55814
Arg Gln Leu Asp Ile Phe Asp Arg Gln Gln Asn Glu Ile Leu Asn
                1420                1425                1430 gcg gca caa aag gtatgaatga ttaatcttgt ttgttactct gtagcatagt         55866
Ala Ala Gln Lys ctagagtgtt aactcacaga aatatttcct gtatcagatg taattttaat tgatgttata   55926
ttgtatattt aaaatataag aggggtttaa tctatgtttt atcatacagc tgtaaaaatt   55986
aatagttact ctcaatgctg caactgcttt tttaaaaaac atactatttc ttaatag      56043 ttt gaa gaa gct aca gga tca atc cct gac cct agt ttg ccc ctt        56088
Phe Glu Glu Ala Thr Gly Ser Ile Pro Asp Pro Ser Leu Pro Leu
1435                1440                1445
```

| | | |
|---|---|---|
| cca aat caa ctt gag atc gct cta agg aaa att aag gag aac att<br>Pro Asn Gln Leu Glu Ile Ala Leu Arg Lys Ile Lys Glu Asn Ile<br>1450                             1455                     1460 | | 56133 |
| cga ata att cta gaa aca cgg gca act tgc aaa tca cta gaa gag<br>Arg Ile Ile Leu Glu Thr Arg Ala Thr Cys Lys Ser Leu Glu Glu<br>1465                             1470                     1475 | | 56178 |
| gtaattagaa gaatttgcat tttgattagt gtattatttg gtatgtttgg ggggctttct | | 56238 |
| aaataatatt tctttatgag ggcaatgcat agaatgatga atctattgct aatttcacta | | 56298 |
| tttttctatt ctcctataat gtttctaata gccaataatg aacagcagat atagttaatt | | 56358 |
| tgaattcact atttaattat tagttggtac ctttcggtac actgaatatg aaaggaaata | | 56418 |
| aaaagcattt aattgtagtt ctatgagcaa tatattctct tatatgatct ctttattctt | | 56478 |
| acttttttgg ttttatttg aagtgcatgt tacataatct atgaatcaat tttcagttca | | 56538 |
| ttgcctttaa tgcatggtta aagggttgaa ggtaaattag aaattacttt ctgttttaac | | 56598 |
| ctagatcttg aatttgatta gtaggtgatc aaatctgtca tcttcattaa attattcaga | | 56658 |
| aaataatgta aactgaatgt gttttcattt tagtttcat ctaaataaac tgcaaataca | | 56718 |
| tttaaaatat acataaagaa gttttcaag taaaactgta cattttaat catttcagga | | 56778 |
| aacgtagatt ttcttcagta attttaagat ttgtcattta tgtgaattgc cattgaatta | | 56838 |
| cttaatttaa aatactcacc ttaatcctct tgaagagtaa aaattttct gtttttttct | | 56898 |
| ctttgtttta ataagctgcg gattttatat tcgtaattta ttgagttggg cctctaaaat | | 56958 |
| tccagttttg tacttaactg acttatagat tagtctccta atgctctgct agtcaatgga | | 57018 |
| ccaaaataaa agaaataatt tattacatat tcttcctaaa tctagtacca ccatacatgt | | 57078 |
| ataattctaa actgtaatat ctcaataaag taccttaatt aaattttatg ttcatcataa | | 57138 |
| caatgaagtt tctagcatat gtaatagtct tataaataag catgcaaata actgctgtca | | 57198 |
| attagaatta gtcagtttaa ccttattaag tatcaaatgg ctattgtaca tatgatgtga | | 57258 |
| aaaataaagt gaattttttt tggctaataa ctaatctaaa attcagatga agcattttaa | | 57318 |
| agggaaaaag atactttaat gatttattat aatttaatca ttgcag aaa cta aaa<br>                                                                              Lys Leu Lys<br>                                                                                1480 | | 57373 |
| gag aaa gaa tct gct tta agg tta gca gaa caa aat ata ctg tca<br>Glu Lys Glu Ser Ala Leu Arg Leu Ala Glu Gln Asn Ile Leu Ser<br>         1485                         1490                         1495 | | 57418 |
| aga gac aaa gta atc aat gaa ctg agg ctt cga ttg cct gcc act<br>Arg Asp Lys Val Ile Asn Glu Leu Arg Leu Arg Leu Pro Ala Thr<br>                1500                         1505                        1510 | | 57463 |
| gca gaa aga gaa aag ctc ata gct gag cta ggc aga aaa gag atg<br>Ala Glu Arg Glu Lys Leu Ile Ala Glu Leu Gly Arg Lys Glu Met<br>                1515                         1520                        1525 | | 57508 |
| gaa cca aaa tct cac cac aca ttg aaa att gct cat caa acc att<br>Glu Pro Lys Ser His His Thr Leu Lys Ile Ala His Gln Thr Ile<br>            1530                         1535                        1540 | | 57553 |
| gca aac atg caa gca agg tta aat caa aaa gaa gaa gta tta aag<br>Ala Asn Met Gln Ala Arg Leu Asn Gln Lys Glu Glu Val Leu Lys<br>               1545                         1550                        1555 | | 57598 |
| aag tat caa cgt ctt cta gaa aaa gcc aga gag gtattttatt<br>Lys Tyr Gln Arg Leu Leu Glu Lys Ala Arg Glu<br>                 1560                         1565 | | 57641 |
| atattatgag ttatgctgtt atccattagt tttttaagc aaatgctaaa tattattta | | 57701 |
| ccctaaagtg gtatttcttt tcttgctttc aaatgattct atttaagaat tgttactgc | | 57761 |
| atgtgattgg attacacctc tgtcagtaaa actggaagtt tgtgtacatg tatctttcta | | 57821 |

```
ttatacactg actaaaccac gagtagctat catggtgaaa tcatatgatt ttgaaaaata    57881
ttttaattga gtttataggt gaggattgag gcaatagggt ggaatgaaat atatcacacc    57941
ggtaatcagt agaaatcaga tttgttagaa cttcgtgggg gaaagctaac atttaatttt    58001
ttctagaagt aagttaaaag atgatagata catgtcattc taatgttaag aataaattat    58061
gaactgaggc tgggcttgtc aacttgaaca ttgtctgagg ggacatgcat accagtctag    58121
atacatacat atatggagat actgtttctt cctcatctca aaggaatttt agaagattga    58181
agagaaaata tataaggtct tcaaaatgtg aatttgtttt aatcacaatt taagatatag    58241
tttcgatttt ctgtaaaaca g gag caa aga gaa att gtg aag aaa cat gag     58292
              Glu Gln Arg Glu Ile Val Lys Lys His Glu
                     1570              1575
```

```
gaa gac ctt cat att ctt cat cac aga tta gaa cta cag gct gat         58337
Glu Asp Leu His Ile Leu His His Arg Leu Glu Leu Gln Ala Asp
        1580            1585            1590
```

```
agt tca cta aat aaa ttc aaa caa acg gct tgg gtaagattct               58380
Ser Ser Leu Asn Lys Phe Lys Gln Thr Ala Trp
        1595            1600
```

```
aagaactttg ttccattctt tattgatttt tgtgaccatg taaattaaaa ttcagctctc    58440 ttctttttg gaatggaagt tacccttttt gttgccaaaa taatcttctg aaaacatagc     58500
tctgatcatt cttcctcctg tagctcaccg ctgttcacaa aattatattt ataattctta    58560
gccatgtact caatctgcta tgaacctacc tgcctttctt ttcaaattct actcactgtg    58620
agtttagcta tatctaactt ccagaattca gctcatattt gcctcttttg accattctgt    58680
tccatatgta tgaaatgaca tgtctttcat cttttaatgt gtaaccttag catatttgag    58740
cattacctcg ttaattcggt caacacttat tgatctcctg ctacgtgcag acattttgct    58800
agctattgta aatacaaata ataaagtctg catttcctgt cttctttaag ccttcattgc    58860
ctattaaatc attacatttt agattagata ttatatttg atcatttgag gaaccaaatt    58920
aaaaatatgg aataagtatg gcattgaatt atacatgcct attgctaata tattcatatt    58980
```

```
ttatag gat tta atg aaa cag tct ccc act cca gtt cct acc aac aag      59028
       Asp Leu Met Lys Gln Ser Pro Thr Pro Val Pro Thr Asn Lys
       1605              1610                1615
```

```
cat ttt att cgt ctg gct gag atg gaa cag aca gta gca gaa caa         59073
His Phe Ile Arg Leu Ala Glu Met Glu Gln Thr Val Ala Glu Gln
       1620             1625            1630
```

```
gat gac tct ctt tcc tca ctc ttg gtc aaa cta aag aaa gta tca         59118
Asp Asp Ser Leu Ser Ser Leu Leu Val Lys Leu Lys Lys Val Ser
       1635             1640            1645
```

```
caa gat ttg gag aga caa aga gaa atc act gaa tta aaa gta aaa         59163
Gln Asp Leu Glu Arg Gln Arg Glu Ile Thr Glu Leu Lys Val Lys
       1650             1655            1660
```

```
gaa ttt gaa aat atc aaa tta ca gtaagtcttc gaaatgtatt                 59206
Glu Phe Glu Asn Ile Lys Leu Gln
       1665             1670
```

```
gtaaaaatag gcaaatgata agtgatataa tgaagataaa cataagtgtt tgctatgcca    59266
ggcactgttc taagactttt aagtatattg tctcattttt atcctcagga ctgctggtta    59326
catatgttat cattttcccc attttaaaga gaggatatgg cctcaggaat gcttaatagc    59386
atgtctgggg gtagatggga aagccataat ttgaaactag tcagtctgac tcaaaagcca    59446
atacaaattc ttttccagaa tctcattttt accttctttg agcctcagtt tcatcttatt    59506
tatttatttt tattttgag acaaggtctg gctctatttc ctaggctgga gtgcagtgac    59566
```

```
ataatctcag ctcactgcaa ccttgacctt ccaggctcaa accatcttcc cacctcagcc   59626
tgcagagtag ctggcactac aggcaggtgc caccacacct gggtagtttt tttgtatttt   59686
tgtagagaca aggtttctcc atgttgccca ggctggtctt gaactcgtga gctcaagtga   59746
tccgcccact tcggcctccc aaagtgctgg gattacaggc ctgagccatt gcacccagcc   59806
tcatcatctt taaaatggaa ataataatac ttaccctggc cctttcaggg tggttatatg   59866
aaggtcaaat tataccgtgt atgaaagtaa tttgaaaact gtaaataac atacagatag   59926 aaaactttg attacacact tataagagtg tctgtcatat aatagagatt ctaaacattg   59986
ttcaaccact ttatcagaac gtagatttta aactcaaaat aggtttatag ttaggtagtt   60046
tctaatcatt ataatattat ctctatgggc ctaaatttta ttatctgaaa aaacatgaga   60106
aaattgaact gcttgactta taattccatt tcagctctca agcccctgct agagtctttg   60166
attctttact cacttattca aatgcctctg acagaattaa cactatttt gctttgctaa   60226 ggagctgcca ctgttaagaa attactctct aaaagaaaga aaattggcaa cagcatatgt   60286
gtattttcag tctctttcc tcactctatt aaattttgta caagagatgt tattttggt     60346 ctagtaaatt tctgtcatgt tttggagtat aaaattactt gtgcttttgc atctaatttg   60406
tgggtgtaga aaatcataat cttttgaaat accttatata atacattttt ttgccacagg   60466
aaatacttga agttattgtt gtgtaccta cgtcatttta gtccaaaatt atacttgtgt    60526
tctctgtgtg catattttga tatgtattag gagattatgg atctgtgtga tttcttaagt   60586
aaatcctgat attttcacaa tttgatgatg actctttaaa gttagactta agttttgcca   60646
aaagcaagaa gcctcaaaga gtaacatttg ttcatgtctt aacactatct ccctcttatt   60706
ggtcagaatc tcagtatgga tgcagtgtcc atatgcacaa caatatatta attcagttta   60766
acagacttaa tgctgaataa gcaataagat taattgaatt aactaaatct tttgatagta   60826
tccacttcca tatatatagt tatagatata atgctagtga atttgaacca taaacaaatt   60886
aataatacat gtgatttctg tgaaaattta tattagtctt ttcaatatgt caatataggg   60946
cagtatttct caaatataga ggatcagttt ttcaccattg tccctcttgg ggacatttgg   61006
cgatgtctgg agacattttt gattgtcatg gctcgggggt gctactggta tccagtgggt   61066
agaatcaaaa gatgctgcta acatcctat catgcacaag gcagccccac caccaacaaa    61126
gaattatcca gtcaaaaatg ttactagtag tatggttagg aaactatcat atagaggaag   61186
caatcacatt ttacaagagc cataatattt aaaatgcctt tttgttcatt ctctgtatat   61246
ttgactagag tcacaaaata acttgataag attgttgcca aaaatattag aaactagaag   61306
aaaaatgtgt tgttaagtct aagagtagtt aaatgaaata aagaattatt cttctttgga   61366
tttggatgcc tgcatcaaga tttagattgt aaggatactt aggactgaac atttgctcta   61426
tatgaaattt gtattaatca aggtatgaat tgcagcaacc actctattaa ttacatatgt   61486
ttggccaggt gtggtggctc acacctgtaa tcccagcaat tgggatgcc aaagcgggct     61546 tatcacctga ggtcatgcgt tcaaactggc ctggccaaca tggtgaaacc ccatctctac   61606
taaaaataca aaaattagct gggcctgatg gtgcacgccc gtagtcccag ctactcagga   61666
agttgaggca aaaaaatcac ttgaatctgg gaggcagagg ttgcagtcag ccgagattgc   61726
gctgctgcac tccagcctgg gtgacagagt gagactgggt ctcaaaaaaa ttaaaaatta   61786 aaaacacac acacacatat gtttatttac atcag g ctt caa gaa aac  cat gaa     61840
                                      Leu Gln Glu Asn  His Glu
                                                 1675 gat gaa gtg  aaa aaa gta  aaa gcg  gaa gta gag gat tta  aag tat      61885
```

```
                                                                       -continued
Asp Glu Val Lys Lys Val Lys Ala Glu Val Glu Asp Leu Lys Tyr
    1680            1685                1690 ctt ctg gac cag tca caa aag gag tca cag tgt tta aaa tct gaa           61930
Leu Leu Asp Gln Ser Gln Lys Glu Ser Gln Cys Leu Lys Ser Glu
        1695                1700                1705 ctt cag gct caa aaa gaa gca aat tca aga gct cca aca act aca           61975
Leu Gln Ala Gln Lys Glu Ala Asn Ser Arg Ala Pro Thr Thr Thr
        1710                1715                1720 atg aga aat cta gta gaa cgg cta aag agc caa tta gcc ttg aag           62020
Met Arg Asn Leu Val Glu Arg Leu Lys Ser Gln Leu Ala Leu Lys
        1725                1730                1735 gag aaa caa cag aaa gtaagtaaca acagaaaatt atcaacattt aggaaaaata      62075
Glu Lys Gln Gln Lys
        1740 tgtggtagat tgcttttaga gaagatttgt aaatttataa agatggtag tataaatctc       62135 cgtgttgtaa taaaaagtat gagctttatc ttatgctgtt aaacaaggta ttttagacaa      62195 tgctgttttt gtgggcagat atagtccaat ttatcttttt atgttttcgt caatctgatt      62255 tgtgaattat ctatatgaag ttaggaaaaa tcttaatgta cattacaaaa atataatata      62315 tattacattg tattttcttt ttttctactg gaattttatg ctactgaggc tattttttaac     62375 aaatgaacaa ttttgaacaa tttgagggat tgagggaagt atgataatga caaaagggga     62435 tgaaaaaagg gggtcataga gatgttttg tgagaaggag ttggtcagtg tattctgatt      62495 tattagggtt ttttttagtt tatctcagat ttgatctatt taaattgttt tagaagatgc     62555 tggtgttttt ctgtgctagc tatgaaattt atgggtaaac tttaagcctt tcctagtcct     62615 tttgttgtct acctaaattc aattaatttc atatggaagg atgtagtaag tgagtaatat     62675 aaatatctaa aattggatgt ttgaaaacaa aacatacctg tttttttgtaa tagcttgatt    62735 taatgctgag ttctcaaaat cattattaag attttgaact ttcacattca atgtggaaag     62795 aattgagtgt aattacaaaa gatttatttg aaaaagttga gttgttaatt tgtgaaatat     62855 gttccattaa actcataata ttttagaaaa atagtaggaa gtaataaagc ttgtttattt     62915 tttatatcat atattcatat aaaatgtcag ttttccttta aaattacat ttttttttg       62975 gttaatttt ag gca ctt agt  cgg gca ctt tta gaa  ctc cgg gca gaa        63023
              Ala Leu Ser  Arg Ala Leu Leu Glu  Leu Arg Ala Glu
                      1745                1750 atg aca gca gct gct gaa gaa cgt att att tct gca act tct caa           63068
Met Thr Ala Ala Ala Glu Glu Arg Ile Ile Ser Ala Thr Ser Gln
1755                1760                1765 aaa gag gcc cat ctc aat gtt caa caa atc gtt gat cga cat act            63113
Lys Glu Ala His Leu Asn Val Gln Gln Ile Val Asp Arg His Thr
        1770                1775                1780 aga gag cta aag gtaacatca acacgtgtta atgtaacaaa atttctgata            63165
Arg Glu Leu Lys
1785 attcctattg gaagagaatt cactatgata tatagtaatt ttgttgatga atagggaatt      63225 tataatgcac tgttggtggc tagacataga cacacacatg catttttcaa caataagtct     63285 ctttatgata ctcatttact gattatcatc ttggggatta ggaaaggata ggccattatg     63345 aactactgtt tctaatgaaa ttaaatttaa gaaatatttt acttaggatt tttttttaaga    63405 ctttattatt ttttagagc aattttaggt tcacagcaaa attgagagga aggtacagag     63465 atttcctgta tatctcctac cctgaaagtg tacatttgt taaaattgat gaacctatat      63525 tgatacatca taatcaccca aagtccaagt ttaccctctat tttagctctt ggtattttac    63585
```

```
actctgtgtg tttagacaaa tgtataatga tatgtatcca tcattatagt attatacagg    63645
gtattttcac tgccctaaaa atcttctgtg cctctcttct tcattcctte ctctgcacct    63705 caccaaaccc ctggcaacca gtgatctttt tactgtctcc atagtttcac cttttccaga    63765
atatgttata gatggaaaca tacagtgtgt ccccatcatt ctcaccatag acagctagg     63825 aactcctttc tagtggcata catattgtct agtattgtaa gttaccctt tatatcttat    63885 ctttgtaaac taggttagaa attacttcaa gtcagagatt tgttctgtac tactcttatg    63945
cttcatagtg tttaaaacgt tgtcatatat attgttatat acttgtttgt ttaattaatt    64005
cagccaaaat gaaacgtgca tatttgataa aattttgttt gtgggtgttt gttgaagatg    64065
aattgcttta cactagttt tttttttttt ctcaaagtcg acttttttcc tcaaggtaga    64125
cttgacatga atatgaaaaa atatatgtag tttgtggtta ttttttttct cttgtgtact    64185
taaaaattca gactgaattt ttcttataat ggtatatttt ctgtttatg ttcctttat     64245 cattgatact tcttgaagag tcatgaataa tacctttctt tttctcttat tag aca      64301
                                                            Thr caa gtt gaa gat tta aat gaa aat ctt tta aaa ttg aaa gaa gca         64346
Gln Val Glu Asp Leu Asn Glu Asn Leu Leu Lys Leu Lys Glu Ala
1790            1795                1800 ctt aaa aca agt aaa aac aga gaa aac tca cta act gat aat ttg         64391
Leu Lys Thr Ser Lys Asn Arg Glu Asn Ser Leu Thr Asp Asn Leu
1805            1810                1815 aat gac tta aat aat gaa ctg caa aag aaa caa aaa gcc tat aat         64436
Asn Asp Leu Asn Asn Glu Leu Gln Lys Lys Gln Lys Ala Tyr Asn
1820            1825                1830 aaa ata ctt aga gag aaa gag gaa att gat caa gag aat gat gaa         64481
Lys Ile Leu Arg Glu Lys Glu Glu Ile Asp Gln Glu Asn Asp Glu
1835            1840                1845 ctg aaa agg caa att aaa aga cta acc agt gga tta cag gtaatttat       64530
Leu Lys Arg Gln Ile Lys Arg Leu Thr Ser Gly Leu Gln
1850            1855                1860 atttaactct gataatgtct gatttacaat atagaggtag tagtttattt ctactttatc    64590
attttatcta tggtatttgt taaaactgac tttcaaatca ctttgattaa tgtaattaat    64650
ttcttttgtg acttctattg tgtttatagt tctagagtag catattagta tgttgtatta    64710
aaatgcagaa gcagctacca gattatctta tgtattaagt gtcatttaga aagtatggtc    64770
agtgatagct tcagaaagtt gctattatat aattgaaata tttactgtct attttgtttt    64830
acatttattt gtaaaaatat aaagttacat tttatttttt ag ggc aaa ccc ctg      64884
                                              Gly Lys Pro Leu
                                                      1865 aca gat aat aaa caa agt cta att gaa gaa ctc caa agg aaa gtt         64929
Thr Asp Asn Lys Gln Ser Leu Ile Glu Glu Leu Gln Arg Lys Val
         1870            1875            1880 aaa aaa cta gag aac caa tta gag gga aag gtg gag gaa gta gac         64974
Lys Lys Leu Glu Asn Gln Leu Glu Gly Lys Val Glu Glu Val Asp
         1885            1890            1895 cta aaa cct atg aaa gaa aag gtatgtgaag aaacatactg acttatatgc         65025
Leu Lys Pro Met Lys Glu Lys
                1900 ttaaggtagt gacagagtaa gttaaataca tagctgatta acagttaata tactgcctta    65085 atttgatgac ctggctgtat taattctgta ttaattttga ggactataag cagtattgaa    65145 taacgtagaa aagtctaagt ttctgttctg taggaattta gagtctactt gaggagatac    65205 ctataatgta actcttattt ggaaattact acatcaattt cattcatctt tctgacatta    65265
```

```
gagtacctct gaagttcctt cacaccttaa catattcaac tgtgtatcat ttctctccaa    65325
agtaatcatt tacacaggtt ggtgcttttg acttttggga cagaaagata gacattttaa    65385 gatacccac tttgacccaa ataggtcctt tttaatcctt caggagacta ggctgttatt     65445
tcagatagca aagttatttg gaatatcttc agtatttgca gtaataatca gtaaccaatc    65505
tgctcataga ttaattctgt gggagaaatt gcttaaaatt ttatagttca tagtaaactg    65565
ttttgtaata aaaattactg attgaaataa ccccaaaaaa aactaaaatt ggctaaaatg    65625
cgtgtaatta aatttgttat ggacaataaa ttggagataa cttgttggta acattcaaaa    65685
tatcgaaagt gaactgggaa atgttgatgt tagcagtaat atttgccatt gaagaaaatc    65745
agtatggagg agctatggtt aggaaaattt ttattataaa atttacccag aaaatattta    65805
atgtctataa aataatttca atcacatgaa aatggaaaag aaaattctgt ctttaaaggc    65865
attgaataga aaataggtaa tggaattcaa atttcttaat agagtatgct cccaaaatta    65925
ttttctatga aaattcatta atgtcagtgt aatttattga cactatttgc gtggagtcac    65985
aacatgcttg ctgtcagaag ctttgctggt gaaaactgta agatcaaagt gtccttaatc    66045
ttttggattt ccatctttct aactccctaa ttggggatag gcctgatctt atccctaaat    66105
ggggataggt tagaaactgg tatgtttgtt cctaactggt gtgtttctat accagtttct    66165
aacctgattc ctatcagaat gttttaagag ccttgtggct ttgcctggac tcttctatgc    66225
tacagtttat ttagtttatt tattcagttt attcctcctt aaagtgggaa taatactatc    66285
tgtattgcca gtttctcagg attattttac ataaaatgat atgatatgcg gaagtctttt    66345
gtaagccatc acatccatag cagtataaga tattactact aactagaaag agaaaacagg    66405
ggtctatgcc cagtattaaa attggcattc aggaatctag tgagaatatt ttttcaggtt    66465
cattgcttgg gcatttctaa tttatactca agaaatgctt tcatattgtt tggaaatttt    66525 agtaccctt tctctgtaaa cagaatttgt agtctaccta tgtaacaaaa cccacccctg      66585
tgccttgcat ttcattctcc ttagcattta ttactatctt aacatactag acatgtactt    66645
gtcttttgtt catctttttt ttttcttttt ttattagacc ataaactttg atggcaggaa    66705
ctttgcctat tttatttatt attgtattcc cagcacctag aacaatcgct ggcacatagt    66765
agatgctcag tatttgttga atgaatataa attttttaaat gttataataa tattattctg   66825
aaatctatgc atacgaagct tttggtacag aaaacatgaa aagagaacta ctgccttatc    66885
atccagtctt cttccctctt ctcattcagt ctagaacata acctgttttg gaaaaagttc    66945
tcaaaccata tgtttatctt gccctcaaac cataacaaca atcaatgcaa aagacttctg    67005 tgaccccag aatatgtggg gatttctcca catcagcaag caagcagttg gttttgtagc      67065
agacaccaac tgggtgtcgt ccaattcaat tcatcatcta cctggagata gtgtcagatc    67125
ccacagatat cttacttcga tcaaatcaca agtccaggcc tccgtgactt ccgaagttcc    67185
cacatcccca gccccagct ttgggtttga ttaatttcct ggagtggctc acagaactca     67245
gggaaacatt tacttacatt taccagtttta taataaaggt tattacaaag gatacaggtt   67305
aagagatgtg taagaagaga tatgggggaa ggggtgtgga ccttccatgc ctttctgggg    67365
tgccaccttc ctctagaaac ctccacatgt tcagttctcc agaacctctc tgaacccagt    67425
cctcttggtt tttagggaag cttcatgaca tcagtatttc ttctcctagg gtatgggca    67485 ggaccccctc gtattagggt tttaagaccc acagtcagaa aggcagggga agattacagt    67545
cctgccttag ggcaggtgaa aggaggatgg gagaaggtca gagagactct tttctgaggt    67605
gtgctcggaa ggcctaacac actcaatatt ataactaaag atgaggacaa gggctatgag    67665
```

```
agttataagc caggaaccat ggaaaaaagc ctatatgtaa taacaccaca atacccatgg   67725
taccattcac gtttgttgtt tttctgtttt tcaattgttc tttcagtctt ggttccctta   67785
atcttaattt agcaagtaat gccaggtggg ataaaattgc ccaaacccaa caaagtactg   67845
tgtgctgcag gattatttaa tgacatacct tatgtccccc actagtattt acatttctgg   67905
gagtacagaa aaattcttgt acatatttca gaaaaatga aattaataac tatcaaccac    67965
ttagtgaagt ttttactttt tttttgaga tggagttta ttcttgtcac ccaggctgga     68025
gtgcaatggc gcaatctcag ctcactgcaa cctccgcctc ctgggttcaa gtgattctcc   68085
tgcatcaacc tcccaagtag ctgggattac aggtgcctgg caccacgact ggctaatttt   68145 tgaatttta gtaaagatgg ggtttcacca tgttggccag gctagtctca aactcctgac    68205
ctcaggtgat ctgcccgcct ggccccca aagtgctgga ttacaggtat gagccaccac     68265
acccagactg aagtttttac attttttaaa gggcacttat tagctgaatt aaataaggta   68325
aaaaattgac tagtattaga gacaagaatt ggagaatata gttctctagt attcgagaaa   68385
gtcgttttga taggacaact aatcttagtg agaatttggc tttatttcat attttttaa    68445 tttttgaga tgacgtctta ctatgttgcc ctggctggtc tttgaactct gggctcaaac    68505
aatcttcctg cctcggcctc ccaaagtgct gagattataa gcatgagcca tctccccagg   68565
aatttgactt taaaccatgg ttctcaaccc tttcagattc aacattccct ttaataaaaa   68625
atataatgtt tcataatttc ccctttacta ttataattga aatgcatagt taacataaac   68685
tctacctact tacataattt caaaaatgtc attatgaatg tcctaaatga aatatatagg   68745
gggaacataa aaggaatatt catatttcaa catgtaaatg ctttggcatg actccattgg   68805
aaaatataat gaactagtca tgtgcttgca ccttcattaa tgtgagttca aagctacgat   68865
tgcagactga cacaaatgtg ttctattggc aactgatggg tcatgatggt attgccattt   68925
gtaatttgat ttccaaaatg gtaaacaaat tgttggtgca gttctcagca aaacaatgtc   68985
tataatctta ccttttataa gactgttgta ttcctagaaa acttagtgta tagtaaaacc   69045
attaaaaaat tacttagtgt gaatatgtta gttggagata aattcttagc tcagaccagt   69105
gtaagcagaa ttttttactg tattaatatc cagtagaaca tttgaaagtt gttcagtgca   69165
tgagactatt ctgcattgga taggctttct ttggctcctt tatcatagtt ataataaacc   69225
atgacaccta cccctgaaat gccctaattc ccttccgttt cttttctttt ttctttta    69285 gcacttaaaa ctagctaact tactacaaaa tagatttaga tttatttctt gttttgttat   69345
ctgtatcgtt tgctcccttc tccccaatct atctaaccaa ctagtataaa ctagatagta   69405
agattcatga agatacactt ttttatctga ttttattcat tgttctatt cctattgcct    69465 ctagagtagt acttggcaca tggttagcac taaataagta cctgtcaaat gagtgaagta   69525
atgtgcattg aagacttgaa ggggctctga tgctaggaaa ttgtcatggg ataatagatg   69585
aggttggtcg tttgtacaga ggattcttgt tagaagctta ctctagtcat gattgtatta   69645
gaatcttcat ttaaaggctc ctgaagggtg ttggcattag tcagaactgt ctcccagaat   69705
tttatttgtc ttgtgataga ataaagcata gttagcctaa agagcagttt tcctaatagc   69765
tcggcatgcc caaagattct aggagttata caggttgaac atctaatcca aaaatctgaa   69825
atgctccaag atacaaaatt ttttgagcac caatatgatg ccacaagtgg aaaattctga   69885
tgtgacctca tatgatgagt cacagtcaaa acacagtcaa aactttgttt catgtacaaa   69945
attattaaaa aatattgtat aatactacct ccaagctatg tgtagaaggt gtatgtgaaa   70005
```

| | | |
|---|---|---|
| cataagtgaa ttttgtgttt ggacttggga cccatcccta agatatctca ttatgtatat | | 70065 |
| gcaaatattc caaaaatatt ttttaaaaaa atccaaattc taaaacacgg ctggttccaa | | 70125 |
| gcgtttcgta agggatactc aacctgtata gcaaaatgaa catatttaca tattctctag | | 70185 |
| gaaatattag tttacaattt ttctaggcaa attataattg ataaatcata aagaaaattt | | 70245 |
| aaaataacac tggtaatttt cctacctcct tcgttattgt tacag aat gct aaa<br>Asn Ala Lys<br>1905 | | 70299 |
| gaa gaa tta att agg tgg gaa gaa ggt aaa aag tgg caa gcc aaa<br>Glu Glu Leu Ile Arg Trp Glu Glu Gly Lys Lys Trp Gln Ala Lys<br>1910                        1915                      1920 | | 70344 |
| ata gaa gga att cga aac aag tta aaa gag aaa gag ggg gaa gtc<br>Ile Glu Gly Ile Arg Asn Lys Leu Lys Glu Lys Glu Gly Glu Val<br>1925                      1930                        1935 | | 70389 |
| ttt act tta aca aag cag ttg aat act ttg aag gat ctt ttt gcc<br>Phe Thr Leu Thr Lys Gln Leu Asn Thr Leu Lys Asp Leu Phe Ala<br>1940                      1945                      1950 | | 70434 |
| aa gtgagtttaa atatcattat aaaactaatt atgtgtaaaa tcctttagtg<br>Lys | | 70486 |
| acctggaaat tatatagctt tatcatagtt gataatatga gaaatggtct agtttaaatg | | 70546 |
| atcatttatt atctatgatt tacttacttt ttattttctt taaaatctgt tttaaatata | | 70606 |
| ttgtaacaat tatagatgga ttttcctgtg atctcgttgt aaattagctt atgacaaata | | 70666 |
| tagggtgtta caattattgt aatttggttt ggtaatgagt atgcaattga aaagccaaac | | 70726 |
| actgaatggt atatttcatg attctatatt aaattccaca g a gcc gat aaa gag<br>                                                      Ala Asp Lys Glu<br>                                                            1955 | | 70780 |
| aaa ctt act ttg cag agg aaa cta aaa aca act ggc atg act gtt<br>Lys Leu Thr Leu Gln Arg Lys Leu Lys Thr Thr Gly Met Thr Val<br>1960                      1965                        1970 | | 70825 |
| gat cag gtt ttg gga ata cga gct ttg gag tca gaa aaa gaa ttg<br>Asp Gln Val Leu Gly Ile Arg Ala Leu Glu Ser Glu Lys Glu Leu<br>1975                      1980                        1985 | | 70870 |
| gaa gaa tta aaa aag aga aat ctt gac tta gaa aat gat ata ttg<br>Glu Glu Leu Lys Lys Arg Asn Leu Asp Leu Glu Asn Asp Ile Leu<br>1990                      1995                        2000 | | 70915 |
| tat atg ag gtaagctatt atgtggaaat gtgccaccca ttgtaatgaa<br>Tyr Met Arg | | 70963 |
| aaactggttg accctagaa attgaaataa taaatgtgtg ttgtcttaag cttgggttat | | 71023 |
| gttttctttt cccatgtgaa ttgagatatt cctggttctt catatgccac ataatttgg | | 71083 |
| tgtattttg atcttttgaa tattatattg tgagactctg gttcttgttt aaattctatg | | 71143 |
| ggaaaatgta gatactttg ttttagcatg caatcggtct aattaggttc aggccacaag | | 71203 |
| ttccaacctc atttcttggg ctgtggttcc attttcaaa gccttttcaa tactcttcag | | 71263 |
| atctgtcctg cctgtgtacc tcacaatagg tgatctggta tgtgagctat gtaccattag | | 71323 |
| ttcagttctt agaaactttg gtattctgat taggatcgat ccatacattt gcagctcaag | | 71383 |
| agtgagccca gaagttcata aacaacttta tagggtccct ttcttgagct cctccctctt | | 71443 |
| tgccatctct ctgatacttt gtttccctag ggatttccat ttgggctttt agttacccag | | 71503 |
| tgatgccatg tacttcagga attgcacact tctgcagcca agcaagcaag aggagagtag | | 71563 |
| aaagaggaag aaaaaaacga cttttacctt accctcttag tatcatagct ctaccaattg | | 71623 |
| gagatttccc tcccaaaaaa tattagcttc tgtgagttcc cattgcagcc tctattacca | | 71683 |
| ctgctatggg atggcttaag ggttggggca tgaaagaaca gatagaagaa aaaaaagtg | | 71743 |

```
aggtgttttc atattgtctc ttgagtgtta aaagattccc tttctcttta ctcgagctag   71803
aattagaagg tttacctgga gctctctctg tcagtgcaga cacccatctt caggtttcaa   71863
ataatgttgt cttcagggca ggcagtaaca gaataaaaga aaaggtaaat tcatcacctg   71923
tttgctgcta ctttaagtcc tggtattcta ttgtaatctg ccttctactc ctttgcaaag   71983
tcctcaaatg gttgctccat gcatttagga gagagaagat tgaatgtatt tactccattg   72043
tacctggaac cagatgccct tgccctgcat caccccatgt catttcttag cagagccttt   72103 gagattttg tgtgtgtgtg ctttacaatc tctttccaag ttatatcttc tgatacagtc   72163
atggtcgtga aaagcaaaat aaaatcatgt gttaacattt aaaacttttt aattttattc   72223
tgacaacagc taaaactatt taatcttctg tttcgctcat ttcttccaag gtaaacttca   72283
gttggtttta cgtgatttgc tatttcttct cttttgcatt tacaaatgat ctgtgatcat   72343
attactgatc tttgtaaagg gctaatatct acctgcaaca tttggatatg acagtattta   72403
ccctttgtaa atacacattt tctatttatc ttcaaaaatt accattcatt agtctgtgtt   72463
aatgtctgtt tactattgtg tcattatgaa tgtgatgtga acatacgaag ttgaacttat   72523
ttaaacgaac actctcatga gcttctaatc cacattcctt cctttccctt ctaagttacc   72583
atttcttaaa aatcttttag aagtttcctt gatagggaaa acacaaatta ttgaggaatt   72643
tttctttctc ttgacatctg tttatagtta ctctcttgtt ccagcagtgg atatttcccc   72703
tccatgtttt tctttgtcta aacatatgtt caaaacaaaa cactttatt cttctttgca   72763 ggttttacaa ggatcaactt ttagttttga aacctgctat tacttttaga ggccattttt   72823
tttttctcta ataatgtgag ttcatgcggg ctgaagtaat tggaatactt tatagaaaag   72883
attgaatttg tcttctctct gaactctagt ttgaatttct aaattttatg aatcatctag   72943
atattaaaga ggagggcat atcaaagagg agaaccctag cagagataag aggcaagagt   73003
aaatgtttca tgtatgggta agagtggatt tgtatttacc taagtaaagg tagaccctgg   73063
acaataaggt tggatagatg tggaggtggc aaaccatgga gggtcttgta ggtcaagtgg   73123
atgtttttag acttgaagtg ttaaattatt atctgaaatc attaagagtc ttttagatc    73183 cttgagcttc ttgagaagac catggatatt atgcagttat tatataatgt tttaaaatag   73243
taagtatttt agtttaactg tcttatgtaa ttccatataa atggatgcat gttctttaaa   73303
aatgttaatg tatttcagta aatcaaaata tacttttga ctcatcattt aaaggaggcc     73363
ttcagtgaat gctctgtaga ggattatttt ataatactaa ttttgatatc ctaatttatt   73423
tgttataaag tttagaaggt ttgaagaatt taaaatatag tgttaataaa cacactgaac   73483
ttttcttttt ttatcttgta tttttatata gtacaacaga aaaagatga aatgtgaata    73543 gtaaagagtc tgtgattgtt gttcatag g gcc  cac caa gct ctt cct cga       73593
                            Ala  His Gln Ala Leu Pro Arg
                            2005                     2010 gat tct gtt gta gaa gat tta cat tta caa aat aga tac ctc caa         73638
Asp Ser Val Val Glu Asp Leu His Leu Gln Asn Arg Tyr Leu Gln
            2015                2020                2025 gaa aaa ctt cat gct tta gaa aaa cag ttt tca aag gat aca tat         73683
Glu Lys Leu His Ala Leu Glu Lys Gln Phe Ser Lys Asp Thr Tyr
            2030                2035                2040 tct aag cct tca gtaagtgtat atctttatt attttttct tttttccatg           73735
Ser Lys Pro Ser
            2045 ttaaaatgca tgaaagtgaa atcaacttct ttcttaatct ggccaaaagc attacatctt   73795
```

```
tctcattaat agtaatacag taaattcaac ttttattttt aacaggtagt gatgtgtaat   73855
aatttattta atccttttta acataataac agtaaactta agattcttaa gcttttcata   73915
aagctcataa atgatttcta gaaattttaa atatgtagtt atcattatgt attttgctgt   73975
agcagcagta tacagttaaa taaaatagga aaacatgttc caagactgtt ttcattcaaa   74035
tatttatgct atattttag cttataaaaa ctcattaatc attaatgtaa aattatttgt    74095 tggattttt aaatatttag tgtattattt ttgtttcttt tttctttcca tgtttcttca    74155
ttcttccacc ttaagcagaa tcaggtgtgt gacacaacta tgttttctat ccttgttacc   74215
attattaata aatacaaggg catgatattt tcacaaaag aaacactttg ttcagaacca    74275
aaaaagatca tggcaacagt cagaattaaa aatggtaaaa gactaggtgc caaagatgac   74335
ttacataatt gggtacctag aaatattcta tggtattaca gtaatgatga aaaatacaaa   74395
ttagaacaca ttttagatcc tattgagtta aataaatcag agtcaagacc aaacaataaa   74455
taaagtcaat ttacgtcaac aaatggtaag ttggcagatt ttaactccct ttttgaaaat   74515
gaaccatgat cctaaggttg gtaaaattaa tcaagaatgt tgtcaaaatg ataaagataa   74575
aaatgaggaa gagaataaga taggcaagag tgagaaagga aagagacaca tagctgaaaa   74635
tgtgagtcac aacaactaca tagatccgta gaatctgcta tggaggactg tgattatgtg   74695
acagttgctg atgccgtggc ttagtgagct gagggtgatg cacaggcagg cgatgtaact   74755
gatgcgtcag tccagccaag aaaggacgcg tccctggttt ggctacgtgg ccgtcccttta  74815 tttctttgtt aactgaattt tcttatagta agtagcttac gtacatatat agtgcaaatg   74875
ggaaagtgtg taagatttag aaaaagcatt aactattagt aaactttatc ttaagctcta   74935
acttttgatt agttcctaca aaaattagtg aatatgcatt ttctaattta gtgctttttt   74995 ttttttttaca attggtgttc acttaatgtt atattagata aatgaatagc aaaaataagg   75055
tactttagag ttgattgttt tgccttacaa acttctaatc catccagctg tatttagaag   75115
taagatctca ctacagcgaa ttatatcagt aaaattttgt tacagtgttg tgcagtgtcc   75175
taagatgtat actaagttcc ttcagtggct ttttttgcca tgttttataa cagataattt   75235
tgttataatg agaaaaggaa acttggatgt gttgctgtct atattgtgtt aggctcaggc   75295
aggatgctgt ggcttactca tttaatcact ttgggaggca ggggcaggaa gattgcttga   75355
ggccaagagt ttgagatcag cttgggcagc atagccagac cctgtctcta caaaaaattt   75415
agacagatgt ggtggaacac atttgtagtc ctagctatta gggaggctgt ggtgggagga   75475
tcatttgagc ccaggagttt gatgttacat tgccctattg cactccagac tgggcaacag   75535
agtgagacct gtctctaaaa taataataat gataatgata aatggtgtta ggctctgtgc   75595
ctaagtatat ttttcacata ggctgggtaa agtggctcat gcctgcaatc ccagcacttt   75655
gggaggccaa ggcagcagga gcatttgagg ccaggagtca aagaccagcc ttgagagacc   75715
ccatctctac cagaaaaaaa aaaaaaaaga aacaattagc tgggtgtgat tgtgcacacc   75775
tgtagtccta gctactcggg aggcagaggt gggcagatca cttgagccca ggagtttgag   75835
gttatagtga gctaagattg tgccactgca ctccagactg gcaacagag caagactgtc    75895 tcaaacaaaa acaaacaaac aaaaagcact tgcagaata tcagtctaac tctacagttt    75955
atggactttt tatgtacgta ctacttttgg ctagcttaca ttgagataca gaataaaagt   76015
ttgttcatag catttatcgt tttttctttt atactgtcca cctgagatat tccagtcacc   76075
taagtcatgg aaacatcaac taaaattaaa tatctatgtt aagagaaaat ggctgaaagt   76135
gatttaattc ataacacttt ttttcacatg ctaataaata agagtttgag acttccacta   76195
```

```
ggcattatct ctaactccta tccactaaga atttgatttt aagtagttga tggcttttaa    76255
ccggattatt cttctgtaag agtttggaag tctcgtgaag ttcgttatac aagaattctg    76315
tttacaagag agcattacat tagaatttgt ttttcagaaa tttggactat ctcaacgaat    76375
acctttagtt ttattatttc aaaatgcaag ggaaaaaatg agccataatc actaatagta    76435
actgcatcat attttagtga gaaatgtgtt aaaaatatcc tcatgtgaga tcttccttag    76495
atagaattac cctctactct aatatttaat atattttata tctaccaatc agtgatatta    76555
ataggtgttt atcatttgct gaatcaaata ggtacaacag aagacaggaa gtttgggaga    76615
tagaagagct cagggacagg aaatcacaga tgtccatatc tgaaataacc ttaaaagtta    76675
tcctgtctaa tgccttcact tataaactgt agtggtagaa tttgcctagt attaacctaa    76735
tagtggtaga tttgaatgta tacttgggct ttcttattaa gtggaaatgt attcctgtga    76795
tttacatata tcaacaaaaa tgtttgtctt cttttttttg ctacgacata tgtgcatgtg    76855
cacacacatc tcctcaaaca aaatcagat ggacacatgc agtcattgga tctaaaagat    76915
gttataaagt tgtgtataat aggtatttta taataatata ttttaagacc cataatgtcg    76975
gtggagtaac tgactttaca gcccatcaag ccaatagaga gagaaaggag aaaaaaatga    77035
aagttgtgct gaataattaa aaaaaattat ttcctatgat gcttataaca gtcctatgag    77095
gtaggtggta ttctaattta tagaaaaaat gcatagaaaa atataattaa gcacagttaa    77155
aaaaaataaa gtttagaatg agaagtaaca acataaataa tgacccaatg tagattcagg    77215
tcaaaagaaa tgaaaatata atattaatgg ttttcaaaga gggaaccatt actttagctc    77275
aaagaatgaa ggagggcttt ccgaaggagt aaagaattat ggcagttctt ttgtagccta    77335
gtgtattcat ttgctaaggt ggctgtaaca gactactaca gatttggtgg cttaaacaat    77395
agaaatttat ggtcttagtt ctggagacct agaagtccaa aatcaagaca tcagcagggt    77455
tgatttcctc tgcacaatca gagggaaaga tctttcccaa tcctctctcc ttggcttata    77515
aatgtccatg ttttccctgt ttcttttat catcttcctt ctgtacatgt ctctgtgtct    77575
aaatccccaa attttctctt ttcataagga taccagtcac agtcgaatag ggttaccct    77635 gaaatctcat tttaacttga atacctctgt aaagacccag tctccaaata aagtcacatt    77695
ctgaggtact ggaaattatg actttaatat ataaatgtgg agggtaaggg gaacacagtt    77755
caacccataa cggttagata acaatcgtgc tttattttgg actagtaaaa ccaccataga    77815
tcagtttaac cattatgaaa ttatacatga aggcattata tgtatggaca ttattaagtc    77875
atacttgctt tgcttccatt gtaattaaaa caaaccatac tacctttgtt ctgcaagttt    77935
tgtattctaa cttatttatt tttggctttc accagaacac tccgattttc tcatattcct    77995
ttgaggaaaa aaagttaccc tttgacagta ttttcttatc cagtatgtct tttatggctt    78055
ttatttatta aactttaaaa atattcctaa tttcatttcc ctgaag att tca gga       78110
                                                     Ile Ser Gly ata gag tca gat gat cat tgt cag aga gaa cag gag ctt cag aag          78155
Ile Glu Ser Asp Asp His Cys Gln Arg Glu Gln Glu Leu Gln Lys
    2050            2055                    2060 gaa aac ttg aag ttg tca tct gaa aat att gaa ctg aaa ttt cag          78200
Glu Asn Leu Lys Leu Ser Ser Glu Asn Ile Glu Leu Lys Phe Gln
    2065            2070                    2075 ctt gaa caa gca aat aaa gat ttg cca aga tta aag gtgaatttaa           78246
Leu Glu Gln Ala Asn Lys Asp Leu Pro Arg Leu Lys
    2080            2085            2090 tgttttttat taggaaatct aatgcctaaa actccttcct tagttgttat gtttactttt    78306
```

```
attagcttat taagaagtca aaaatgcata ttcctaatat atcatggtga tggtatactt    78366
tatacatttg ctctttagca tttatttgtt gaaggcctac tttatattaa acactcctcc    78426
agatgctggg aaacagcagt caaaaaattc cttatactca taggacttac gttctagtgg    78486
agaagactga caataaacaa gtcactaaat agtatgtcat ctgatgttag tgctaaggag    78546
agaaataaag catgattggt gtaaagagta tggggagaga aagggggtgt aactgaaaat    78606
agagtagtaa gggaggtctt ccttaataag atgatatatg aacagagagc taaggagggg    78666
taaaggaagt gagtcataca gatactagaa aaataattac agacaacaga aatagcaagt    78726
tcagatgtcc taaggtggga ggatgcgtgg tatatttcat taaaaattat cacactgtaa    78786
aatataagaa taatttgttt cttttagaaa ttttacttta ttctgatatt aataatgatt    78846
ttttaatctt tggttttcca agtcttaccc tatttatggg aatctttttt ttcttttggc    78906
tagctaattg cttcagtttt gttttctaat ctagaatgtt agcaatctgt taattccact    78966
ggtaatgata tagttaagct atgtcttgct tctcacactt tatttattta tttactcagg    79026
gcactaatct gccattttt cgcacttttt ttcctttttt tttttttggg tactgcttct    79086
tattctggtt tttacattga tagaaccaat gttagacgtt catttgcctt ttgctgtgta    79146
tatttgggta aggatctata tgtgcaatat atgggacagt taaaatcaga attctaaatt    79206
tgtattattg catcaggcaa taatgtggga aatacctgga catttcatat acacaatatt    79266
cttgtattaa tttaacgtct tagttcaaaa tcttccttgt taatatagag accctattat    79326
ttggtttggc aatacagttg aagagattga tggttcttat gaattgtttg ccttttcttt    79386
tcaatggctg tagctatgtt aaattattac atgtttgctt gttatctttc ag aat caa   79444
                                                          Asn Gln gtc aga gat ttg aag gaa atg tgt gaa ttt ctt aag aaa gaa aaa         79489
Val Arg Asp Leu Lys Glu Met Cys Glu Phe Leu Lys Lys Glu Lys
        2095                2100                2105 gca gaa gtt cag cgg aaa ctt ggc cat gtt aga ggg gtatgtgaga          79535
Ala Glu Val Gln Arg Lys Leu Gly His Val Arg Gly
        2110                2115 atttaccata catttgtttt ggtttcagca gtgataagcc agaaatgaaa agtttagata    79595
tgttgtaaaa gtactgatat gcctctacaa gtgccctgta gtttcagtgt ttattctgca    79655
tctgtaatat aaaacagtaa gcatttctat gtgtctcaaa gtattttatc atctgttata    79715
ccttacatac tttcatctct cttttttattg aatatgcctc cataccttga aaacatttaa    79775
cttccaggaa tccttttgtt tatggaggta actgctaact ggtccttggt ccaatgctgc    79835
cattttgtaa ccatttgtta tgatatcttc ccagcttggt ataatgtttt ataattacat    79895
tgttcctccc cctctttttt tgtgttcttg taattttctc cctatgttat tttgtattca    79955
ttttatataa tgaataaatg ttgcttatga ggtcaaggcc aaagacttaa gctcctgttg    80015
atttcatgtt gctgagtgtc ataaatgaaa gcaatcataa tgcagagtca ttctggtagt    80075
aatattaaat atatgatgga ttcagtgaaa atattatgtg ttattagaaa aatattcaga    80135
acaggccggg ggcagtggct cacacctgta atcccagcaa tttgggaggc cgaggcgggc    80195
agatcactgg aagtcaggag ttcaagacca gcctggccga catggtgaaa ccccatctct    80255
actaaaaata tgaaaattag ctgggcatgg tggctcatgc ctgtaatcct agctactcag    80315
gaggttgagg caggagaatt gcttgaacct ggcaggcgga ggttacagtg agccatggtc    80375
acacaactgt actccagcct gggcgacaga gcgagactcc atcttttaaa acaaaaaaaa    80435
aaaaggaaaa atattcagaa cagtatcttg ctggcagcaa catttgtttc atcaatgaaa    80495
```

-continued

```
atatgtgtta atttgacctt ttctatctaa gttaattatg aaagtgcata ctaaaatgat    80555
gtaaaagttt atatttcagg attattctta ttcatggatg attaactaaa atgcaaaaag    80615
aaattaagca tactgtttgg ctaaactgtt aaaaattatt tttattttaa atgataagca    80675
gttaaactta ttaagtgatg actcatctct gctgatatat ttatgcaagg ttttttattt    80735
cagataactc ttctatttat attaaacaga aactgtattt ctaagcaata gcatttctta    80795
gagaaaattg cctctattat gttgcaatta aaatttaatt actcatgagc tctttaaaga    80855
cacaatttct cttgtgtggt tttatttcat ataagaaaaa actctgatat actggagaga    80915
acattagcta aatagactat ttagacttaa tcattttgat cagacatcaa ggctagacta    80975
tttaagctgt tacttattag ctgcatgatt ttaggaatgt caaatttcct aagtcttggt    81035
tttcttgtat ttaaaatgga aattataatt cctatctcat agaattgttt taaggatgaa    81095
ttgaattaat acagttttga cttcaaatat taggaattat tgagtataat aagcctgttg    81155
tattgttggt acttcgtatt atacttacta aaatatttga ttaaagattt aacatattct    81215
```

| ttcgtag tct ggt aga agt gga aag aca atc cca gaa ctg gaa aaa | 81261 |
|---|---|
| Ser Gly Arg Ser Gly Lys Thr Ile Pro Glu Leu Glu Lys | |
| 2120　　　　　2125　　　　　　　　2130 | |

| acc att ggt tta atg aaa aaa gta gtt gaa aaa gtc cag aga gaa | 81306 |
|---|---|
| Thr Ile Gly Leu Met Lys Lys Val Val Glu Lys Val Gln Arg Glu | |
| 2135　　　　　2140　　　　　　　2145 | |

| aat gaa cag ttg aaa aaa gca tca gga ata ttg act agt gaa aaa | 81351 |
|---|---|
| Asn Glu Gln Leu Lys Lys Ala Ser Gly Ile Leu Thr Ser Glu Lys | |
| 2150　　　　　2155　　　　　　　2160 | |

| atg gct aat att gag cag gaa aat gaa aaa ttg aag gtaattttt | 81397 |
|---|---|
| Met Ala Asn Ile Glu Gln Glu Asn Glu Lys Leu Lys | |
| 2165　　　　　2170 | |

```
ttaatgtgat cattttagg ggaatatttt acgttttgtt actatttagg aaaatttcaa     81457
atatgctcat tactatataa aatggcttta atgaatacaa tacatatttt ataaatatag    81517
aaaaaaactt atgagaggca aggctaaggg ttatagagta ggtctacctg atctttcttg    81577
ttatttcaag accaatactt ttcacttttc tctctgacag catagattaa ttacctgtgt    81637
ctctcttttt tttttctttt gagatggagt actgctttgt cacccaggct ggaatgcagt    81697
ggtgcaatct tgactcactg caagctctgc ctcccgggtt catgccattc tcctgcctca    81757
gcctccccca gtagctggga ctacaggtgc ccaccaccac gctggctaa cttttcgtat     81817 ttttagtaga gatggggttt caccatgtta accaggactg tctcgatctc ctgacctcgt    81877
gatccgccca ctgcggcctc tgtgtctctt tgtgaaaata cagatgccca agctcccatc    81937
cctgaaattg atttaattat tttagggtgg gtcctgacac agatatgtat gttgttgtta    81997
ttttaagtca tcaatttatt ctaatatgta gccaacgttg ggaacttcgt tctcactaat    82057
attcaaatga agactttaat tctaatcata tcaaatatgg tttctaaaac tactttgaag   82117
atttatgagt ttataagatt atcttttatt tccttgtttt gataatgtat acttttatt    82177
```

| ttgtttgttt tttactag gct gaa tta gaa aaa ctt aaa gct cat ctt | 82226 |
|---|---|
| Ala Glu Leu Glu Lys Leu Lys Ala His Leu | |
| 2175　　　　　　　2180 | |

| ggg cat cag ttg agc atg cac tat gaa tcc aag acc aaa ggc aca | 82271 |
|---|---|
| Gly His Gln Leu Ser Met His Tyr Glu Ser Lys Thr Lys Gly Thr | |
| 2185　　　　　2190　　　　　　　2195 | |

| gaa aaa att att gct gaa aat gaa agg ctt cgt aaa gaa ctt aaa | 82316 |
|---|---|
| Glu Lys Ile Ile Ala Glu Asn Glu Arg Leu Arg Lys Glu Leu Lys | |
| 2200　　　　　2205　　　　　　　2210 | |

```
aaa  gtatgacttt tatgactgat tataactttt gatttttatt ttacttaata        82369
Lys
2215 cctcttggaa aaactggaag tagatccttg atgagagtgt ctgtaaaggt agatattaag  82429 agattgagga attgtgtttc tatgcctgct gtcatcacat tccaccatga aaaacattga  82489 taataaaagt taatacattt aggctgggca cggtggctca cgcctgtaat cccagcactt  82549 tgggaggcca aggcgggtgg atcacgaggt caggagatcg agaccatcct ggctaacacg  82609 gtgaaacccc gtctctacta aaaatacaaa aaattagccg ggcgtggtgg cgggcgcctg  82669 tagtcccagc tactcgggaa gctgaggcag gagaatcgct tgaacccggg aggcagaggt  82729 tgcagtgagc cgagatcgca ccactacact ccagcctggg caacagagcg agactccatc  82789 tcaaacaaac aaaaaaaaga aatgatctac gttgcttaca catacctat gcttatagct    82849 aggtctcgta agcattagga agtcaaaaca aagaatcttt tacatgtgta aaggtataaa  82909 ctatcccatt tttctaaaaa tatagaggaa caaagtgtca aatttaaagt aatcactagt  82969 aactaaatat attcctctga cctcatttc gtgatctgtt gttctaatta ttattggcca   83029 tattgctgct ttaaaggaga gatgttgaat ttgttgaaat tttaatcagc atttagagcc  83089 ccaggttatt tttgttttcc aatttgtaat gataattttg aatacactga atctatgaga  83149 acagtattat gttttctcat aaaatactaa ttagcattta atgatag gaa act gat    83205
                                                      Glu Thr Asp gct gca gag aaa tta cgg ata gca aag aat aat tta gag ata tta        83250
Ala Ala Glu Lys Leu Arg Ile Ala Lys Asn Asn Leu Glu Ile Leu
    2220            2225                2230 aat gag aag atg aca gtt caa cta gaa gag act ggt aag aga ttg        83295
Asn Glu Lys Met Thr Val Gln Leu Glu Glu Thr Gly Lys Arg Leu
    2235            2240                2245 cag ttt gca gaa agc aga ggt cca cag ctt gaa ggt gct gac agt        83340
Gln Phe Ala Glu Ser Arg Gly Pro Gln Leu Glu Gly Ala Asp Ser
    2250            2255                2260 aag agc tgg aaa tcc att gtg gtt aca ag  gtaggaacag agttttaaac      83389
Lys Ser Trp Lys Ser Ile Val Val Thr Arg
    2265            2270 ttgtacaaag tttaatcatt tcaaattttg gcattgtttt aaaagacaac actattctgg  83449
ataacctggt ttcttcctga tgaacagttt gttggttgt tgttttaaca taatactttt    83509
tttctgttgt agtattgttg gagactttt cttccttgaa atgttaact tgtttaacct    83569 tgtttgggtg gcagggcatg aacagtgta gagctggggc tgggcgaagg agttggagct   83629
gtgtgtgcgt catgaagctg tcatcagcta tgagcctggg ctgaggctgc tcagcttctc  83689
ctgggtgcta ttttttctcca actgcagctt cagcttcttg attgtataat ttgcttcctc 83749 aagtatgagc caggaataat tgagctgtct tgtcacaatg tgtggcatac tggatctagg  83809
ctgtgctgca atgctttag agttatatcc tgggcaactt tctcttcaga tagccccaag   83869
agatgaattc agcaccagct ttgatgtttt actagcttct gctttctggt acttgatttt  83929
ctcccacccc gaacacatgg gattccaacc tgtgaaacta attttgtgg ctatgaaaga   83989 ggtagtggta gtttatgagt aaacattcag tctgttgcca ctatcatcat gtgtggttca  84049
tcatgactgt gatgagtagg taaaaggctc tttgtgtcat tctcatttcc aattttaagc  84109
agctgcttca aggagtctgg aagtcattga ccagtgggat cctgcctgtg tcttttccca  84169
ttaaagccat cctgtatgaa gtggtatcct ttaccatcta gcacatctgc cgcccccatt  84229
tcaaaaggca tactcatctt tatctcaaca ttctcataca gttccttatg tccatgcacc  84289
```

```
tccaatgtcc cctttgatgt cttttgaggtt ttcatcttcc atgtctgcta tttggaatgg    84349
tcttgatggg aggcaagata gtgatcacta caactaggat gggagtctta gtaccgtgag    84409
gctacagcaa gtcccacaga gggcctgctg cactgtactt gcctctgtca accaagtcta    84469
aggagaaaga ttaagcaggc atattaaagg acagcccaga tggacatgaa gtcctggagg    84529
aggccttggt tcctgtccta atactaaacc tagagtaccc agaatccaca cttctccact    84589
ctagctctca cttttcccat ctacacactg ggaaaaatta ttctgtcaga aagccagtgt    84649
caaggtgaga acaaataaca aatgtgatga tatggagtgg gagaaggggt ctcttctact    84709
gtcttattgg accctagcag tggctctgag ccagcagtcc tgtcagttga tttcttggtc    84769
gttcctttgt tttcttctat aatcacatgt ggactcagaa tgaattttga gttactctga    84829
aatctattta ttcaacagat atttacttag tacctcctat tgccagactc tgctttatgt    84889
tggatattat ttttaaaag cccaccttgc ctagatttcc tcaaggacc aggtggcttc    84949 cctggttttg aaagacccta attcttacta tgatcttaag taaattatat cctttctgtg    85009
ggctcaagtt cttttctaaga gggctctttg gggctacaaa agaaattgtt agtgcaaaaa    85069
gagtttataa ggtttataaa tggttagtag aggtgatgat gatatttaac cataattgaa    85129
gatgactttg catttttagat catatacgtg ttttttcgtct gagaacgata caggtcactg    85189
agcataccat aagccttcag taaatcattt gcagaagaca ttgcagaaga cataagtcta    85249
agtagaaatc tcttgacaga gagaaggctc gttttgatcc ttgacctcaa atttaggttc    85309
cctaaatcca ttaaaaaga gaaagaaaaa gaaaaaaagt tactaaagtt taaatctggg    85369
aggattatat acccttctca ataaagcagt ttagagagat ctcttttggg acccatgaca    85429
caggtcttgc tcatgctgac atctttatag ttgctttatt atttattcaa caaacttagt    85489
aacacgtatt ctatgtcagg cctttttcctg actactggga caaaccaggg tgatgtgggg    85549
gctgttttag atagggtgat cagaggaggc ctctctgttt gggtggcttt tgaatagaaa    85609
attagatgaa gtgaaggagt aagcttctga tatttcactg tttacttgtg gtagatctgt    85669
gataatctct gtcaggttaa aaacattccc ttctaatcta agtttctaag atctatcaaa    85729
agctgtttga atatatttag acaatcataa ttttcctttc ttgtattatc ctagcagatt    85789
ttgttgccaa agctatactg gccatttaa cttagaatgc agtctttcta ttcatttctc    85849
tggaaaagtt tggatattgt aagcattatt tttcttaagg tatgatgaac ctgcagaact    85909
gtttggttca attatgaatt tttttttttct ggagtctgta tttttttgaa ctattaatca    85969 tttcttaat gattataaat ctattcagat ttttacaagc tttatccctc tcccatcata    86029
cactattttt cttaccccatg cttttgcaca atttttttcct ctcccttagt gttttcctac    86089
ctagatacct cctatgtgtg tctgtgtatg tgagaaaagc ttttattttg ccatctttat    86149
atttctaaga atatctagta atacagaatt ttatattctg aagaattta ctttgcattt    86209 tcttattttg tgattgaaaa aaggtattaa ttttaaaatg gtcaaatcag gctccatcct    86269
tggaaaatac ccaaatcctt tattttgatt gggccatctg ttaattaggg ataccttatc    86329
tcttgccacc actttttaat gctaaataaa tatgtagcta aaactttgac tagaagaaac    86389
agtaaaataa gatattcttg cttatttta gtacagttat ttgaactgac ttttaaatca    86449
gtgacataaa ttatttgcca tgtctatact tttttttcctt atactttta g atg tat    86506
                                                           Met Tyr
                                                           2275 gaa acc aag tta aaa gaa ttg gaa act gat att gcc aaa aaa aat          86551
Glu Thr Lys Leu Lys Glu Leu Glu Thr Asp Ile Ala Lys Lys Asn
      2280                2285                2290
```

| | |
|---|---|
| caa agc att act gac ctt aaa cag ctt gta aaa gaa gca aca gag<br>Gln Ser Ile Thr Asp Leu Lys Gln Leu Val Lys Glu Ala Thr Glu<br>          2295                2300                2305 | 86596 |
| aga gaa caa aaa gtt aac aaa tac aat gaa gac ctt gaa caa cag<br>Arg Glu Gln Lys Val Asn Lys Tyr Asn Glu Asp Leu Glu Gln Gln<br>          2310                2315                2320 | 86641 |
| gtaagtaacg taattttct ttacatgata aataatgca taatatcgca agatgttcct | 86701 |
| tgcattgtct tatatagata aaaatggact ctattaagaa gacccatcta actgaagggc | 86761 |
| accccattca cccatttgct taagccagaa actttggatc atcaacgact tcattctttt | 86821 |
| cattctccac attttctatc attaaatcat gtcagctcta ttttcaaact atatcctaaa | 86881 |
| tatgaccact tcttggtatc ttgagacatc actaccagtc ttgtccaagc tattgtttta | 86941 |
| tacctgaata actgcaataa tttccaagct ggtatctcag cttccactct tggattattt | 87001 |
| caccctattt ctatttctgg gctgtctcca cacagttgcc aggtaaccct tttaaaacat | 87061 |
| aaagcacatc acaaagcaca aagtcctatc ctcagaatct tccagtggtt ctccatcacc | 87121 |
| ctaaaataaa acttaaaagt tctttcata tcccaaaaca acatatgagg tctggcaccc | 87181 |
| agttttcttc ccaatctcat cttctactac ttttcccttc atttcattca caatgttta | 87241 |
| accacagtaa ccttctttca gtactttaaa caatccaaac tcgtttaagc gtcaagtcct | 87301 |
| tatacttgtt tcctttgttt agaatactgt tcacccaaat attctcatag cttgctccca | 87361 |
| gacttcatgt ctctgctgaa atagaggctc cttagagaga ccttccctaa ccctaaccct | 87421 |
| aaccctatac tacttgccat cactctttat cctcttaccc tggattattt tttcttgata | 87481 |
| gctcttccta ccatctggca ctatattaca tcatatcata ttaaacacac attctttgtg | 87541 |
| cttccccact aaacaaggac catgcaagat ggaacattgc cattttgttc actgctgtta | 87601 |
| gcctctgtgc ctaggacaat gccagttatg cagtagttac tcaatacttg ttgaatgaat | 87661 |
| ggtgaataga acatagaaat ttgcctatgc gtgcttttga aaaccatatt ttaatattac | 87721 |
| gctttgttaa aaatgtgtat cttataaat cctcatattt ccatggcaaa ccttatcttc | 87781 |
| taactttca ttgtcctcaa ag att aag att ctt aaa cat gtt cct gaa<br>              Ile Lys Ile Leu Lys His Val Pro Glu<br>                                      2325 | 87830 |
| ggt gct gag aca gag caa ggc ctt aaa cgg gag ctt caa gtt ctt<br>Gly Ala Glu Thr Glu Gln Gly Leu Lys Arg Glu Leu Gln Val Leu<br>2330                2335                2340 | 87875 |
| ag    gtacatcatg tattcatatg actactttgt ttttttcttt aaaaaaaaaa<br>Arg<br>2345 | 87927 |
| ttattagttt ttatatactc cgaattgcta caactagaga caagcatttt tcgactttac | 87987 |
| tgcctaacag gctattagg tccttatttc ttccctctaa tgctaatcac tctttttcat | 88047 |
| aatacacact agaaaaaaag gataaaccca actctaagtt tccagtttgt aatttagttt | 88107 |
| aaactttct aagagcatag aatgagttaa accttagctt cccagaggaa aatactaatg | 88167 |
| aaagagaaca agtaattttt ttactttcag gggtctctgt agcctgcttt cattaagctc | 88227 |
| ctcttataac gaaaccacac ttgcaaatgc catcaggtca gatattaaga aaaacgtgaa | 88287 |
| ggcttttgta ttccaggctt tttgtttgag aatggtgaca ttgtagcatt gagagtaaat | 88347 |
| gtttacttcg ataaaggcta gcttgttctg attactgtac atcactagtt cataagaaat | 88407 |
| gcccatatat tttatgaagc aatatctgct ttatttttt aacacattat cattgtgttc | 88467 |
| tag a tta gct aat cat cag ctg gat aaa gag aaa gca gaa tta atc<br>    Leu Ala Asn His Gln Leu Asp Lys Glu Lys Ala Glu Leu Ile | 88513 |

|  |  |
|---|---|
| cat cag ata gaa gct aac aag gac caa agt gga gct gaa agc acc<br>His Gln Ile Glu Ala Asn Lys Asp Gln Ser Gly Ala Glu Ser Thr<br>               2360                            2365                     2370 | 88558 |
| ata cct g gtaatgtatt ttaaaaaaca tgttagctac ccccaagttt tgaatttgg<br>Ile Pro<br>2375 | 88615 |
| gtttgccttt tttttttttt tttggctcag atttctgatc attgtctccc tgtaaaatcg | 88675 |
| aattcctgat aagctttggg tcttttgtct ctctgtgcta ttaatataaa aatattccca | 88735 |
| tttttctctt tgtgttgttt atactataga gtagcaagta cccaagtgtt cttctctttg | 88795 |
| ttctccatct gggtgttaca gatttaatca caatacagtg ctaagcaatg aatactaaat | 88855 |
| ctgttgcttc cagtttctaa gtataggctc tttcaagtcc tctgaacatt tttaaaaact | 88915 |
| gcaaataagt aaatactgcc tatatttttt tccgtttaca aagtaaaaag aaaatctttc | 88975 |
| tgctcccttc cattcccatt caaaagtgat tactaatcat tcctcattcc tgcatataca | 89035 |
| tacacacata ttttgtatac atatatatca cacatatgca tacatgtgtt tgtatgttca | 89095 |
| tatgtacaat gtacatatcc tcattatttg tggattctgt attttctaaa tcacctcctc | 89155 |
| actaaagtgt gtatgtaatc ccaaatcaac actcgcagca catttgcaaa catccacaga | 89215 |
| gccttggaaa gtttgaataa tccaacctac atgtccccag cagaagtcca acaaggcagt | 89275 |
| gctcagtatc ctcatttcag ttttcataga gaaatgagca gaggatggag acagtagagg | 89335 |
| gcagcacagc atagtgcaag aagctgtggc tctgggcct ggtggaaggg atttgaatcc | 89395 |
| caattctgag gcttgttact gctctagcct taggagagtc atgtaacact tctgaatctt | 89455 |
| gttttcttat gtaaataaat agaatttacc aggatgagtt atctttagga tttaagatta | 89515 |
| tcatctgtgt gagatatgta ggtgtatgta tatatatgcg tgtatgtata tatatgcgtg | 89575 |
| tatgtatata tatgcatgtc tgtacatatt tcccgtagca gcagtggttt gatattcact | 89635 |
| aattgggcta actttataga ccaaaactac tatggataga gaatactttg tttgcattta | 89695 |
| cgtatatata ttttcttggc aagtaacata aaattgaact aatactatac acatttctag | 89755 |
| catatttgcc tttaacagtt tatcatggac atcttttgag gtctgttcat aaattatctc | 89815 |
| atccatttaa taattccata gtgtattatt gcatgtataa gcacatcgaa ccatttatgt | 89875 |
| tttgatggat atttagtttg cttccaagtt tctgcttcta taaatatga ttaatctatt | 89935 |
| gacctaatta tgccattgtg ataggatgat agagatgcca ttctctccaa aggattatac | 89995 |
| caatttatat ctgaactatc tttgactatc tcttgtagct ttttcagtat gctatgtagt | 90055 |
| cctattacta atttgtaata aaagccatca tgtgtgagtt gtactagaca ctatgctaat | 90115 |
| tgccttacaa gcattctata tttacaacca tatatgatag gtattactgt ctccattta | 90175 |
| tgtgataaac aaattcaaag tggttaagta accattccct aagccagcta ggaaatagag | 90235 |
| gcaggattaa aatctaaatg tatgaaactc cacagctcct tggcattcct agtccttaac | 90295 |
| ccgctatgct atgctacgtc ttggtaacta aaagtacata ttaaatactc tcaaaatatg | 90355 |
| tctcatagca gccagcttgg tatgtacact agacacagta ttaatgctgt tgatgtgagg | 90415 |
| aaaatttat aattttcctt ccatccatat actaaccagg cccaacagtg cttagcttct | 90475 |
| gagatcagag atcaggtgca tgtgcattaa gggtcatatg gccatagata gttctctaat | 90535 |
| cttttccattc ctcagtttct aagggaatt tctgaaccct caaaattcct tatttcctaa | 90595 |
| gtagacagat tacctgtcat ttttcaaaga ttaaggctta agatcaaacc agaactgttt | 90655 |
| tggaaattct aaatcactgt ctatataaat ggcaagataa cttttaagat atttatacca | 90715 |

```
agcccagtac agtagcacac cacacctgta atcccagcac tttgggaggc tgaagtgggt    90775
ggatcacatg aggtcaggag ttcgagacca ctctggccaa catggtgaaa ccctgtctct    90835
actaaaaata taaaaattag ccaggcatgg tggcacttgc ctgttatccc agctacaagg    90895
gaggctaagg caggagaatc gctttaacct gggaggcagt ggttgttgca gtgagccaag    90955
attgcaccac tgcactctag cctgggcgac agagtgagac tgtctcaaaa aaaaaaaaa    91015
aaaaaaagat acttgtccca gccatgaaaa tgtttgctgc cccttacttt cgcaaacttt    91075
tagtatttta ttattttca atggctgtaa aatatgactt attaaatgta gtataatata    91135
aagaaaagag atatctagca aagatagcat taaagcaaaa atcctatttg cctgctgata    91195
aagttagagg tgttaacttg gagggtgaat ccaataaatt agaacttttg tgctatattt    91255
ggagactttt gttttcctac caaagtatca gggctatgtc ttacttatct ttgtattaca    91315
cagcctgcat gacacgtttt gcacatagta attgcacagt aaatgtgtaa taacctacat    91375
ggaatagcca gtgttgtgtt ggatagcggg agcatttggc tagcttatgg ttatagtccc    91435
ttacccaaca gtctgctttt cttctgttgt acttttagta cctaacaagt ttccctggct    91495
ttaggatttt ttccatgtaa aatttctatc atgtgaagaa aaaataactt ggcctacact    91555
tctaatacct agcacatacc tctttctgcc tgctatgaaa ttataatact tgatggaggg    91615
aggcagcatt aagtgtttac atcctgaagt atttcagcca taacatccag tgttttccag    91675
gttctaggtt tcataaaatg tatctctgtt ctctagaaca aatccattac cttgaactca    91735
ttcgtagtgg gaaaagctg agtctaattt gtatgacttt ttcaacag at  gct gat    91791
                                                   Asp Ala Asp caa cta aag gaa aaa ata aaa gat cta gag aca  cag ctc aaa atg        91836
Gln Leu Lys Glu Lys Ile Lys Asp Leu Glu Thr  Gln Leu Lys Met
2380            2385                         2390 tca gat cta gaa aag cag cat ttg aag gtaatattta attatatttt            91883
Ser Asp Leu Glu Lys Gln His Leu Lys
2395            2400 agtatcgttt tgtgaaaaca gctgttgaaa actattttca ttaccatctt taactacgta    91943
tcctaaaaaa ttcagtaata acatcttata tttgaccttt atattgcaaa gttaattatg    92003
ttcatctgac tattcctaac atattagagt taacaaaaaa ttcagactca acataggatt    92063
aagtagtaaa tttattttt aattgtaaca aatatatgcc attagtatgt tcttaagttt    92123
tgggtcacat tggcaacagt gtctttattt tttttttgaa attcttttca ggaatcctaa    92183
ggttatagtt cccttaaaaa aatatttgct gttttacctc ttttaagact gtaaacagga    92243
caaaaaggca tggatatgag aattagctag tgatcactgg ctattctaaa tagtcactaa    92303
ggcttgaatt gtctcttcac cagatgcctg tcagaagtcc caaggtttc cctgatcata     92363
ttaataactt tataaaaaat tgatcattat tcattaaata ttagatatta gtaaggaaaa    92423
tataaatgaa gtctaaacca aaactcttaa ccagactaac ttcaatgtta tgaatcacaa    92483
aatctttttg attgattgct ctattgacaa gctcttatat gctttagag aaagattaag     92543
tcccattata agagatgata aattttagtc aaagactaga acacaactta cagaatacat    92603
aactggactt gacagttaac aacttagtta tttacactgt acaatggaac aaagaaaaat    92663
cttaattctt ctgcctttat tgctgtattt gaccattcag gaatactttg gctttcatat    92723
ttacaattaa atctccttgt tcaaacgtaa aatatgtata tttcctatat gcaactttta    92783
aagataatgt ttccattag gag gaa  ata aag aag ctg aaa  aaa gaa ctg      92832
                         Glu Glu  Ile Lys Lys Leu Lys  Lys Glu Leu
                         2405                    2410
```

```
gaa aat ttt gat cct tca ttt ttt gaa gaa att gaa gat ctt aag      92877
Glu Asn Phe Asp Pro Ser Phe Phe Glu Glu Ile Glu Asp Leu Lys
    2415                2420                2425 tat aat tac aag gaa gaa gtg aag aag aat att ctc tta gaa gag      92922
Tyr Asn Tyr Lys Glu Glu Val Lys Lys Asn Ile Leu Leu Glu Glu
    2430                2435                2440 aag gta aaa aaa ctt tca gaa caa ttg gga gtt gaa tta act agc      92967
Lys Val Lys Lys Leu Ser Glu Gln Leu Gly Val Glu Leu Thr Ser
    2445                2450                2455 cct gtt gct gct tct gaa gag ttt gaa gat gaa gaa gaa agt cct      93012
Pro Val Ala Ala Ser Glu Glu Phe Glu Asp Glu Glu Glu Ser Pro
    2460                2465                2470 gtt aat ttc ccc att tac taa aggtcaccta taaactttgt ttcatttaac     93063
Val Asn Phe Pro Ile Tyr
    2475 tatttattaa ctttataagt taaatatact tggaaataag cagttctccg aactgtagta 93123 tttccttctc actaccttgt acctttatac ttagattgga attcttaata aataaaatta 93183 tatgaaattt tcaacttatt                                            93203

<210> SEQ ID NO 2
<211> LENGTH: 7972
<212> TYPE: DNA
<213> ORGANISM: Homo sapiens
<220> FEATURE:
<221> NAME/KEY: CDS
<222> LOCATION: (345)..(7781)

<400> SEQUENCE: 2
atttgaagtc ctcgttccac gccttctcat catcctgaac accgagctct gggactccgg   60
cggagaatct aaacgtaaag catcacccac ggtcgtgaac tgtaggctct cctggcatcc  120
gggatcttat tctggccttg gcggagttgg ggatggtgtc gcctagcagc cgctgccgct  180
ttggcttgct cgggaccatt tggctggacc cagagtccgc gtggaaccgc gatagggatc  240
tgtcagggcc gcgggccggg tccagcttgg tggttgcggt agtgagaggc ctccgctggt  300
tgccaggctt ggtctagagg tggagcacag tgaaagaatt caag atg cca cct aat  356
                                                Met Pro Pro Asn
                                                1 ata aac tgg aaa gaa ata atg aaa gtt gac cca gat gac ctg ccc cgt    404
Ile Asn Trp Lys Glu Ile Met Lys Val Asp Pro Asp Asp Leu Pro Arg
5               10                  15                  20 caa gaa gaa ctg gca gat aat tta ttg att tcc tta tcc aag gtg gaa    452
Gln Glu Glu Leu Ala Asp Asn Leu Leu Ile Ser Leu Ser Lys Val Glu
            25                  30                  35 gta aat gag cta aaa agt gaa aag caa gaa aat gtg ata cac ctt ttc    500
Val Asn Glu Leu Lys Ser Glu Lys Gln Glu Asn Val Ile His Leu Phe
        40                  45                  50 aga att act cag tca cta atg aag atg aaa gct caa gaa gtg gag ctg    548
Arg Ile Thr Gln Ser Leu Met Lys Met Lys Ala Gln Glu Val Glu Leu
    55                  60                  65 gct ttg gaa gaa gta gaa aaa gct gga gaa gaa caa gca aaa ttt gaa    596
Ala Leu Glu Glu Val Glu Lys Ala Gly Glu Glu Gln Ala Lys Phe Glu
70                  75                  80 aat caa tta aaa act aaa gta atg aaa ctg gaa aat gaa ctg gag atg    644
Asn Gln Leu Lys Thr Lys Val Met Lys Leu Glu Asn Glu Leu Glu Met
85                  90                  95                  100 gct cag cag tct gca ggt gga cga gat act cgg ttt tta cgt aat gaa    692
Ala Gln Gln Ser Ala Gly Gly Arg Asp Thr Arg Phe Leu Arg Asn Glu
                105                 110                 115
```

```
att tgc caa ctt gaa aaa caa tta gaa caa aaa gat aga gaa ttg gag      740
Ile Cys Gln Leu Glu Lys Gln Leu Glu Gln Lys Asp Arg Glu Leu Glu
        120                 125                 130 gac atg gaa aag gag ttg gag aaa gag aag aaa gtt aat gag caa ttg      788
Asp Met Glu Lys Glu Leu Glu Lys Glu Lys Lys Val Asn Glu Gln Leu
    135                 140                 145 gct ctt cga aat gag gag gca gaa aat gaa aac agc aaa tta aga aga      836
Ala Leu Arg Asn Glu Glu Ala Glu Asn Glu Asn Ser Lys Leu Arg Arg
150                 155                 160 gag aac aaa cgt cta aag aaa aag aat gaa caa ctt tgt cag gat att      884
Glu Asn Lys Arg Leu Lys Lys Lys Asn Glu Gln Leu Cys Gln Asp Ile
165                 170                 175                 180 att gac tac cag aaa caa ata gat tca cag aaa gaa aca ctt tta tca      932
Ile Asp Tyr Gln Lys Gln Ile Asp Ser Gln Lys Glu Thr Leu Leu Ser
                185                 190                 195 aga aga ggg gaa gac agt gac tac cga tca cag ttg tct aaa aaa aac      980
Arg Arg Gly Glu Asp Ser Asp Tyr Arg Ser Gln Leu Ser Lys Lys Asn
                200                 205                 210 tat gag ctt atc caa tat ctt gat gaa att cag act tta aca gaa gct     1028
Tyr Glu Leu Ile Gln Tyr Leu Asp Glu Ile Gln Thr Leu Thr Glu Ala
            215                 220                 225 aat gag aaa att gaa gtt cag aat caa gaa atg aga aaa aat tta gaa     1076
Asn Glu Lys Ile Glu Val Gln Asn Gln Glu Met Arg Lys Asn Leu Glu
230                 235                 240 gag tct gta cag gaa atg gag aag atg act gat gaa tat aat aga atg     1124
Glu Ser Val Gln Glu Met Glu Lys Met Thr Asp Glu Tyr Asn Arg Met
245                 250                 255                 260 aaa gct att gtg cat cag aca gat aat gta ata gat cag tta aaa aaa     1172
Lys Ala Ile Val His Gln Thr Asp Asn Val Ile Asp Gln Leu Lys Lys
                265                 270                 275 gaa aac gat cat tat caa ctt caa gtg cag gag ctt aca gat ctt ctg     1220
Glu Asn Asp His Tyr Gln Leu Gln Val Gln Glu Leu Thr Asp Leu Leu
                280                 285                 290 aaa tca aaa aat gaa gaa gat gat cca att atg gta gct gtc aat gca     1268
Lys Ser Lys Asn Glu Glu Asp Asp Pro Ile Met Val Ala Val Asn Ala
            295                 300                 305 aaa gta gaa gaa tgg aag cta att ttg tct tct aaa gat gat gaa att     1316
Lys Val Glu Glu Trp Lys Leu Ile Leu Ser Ser Lys Asp Asp Glu Ile
310                 315                 320 att gag tat cag caa atg tta cat aac cta agg gag aaa ctt aag aat     1364
Ile Glu Tyr Gln Gln Met Leu His Asn Leu Arg Glu Lys Leu Lys Asn
325                 330                 335                 340 gct cag ctt gat gct gat aaa agt aat gtt atg gct cta cag cag ggt     1412
Ala Gln Leu Asp Ala Asp Lys Ser Asn Val Met Ala Leu Gln Gln Gly
                345                 350                 355 ata cag gaa cga gac agt caa att aag atg ctc acc gaa caa gta gaa     1460
Ile Gln Glu Arg Asp Ser Gln Ile Lys Met Leu Thr Glu Gln Val Glu
                360                 365                 370 caa tat aca aaa gaa atg gaa aag aat act tgt att att gaa gat ttg     1508
Gln Tyr Thr Lys Glu Met Glu Lys Asn Thr Cys Ile Ile Glu Asp Leu
            375                 380                 385 aaa aat gag ctc caa aga aac aaa ggt gct tca acc ctt tct caa cag     1556
Lys Asn Glu Leu Gln Arg Asn Lys Gly Ala Ser Thr Leu Ser Gln Gln
390                 395                 400 act cat atg aaa att cag tca acg tta gac att tta aaa gag aaa act     1604
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa     1652
Lys Glu Ala Glu Arg Thr Ala Glu Leu Ala Glu Ala Asp Ala Arg Glu
```

-continued

```
                425                 430                 435
aag gat aaa gaa tta gtt gag gct ctg aag agg tta aaa gat tat gaa      1700
Lys Asp Lys Glu Leu Val Glu Ala Leu Lys Arg Leu Lys Asp Tyr Glu
            440                 445                 450 tcg gga gta tat ggt tta gaa gat gct gtc gtt gaa ata aag aat tgt      1748
Ser Gly Val Tyr Gly Leu Glu Asp Ala Val Val Glu Ile Lys Asn Cys
                455                 460                 465 aaa aac caa att aaa ata aga gat cga gag att gaa ata tta aca aag      1796
Lys Asn Gln Ile Lys Ile Arg Asp Arg Glu Ile Glu Ile Leu Thr Lys
        470                 475                 480 gaa atc aat aaa ctt gaa ttg aag atc agt gat ttc ctt gat gaa aat      1844
Glu Ile Asn Lys Leu Glu Leu Lys Ile Ser Asp Phe Leu Asp Glu Asn
485                 490                 495                 500 gag gca ctt aga gag cgt gtg ggc ctt gaa cca aag aca atg att gat      1892
Glu Ala Leu Arg Glu Arg Val Gly Leu Glu Pro Lys Thr Met Ile Asp
                505                 510                 515 tta act gaa ttt aga aat agc aaa cac tta aaa cag cag cag tac aga      1940
Leu Thr Glu Phe Arg Asn Ser Lys His Leu Lys Gln Gln Gln Tyr Arg
        520                 525                 530 gct gaa aac cag att ctt ttg aaa gag att gaa agt cta gag gaa gaa      1988
Ala Glu Asn Gln Ile Leu Leu Lys Glu Ile Glu Ser Leu Glu Glu Glu
    535                 540                 545 cga ctt gat ctg aaa aaa aaa att cgt caa atg gct caa gaa aga gga      2036
Arg Leu Asp Leu Lys Lys Lys Ile Arg Gln Met Ala Gln Glu Arg Gly
550                 555                 560 aaa aga agt gca act tca gga tta acc act gag gac ctg aac cta act      2084
Lys Arg Ser Ala Thr Ser Gly Leu Thr Thr Glu Asp Leu Asn Leu Thr
565                 570                 575                 580 gaa aac att tct caa gga gat aga ata agt gaa aga aaa ttg gat tta      2132
Glu Asn Ile Ser Gln Gly Asp Arg Ile Ser Glu Arg Lys Leu Asp Leu
                585                 590                 595 ttg agc ctc aaa aat atg agt gaa gca caa tca aag aat gaa ttt ctt      2180
Leu Ser Leu Lys Asn Met Ser Glu Ala Gln Ser Lys Asn Glu Phe Leu
            600                 605                 610 tca aga gaa cta att gaa aaa gaa aga gat tta gaa agg agt agg aca      2228
Ser Arg Glu Leu Ile Glu Lys Glu Arg Asp Leu Glu Arg Ser Arg Thr
        615                 620                 625 gtg ata gcc aaa ttt cag aat aaa tta aaa gaa tta gtt gaa gaa aat      2276
Val Ile Ala Lys Phe Gln Asn Lys Leu Lys Glu Leu Val Glu Glu Asn
630                 635                 640 aag caa ctt gaa gaa ggt atg aaa gaa ata ttg caa gca att aag gaa      2324
Lys Gln Leu Glu Glu Gly Met Lys Glu Ile Leu Gln Ala Ile Lys Glu
645                 650                 655                 660 atg cag aaa gat cct gat gtt aaa gga gga gaa aca tct cta att atc      2372
Met Gln Lys Asp Pro Asp Val Lys Gly Gly Glu Thr Ser Leu Ile Ile
                665                 670                 675 cct agc ctt gaa aga cta gtt aat gct ata gaa tca aag aat gca gaa      2420
Pro Ser Leu Glu Arg Leu Val Asn Ala Ile Glu Ser Lys Asn Ala Glu
            680                 685                 690 gga atc ttt gat gcg agt ctg cat ttg aaa gcc caa gtt gat cag ctt      2468
Gly Ile Phe Asp Ala Ser Leu His Leu Lys Ala Gln Val Asp Gln Leu
        695                 700                 705 acc gga aga aat gaa gaa tta aga cag gag ctc agg gaa tct cgg aaa      2516
Thr Gly Arg Asn Glu Glu Leu Arg Gln Glu Leu Arg Glu Ser Arg Lys
710                 715                 720 gag gct ata aat tat tca cag cag ttg gca aaa gct aat tta aag ata      2564
Glu Ala Ile Asn Tyr Ser Gln Gln Leu Ala Lys Ala Asn Leu Lys Ile
725                 730                 735                 740 gac cat ctt gaa aaa gaa act agt ctt tta cga caa tca gaa gga tcg      2612
```

```
                Asp His Leu Glu Lys Glu Thr Ser Leu Leu Arg Gln Ser Glu Gly Ser
                            745                 750                 755 aat gtt gtt ttt aaa gga att gac tta cct gat ggg ata gca cca tct      2660
Asn Val Val Phe Lys Gly Ile Asp Leu Pro Asp Gly Ile Ala Pro Ser
            760                 765                 770 agt gcc agt atc att aat tct cag aat gaa tat tta ata cat ttg tta      2708
Ser Ala Ser Ile Ile Asn Ser Gln Asn Glu Tyr Leu Ile His Leu Leu
            775                 780                 785 cag gaa cta gaa aat aaa gaa aaa aag tta aag aat tta gaa gat tct      2756
Gln Glu Leu Glu Asn Lys Glu Lys Lys Leu Lys Asn Leu Glu Asp Ser
        790                 795                 800 ctt gaa gat tac aac aga aaa ttt gct gta att cgt cat caa caa agt      2804
Leu Glu Asp Tyr Asn Arg Lys Phe Ala Val Ile Arg His Gln Gln Ser
805                 810                 815                 820 ttg ttg tat aaa gaa tac cta agt gaa aag gag acc tgg aaa aca gaa      2852
Leu Leu Tyr Lys Glu Tyr Leu Ser Glu Lys Glu Thr Trp Lys Thr Glu
                825                 830                 835 tct aaa aca ata aaa gag gaa aag aga aaa ctt gag gat caa gtc caa      2900
Ser Lys Thr Ile Lys Glu Glu Lys Arg Lys Leu Glu Asp Gln Val Gln
            840                 845                 850 caa gat gct ata aaa gta aaa gaa tat aat aat ttg ctc aat gct ctt      2948
Gln Asp Ala Ile Lys Val Lys Glu Tyr Asn Asn Leu Leu Asn Ala Leu
            855                 860                 865 cag atg gat tcg gat gaa atg aaa aaa ata ctt gca gaa aat agt agg      2996
Gln Met Asp Ser Asp Glu Met Lys Lys Ile Leu Ala Glu Asn Ser Arg
        870                 875                 880 aaa att act gtt ttg caa gtg aat gaa aaa tca ctt ata agg caa tat      3044
Lys Ile Thr Val Leu Gln Val Asn Glu Lys Ser Leu Ile Arg Gln Tyr
885                 890                 895                 900 aca acc tta gta gaa ttg gag cga caa ctt aga aaa gaa aat gag aag      3092
Thr Thr Leu Val Glu Leu Glu Arg Gln Leu Arg Lys Glu Asn Glu Lys
                905                 910                 915 caa aag aat gaa ttg ttg tca atg gag gct gaa gtt tgt gaa aaa att      3140
Gln Lys Asn Glu Leu Leu Ser Met Glu Ala Glu Val Cys Glu Lys Ile
            920                 925                 930 ggg tgt ttg caa aga ttt aag gaa atg gcc att ttc aag att gca gct      3188
Gly Cys Leu Gln Arg Phe Lys Glu Met Ala Ile Phe Lys Ile Ala Ala
            935                 940                 945 ctc caa aaa gtt gta gat aat agt gtt tct ttg tct gaa cta gaa ctg      3236
Leu Gln Lys Val Val Asp Asn Ser Val Ser Leu Ser Glu Leu Glu Leu
        950                 955                 960 gct aat aaa cag tac aat gaa ctg act gct aag tac agg gac atc ttg      3284
Ala Asn Lys Gln Tyr Asn Glu Leu Thr Ala Lys Tyr Arg Asp Ile Leu
965                 970                 975                 980 caa aaa gat aat atg ctt gtt caa aga aca agt aac ttg gaa cac ctg      3332
Gln Lys Asp Asn Met Leu Val Gln Arg Thr Ser Asn Leu Glu His Leu
                985                 990                 995 gag tgt gaa aac atc tcc tta aaa gaa  caa gtg gag tct ata   aat      3377
Glu Cys Glu Asn Ile Ser Leu Lys Glu  Gln Val Glu Ser Ile   Asn
            1000                1005                1010 aaa gaa ctg gag  att acc aag gaa aaa  ctt cac act att gaa  caa      3422
Lys Glu Leu Glu  Ile Thr Lys Glu Lys  Leu His Thr Ile Glu  Gln
            1015                1020                1025 gcc tgg gaa cag  gaa act aaa tta ggt  aat gaa tct agc atg  gat      3467
Ala Trp Glu Gln  Glu Thr Lys Leu Gly  Asn Glu Ser Ser Met  Asp
            1030                1035                1040 aag gca aag aaa  tca ata acc aac agt  gac att gtt tcc att  tca      3512
Lys Ala Lys Lys  Ser Ile Thr Asn Ser  Asp Ile Val Ser Ile  Ser
            1045                1050                1055
```

| | | | | | | | | | | | | | | |
|---|---|---|---|---|---|---|---|---|---|---|---|---|---|---|
| aaa | aaa | ata | act | atg | ctg | gaa | atg | aag | gaa | tta | aat | gaa | agg | cag |
| Lys | Lys | Ile | Thr 1060 | Met | Leu | Glu | Met | Lys 1065 | Glu | Leu | Asn | Glu | Arg 1070 | Gln |

3557

| | | | | | | | | | | | | | | |
|---|---|---|---|---|---|---|---|---|---|---|---|---|---|---|
| cgg | gct | gaa | cat | tgt | caa | aaa | atg | tat | gaa | cac | tta | cgg | act | tcg |
| Arg | Ala | Glu | His 1075 | Cys | Gln | Lys | Met | Tyr 1080 | Glu | His | Leu | Arg | Thr 1085 | Ser |

3602

| | | | | | | | | | | | | | | |
|---|---|---|---|---|---|---|---|---|---|---|---|---|---|---|
| tta | aag | caa | atg | gag | gaa | cgt | aat | ttt | gaa | ttg | gaa | acc | aaa | ttt |
| Leu | Lys | Gln | Met 1090 | Glu | Glu | Arg | Asn | Phe 1095 | Glu | Leu | Glu | Thr | Lys 1100 | Phe |

3647

| | | | | | | | | | | | | | | |
|---|---|---|---|---|---|---|---|---|---|---|---|---|---|---|
| gct | gag | ctt | acc | aaa | atc | aat | ttg | gat | gca | cag | aag | gtg | gaa | cag |
| Ala | Glu | Leu | Thr 1105 | Lys | Ile | Asn | Leu | Asp 1110 | Ala | Gln | Lys | Val | Glu 1115 | Gln |

3692

| | | | | | | | | | | | | | | |
|---|---|---|---|---|---|---|---|---|---|---|---|---|---|---|
| atg | tta | aga | gat | gaa | tta | gct | gat | agt | gtg | agc | aag | gca | gta | agt |
| Met | Leu | Arg | Asp 1120 | Glu | Leu | Ala | Asp | Ser 1125 | Val | Ser | Lys | Ala | Val 1130 | Ser |

3737

| | | | | | | | | | | | | | | |
|---|---|---|---|---|---|---|---|---|---|---|---|---|---|---|
| gat | gct | gat | agg | caa | cgg | att | cta | gaa | tta | gag | aag | aat | gaa | atg |
| Asp | Ala | Asp | Arg 1135 | Gln | Arg | Ile | Leu | Glu 1140 | Leu | Glu | Lys | Asn | Glu 1145 | Met |

3782

| | | | | | | | | | | | | | | |
|---|---|---|---|---|---|---|---|---|---|---|---|---|---|---|
| gaa | cta | aaa | gtt | gaa | gtg | tca | aaa | ctg | aga | gag | att | tct | gat | att |
| Glu | Leu | Lys | Val 1150 | Glu | Val | Ser | Lys | Leu 1155 | Arg | Glu | Ile | Ser | Asp 1160 | Ile |

3827

| | | | | | | | | | | | | | | |
|---|---|---|---|---|---|---|---|---|---|---|---|---|---|---|
| gcc | aga | aga | caa | gtt | gaa | att | ttg | aat | gca | caa | caa | caa | tct | agg |
| Ala | Arg | Arg | Gln 1165 | Val | Glu | Ile | Leu | Asn 1170 | Ala | Gln | Gln | Gln | Ser 1175 | Arg |

3872

| | | | | | | | | | | | | | | |
|---|---|---|---|---|---|---|---|---|---|---|---|---|---|---|
| gac | aag | gaa | gta | gag | tcc | ctc | aga | atg | caa | ctg | cta | gac | tat | cag |
| Asp | Lys | Glu | Val 1180 | Glu | Ser | Leu | Arg | Met 1185 | Gln | Leu | Leu | Asp | Tyr 1190 | Gln |

3917

| | | | | | | | | | | | | | | |
|---|---|---|---|---|---|---|---|---|---|---|---|---|---|---|
| gca | cag | tct | gat | gaa | aag | tcg | ctc | att | gcc | aag | ttg | cac | caa | cat |
| Ala | Gln | Ser | Asp 1195 | Glu | Lys | Ser | Leu | Ile 1200 | Ala | Lys | Leu | His | Gln 1205 | His |

3962

| | | | | | | | | | | | | | | |
|---|---|---|---|---|---|---|---|---|---|---|---|---|---|---|
| aat | gtc | tct | ctt | caa | ctg | agt | gag | gct | act | gct | ctt | ggt | aag | ttg |
| Asn | Val | Ser | Leu 1210 | Gln | Leu | Ser | Glu | Ala 1215 | Thr | Ala | Leu | Gly | Lys 1220 | Leu |

4007

| | | | | | | | | | | | | | | |
|---|---|---|---|---|---|---|---|---|---|---|---|---|---|---|
| gag | tca | att | aca | tct | aaa | ctg | cag | aag | atg | gag | gcc | tac | aac | ttg |
| Glu | Ser | Ile | Thr 1225 | Ser | Lys | Leu | Gln | Lys 1230 | Met | Glu | Ala | Tyr | Asn 1235 | Leu |

4052

| | | | | | | | | | | | | | | |
|---|---|---|---|---|---|---|---|---|---|---|---|---|---|---|
| cgc | tta | gag | cag | aaa | ctt | gat | gaa | aaa | gaa | cag | gct | ctc | tat | tat |
| Arg | Leu | Glu | Gln 1240 | Lys | Leu | Asp | Glu | Lys 1245 | Glu | Gln | Ala | Leu | Tyr 1250 | Tyr |

4097

| | | | | | | | | | | | | | | |
|---|---|---|---|---|---|---|---|---|---|---|---|---|---|---|
| gct | cgt | ttg | gag | gga | aga | aac | aga | gca | aaa | cat | ctg | cgc | caa | aca |
| Ala | Arg | Leu | Glu 1255 | Gly | Arg | Asn | Arg | Ala 1260 | Lys | His | Leu | Arg | Gln 1265 | Thr |

4142

| | | | | | | | | | | | | | | |
|---|---|---|---|---|---|---|---|---|---|---|---|---|---|---|
| att | cag | tct | cta | cga | cga | cag | ttt | agt | gga | gct | tta | ccc | ttg | gca |
| Ile | Gln | Ser | Leu 1270 | Arg | Arg | Gln | Phe | Ser 1275 | Gly | Ala | Leu | Pro | Leu 1280 | Ala |

4187

| | | | | | | | | | | | | | | |
|---|---|---|---|---|---|---|---|---|---|---|---|---|---|---|
| caa | cag | gaa | aag | ttc | tcc | aaa | aca | atg | att | caa | cta | caa | aat | gac |
| Gln | Gln | Glu | Lys 1285 | Phe | Ser | Lys | Thr | Met 1290 | Ile | Gln | Leu | Gln | Asn 1295 | Asp |

4232

| | | | | | | | | | | | | | | |
|---|---|---|---|---|---|---|---|---|---|---|---|---|---|---|
| aaa | ctt | aag | ata | atg | caa | gaa | atg | aaa | aat | tct | caa | caa | gaa | cat |
| Lys | Leu | Lys | Ile 1300 | Met | Gln | Glu | Met | Lys 1305 | Asn | Ser | Gln | Gln | Glu 1310 | His |

4277

| | | | | | | | | | | | | | | |
|---|---|---|---|---|---|---|---|---|---|---|---|---|---|---|
| aga | aat | atg | gag | aac | aaa | aca | ttg | gag | atg | gaa | tta | aaa | tta | aag |
| Arg | Asn | Met | Glu 1315 | Asn | Lys | Thr | Leu | Glu 1320 | Met | Glu | Leu | Lys | Leu 1325 | Lys |

4322

| | | | | | | | | | | | | | | |
|---|---|---|---|---|---|---|---|---|---|---|---|---|---|---|
| ggc | ctg | gaa | gag | tta | ata | agc | act | tta | aag | gat | acc | aaa | gga | gcc |
| Gly | Leu | Glu | Glu 1330 | Leu | Ile | Ser | Thr | Leu 1335 | Lys | Asp | Thr | Lys | Gly 1340 | Ala |

4367

| | | | | | | | | | | | | | | |
|---|---|---|---|---|---|---|---|---|---|---|---|---|---|---|
| caa | aag | gta | atc | aac | tgg | cat | atg | aaa | ata | gaa | gaa | ctt | cgt | ctt |
| Gln | Lys | Val | Ile 1345 | Asn | Trp | His | Met | Lys 1350 | Ile | Glu | Glu | Leu | Arg 1355 | Leu |

4412

-continued

| | | |
|---|---|---|
| caa gaa ctt aaa cta aat cgg gaa tta gtc aag gat aaa gaa gaa<br>Gln Glu Leu Lys Leu Asn Arg Glu Leu Val Lys Asp Lys Glu Glu<br>1360     1365     1370 | 4457 | |
| ata aaa tat ttg aat aac ata att tct gaa tat gaa cgt aca atc<br>Ile Lys Tyr Leu Asn Asn Ile Ile Ser Glu Tyr Glu Arg Thr Ile<br>1375     1380     1385 | 4502 | |
| agc agt ctt gaa gaa gaa att gtg caa cag aac aag ttt cat gaa<br>Ser Ser Leu Glu Glu Glu Ile Val Gln Gln Asn Lys Phe His Glu<br>1390     1395     1400 | 4547 | |
| gaa aga caa atg gcc tgg gat caa aga gaa gtt gac ctg gaa cgc<br>Glu Arg Gln Met Ala Trp Asp Gln Arg Glu Val Asp Leu Glu Arg<br>1405     1410     1415 | 4592 | |
| caa cta gac att ttt gac cgt cag caa aat gaa ata cta aat gcg<br>Gln Leu Asp Ile Phe Asp Arg Gln Gln Asn Glu Ile Leu Asn Ala<br>1420     1425     1430 | 4637 | |
| gca caa aag ttt gaa gaa gct aca gga tca atc cct gac cct agt<br>Ala Gln Lys Phe Glu Glu Ala Thr Gly Ser Ile Pro Asp Pro Ser<br>1435     1440     1445 | 4682 | |
| ttg ccc ctt cca aat caa ctt gag atc gct cta agg aaa att aag<br>Leu Pro Leu Pro Asn Gln Leu Glu Ile Ala Leu Arg Lys Ile Lys<br>1450     1455     1460 | 4727 | |
| gag aac att cga ata att cta gaa aca cgg gca act tgc aaa tca<br>Glu Asn Ile Arg Ile Ile Leu Glu Thr Arg Ala Thr Cys Lys Ser<br>1465     1470     1475 | 4772 | |
| cta gaa gag aaa cta aaa gag aaa gaa tct gct tta agg tta gca<br>Leu Glu Glu Lys Leu Lys Glu Lys Glu Ser Ala Leu Arg Leu Ala<br>1480     1485     1490 | 4817 | |
| gaa caa aat ata ctg tca aga gac aaa gta atc aat gaa ctg agg<br>Glu Gln Asn Ile Leu Ser Arg Asp Lys Val Ile Asn Glu Leu Arg<br>1495     1500     1505 | 4862 | |
| ctt cga ttg cct gcc act gca gaa aga gaa aag ctc ata gct gag<br>Leu Arg Leu Pro Ala Thr Ala Glu Arg Glu Lys Leu Ile Ala Glu<br>1510     1515     1520 | 4907 | |
| cta ggc aga aaa gag atg gaa cca aaa tct cac cac aca ttg aaa<br>Leu Gly Arg Lys Glu Met Glu Pro Lys Ser His His Thr Leu Lys<br>1525     1530     1535 | 4952 | |
| att gct cat caa acc att gca aac atg caa gca agg tta aat caa<br>Ile Ala His Gln Thr Ile Ala Asn Met Gln Ala Arg Leu Asn Gln<br>1540     1545     1550 | 4997 | |
| aaa gaa gaa gta tta aag aag tat caa cgt ctt cta gaa aaa gcc<br>Lys Glu Glu Val Leu Lys Lys Tyr Gln Arg Leu Leu Glu Lys Ala<br>1555     1560     1565 | 5042 | |
| aga gag gag caa aga gaa att gtg aag aaa cat gag gaa gac ctt<br>Arg Glu Glu Gln Arg Glu Ile Val Lys Lys His Glu Glu Asp Leu<br>1570     1575     1580 | 5087 | |
| cat att ctt cat cac aga tta gaa cta cag gct gat agt tca cta<br>His Ile Leu His His Arg Leu Glu Leu Gln Ala Asp Ser Ser Leu<br>1585     1590     1595 | 5132 | |
| aat aaa ttc aaa caa acg gct tgg gat tta atg aaa cag tct ccc<br>Asn Lys Phe Lys Gln Thr Ala Trp Asp Leu Met Lys Gln Ser Pro<br>1600     1605     1610 | 5177 | |
| act cca gtt cct acc aac aag cat ttt att cgt ctg gct gag atg<br>Thr Pro Val Pro Thr Asn Lys His Phe Ile Arg Leu Ala Glu Met<br>1615     1620     1625 | 5222 | |
| gaa cag aca gta gca gaa caa gat gac tct ctt tcc tca ctc ttg<br>Glu Gln Thr Val Ala Glu Gln Asp Asp Ser Leu Ser Ser Leu Leu<br>1630     1635     1640 | 5267 | |
| gtc aaa cta aag aaa gta tca caa gat ttg gag aga caa aga gaa<br>Val Lys Leu Lys Lys Val Ser Gln Asp Leu Glu Arg Gln Arg Glu | 5312 | |

```
                1645                1650                1655
atc act gaa tta  aaa gta aaa gaa  ttt gaa aat atc aaa tta  cag        5357
Ile Thr Glu Leu  Lys Val Lys Glu  Phe Glu Asn Ile Lys Leu  Gln
            1660                1665                1670 ctt caa gaa aac  cat gaa gat gaa  gtg aaa aaa gta aaa gcg  gaa        5402
Leu Gln Glu Asn  His Glu Asp Glu  Val Lys Lys Val Lys Ala  Glu
            1675                1680                1685 gta gag gat tta  aag tat ctt ctg  gac cag tca caa aag gag  tca        5447
Val Glu Asp Leu  Lys Tyr Leu Leu  Asp Gln Ser Gln Lys Glu  Ser
            1690                1695                1700 cag tgt tta aaa  tct gaa ctt cag  gct caa aaa gaa gca aat  tca        5492
Gln Cys Leu Lys  Ser Glu Leu Gln  Ala Gln Lys Glu Ala Asn  Ser
            1705                1710                1715 aga gct cca aca  act aca atg aga  aat cta gta gaa cgg cta  aag        5537
Arg Ala Pro Thr  Thr Thr Met Arg  Asn Leu Val Glu Arg Leu  Lys
            1720                1725                1730 agc caa tta gcc  ttg aag gag aaa  caa cag aaa gca ctt agt  cgg        5582
Ser Gln Leu Ala  Leu Lys Glu Lys  Gln Gln Lys Ala Leu Ser  Arg
            1735                1740                1745 gca ctt tta gaa  ctc cgg gca gaa  atg aca gca gct gct gaa  gaa        5627
Ala Leu Leu Glu  Leu Arg Ala Glu  Met Thr Ala Ala Ala Glu  Glu
            1750                1755                1760 cgt att att tct  gca act tct caa  aaa gag gcc cat ctc aat  gtt        5672
Arg Ile Ile Ser  Ala Thr Ser Gln  Lys Glu Ala His Leu Asn  Val
            1765                1770                1775 caa caa atc gtt  gat cga cat act  aga gag cta aag aca caa  gtt        5717
Gln Gln Ile Val  Asp Arg His Thr  Arg Glu Leu Lys Thr Gln  Val
            1780                1785                1790 gaa gat tta aat  gaa aat ctt tta  aaa ttg aaa gaa gca ctt  aaa        5762
Glu Asp Leu Asn  Glu Asn Leu Leu  Lys Leu Lys Glu Ala Leu  Lys
            1795                1800                1805 aca agt aaa aac  aga gaa aac tca  cta act gat aat ttg aat  gac        5807
Thr Ser Lys Asn  Arg Glu Asn Ser  Leu Thr Asp Asn Leu Asn  Asp
            1810                1815                1820 tta aat aat gaa  ctg caa aag aaa  caa aaa gcc tat aat aaa  ata        5852
Leu Asn Asn Glu  Leu Gln Lys Lys  Gln Lys Ala Tyr Asn Lys  Ile
            1825                1830                1835 ctt aga gag aaa  gag gaa att gat  caa gag aat gat gaa ctg  aaa        5897
Leu Arg Glu Lys  Glu Glu Ile Asp  Gln Glu Asn Asp Glu Leu  Lys
            1840                1845                1850 agg caa att aaa  aga cta acc agt  gga tta cag ggc aaa ccc  ctg        5942
Arg Gln Ile Lys  Arg Leu Thr Ser  Gly Leu Gln Gly Lys Pro  Leu
            1855                1860                1865 aca gat aat aaa  caa agt cta att  gaa gaa ctc caa agg aaa  gtt        5987
Thr Asp Asn Lys  Gln Ser Leu Ile  Glu Glu Leu Gln Arg Lys  Val
            1870                1875                1880 aaa aaa cta gag  aac caa tta gag  gga aag gtg gag gaa gta  gac        6032
Lys Lys Leu Glu  Asn Gln Leu Glu  Gly Lys Val Glu Glu Val  Asp
            1885                1890                1895 cta aaa cct atg  aaa gaa aag aat  gct aaa gaa gaa tta att  agg        6077
Leu Lys Pro Met  Lys Glu Lys Asn  Ala Lys Glu Glu Leu Ile  Arg
            1900                1905                1910 tgg gaa gaa ggt  aaa aag tgg caa  gcc aaa ata gaa gga att  cga        6122
Trp Glu Glu Gly  Lys Lys Trp Gln  Ala Lys Ile Glu Gly Ile  Arg
            1915                1920                1925 aac aag tta aaa  gag aaa gag ggg  gaa gtc ttt act tta aca  aag        6167
Asn Lys Leu Lys  Glu Lys Glu Gly  Glu Val Phe Thr Leu Thr  Lys
            1930                1935                1940 cag ttg aat act  ttg aag gat ctt  ttt gcc aaa gcc gat aaa  gag        6212
```

```
Gln Leu Asn Thr Leu Lys Asp Leu Phe Ala Lys Ala Asp Lys Glu
            1945            1950            1955 aaa ctt act ttg cag agg aaa cta aaa aca act ggc atg act gtt    6257
Lys Leu Thr Leu Gln Arg Lys Leu Lys Thr Thr Gly Met Thr Val
        1960            1965            1970 gat cag gtt ttg gga ata cga gct ttg gag tca gaa aaa gaa ttg    6302
Asp Gln Val Leu Gly Ile Arg Ala Leu Glu Ser Glu Lys Glu Leu
        1975            1980            1985 gaa gaa tta aaa aag aga aat ctt gac tta gaa aat gat ata ttg    6347
Glu Glu Leu Lys Lys Arg Asn Leu Asp Leu Glu Asn Asp Ile Leu
        1990            1995            2000 tat atg agg gcc cac caa gct ctt cct cga gat tct gtt gta gaa    6392
Tyr Met Arg Ala His Gln Ala Leu Pro Arg Asp Ser Val Val Glu
        2005            2010            2015 gat tta cat tta caa aat aga tac ctc caa gaa aaa ctt cat gct    6437
Asp Leu His Leu Gln Asn Arg Tyr Leu Gln Glu Lys Leu His Ala
        2020            2025            2030 tta gaa aaa cag ttt tca aag gat aca tat tct aag cct tca att    6482
Leu Glu Lys Gln Phe Ser Lys Asp Thr Tyr Ser Lys Pro Ser Ile
        2035            2040            2045 tca gga ata gag tca gat gat cat tgt cag aga gaa cag gag ctt    6527
Ser Gly Ile Glu Ser Asp Asp His Cys Gln Arg Glu Gln Glu Leu
        2050            2055            2060 cag aag gaa aac ttg aag ttg tca tct gaa aat att gaa ctg aaa    6572
Gln Lys Glu Asn Leu Lys Leu Ser Ser Glu Asn Ile Glu Leu Lys
        2065            2070            2075 ttt cag ctt gaa caa gca aat aaa gat ttg cca aga tta aag aat    6617
Phe Gln Leu Glu Gln Ala Asn Lys Asp Leu Pro Arg Leu Lys Asn
        2080            2085            2090 caa gtc aga gat ttg aag gaa atg tgt gaa ttt ctt aag aaa gaa    6662
Gln Val Arg Asp Leu Lys Glu Met Cys Glu Phe Leu Lys Lys Glu
        2095            2100            2105 aaa gca gaa gtt cag cgg aaa ctt ggc cat gtt aga ggg tct ggt    6707
Lys Ala Glu Val Gln Arg Lys Leu Gly His Val Arg Gly Ser Gly
        2110            2115            2120 aga agt gga aag aca atc cca gaa ctg gaa aaa acc att ggt tta    6752
Arg Ser Gly Lys Thr Ile Pro Glu Leu Glu Lys Thr Ile Gly Leu
        2125            2130            2135 atg aaa aaa gta gtt gaa aaa gtc cag aga gaa aat gaa cag ttg    6797
Met Lys Lys Val Val Glu Lys Val Gln Arg Glu Asn Glu Gln Leu
        2140            2145            2150 aaa aaa gca tca gga ata ttg act agt gaa aaa atg gct aat att    6842
Lys Lys Ala Ser Gly Ile Leu Thr Ser Glu Lys Met Ala Asn Ile
        2155            2160            2165 gag cag gaa aat gaa aaa ttg aag gct gaa tta gaa aaa ctt aaa    6887
Glu Gln Glu Asn Glu Lys Leu Lys Ala Glu Leu Glu Lys Leu Lys
        2170            2175            2180 gct cat ctt ggg cat cag ttg agc atg cac tat gaa tcc aag acc    6932
Ala His Leu Gly His Gln Leu Ser Met His Tyr Glu Ser Lys Thr
        2185            2190            2195 aaa ggc aca gaa aaa att att gct gaa aat gaa agg ctt cgt aaa    6977
Lys Gly Thr Glu Lys Ile Ile Ala Glu Asn Glu Arg Leu Arg Lys
        2200            2205            2210 gaa ctt aaa aaa gaa act gat gct gca gag aaa tta cgg ata gca    7022
Glu Leu Lys Lys Glu Thr Asp Ala Ala Glu Lys Leu Arg Ile Ala
        2215            2220            2225 aag aat aat tta gag ata tta aat gag aag atg aca gtt caa cta    7067
Lys Asn Asn Leu Glu Ile Leu Asn Glu Lys Met Thr Val Gln Leu
        2230            2235            2240
```

| | | | | | | | | | | | | |
|---|---|---|---|---|---|---|---|---|---|---|---|---|
| gaa | gag | act | ggt | aag | aga | ttg | cag | ttt | gca | gaa | agc | aga | ggt | cca | 7112 |
| Glu | Glu | Thr | Gly | Lys | Arg | Leu | Gln | Phe | Ala | Glu | Ser | Arg | Gly | Pro | |
| | | | 2245 | | | | 2250 | | | | | 2255 | | | |
| cag | ctt | gaa | ggt | gct | gac | agt | aag | agc | tgg | aaa | tcc | att | gtg | gtt | 7157 |
| Gln | Leu | Glu | Gly | Ala | Asp | Ser | Lys | Ser | Trp | Lys | Ser | Ile | Val | Val | |
| | | | 2260 | | | | 2265 | | | | | 2270 | | | |
| aca | aga | atg | tat | gaa | acc | aag | tta | aaa | gaa | ttg | gaa | act | gat | att | 7202 |
| Thr | Arg | Met | Tyr | Glu | Thr | Lys | Leu | Lys | Glu | Leu | Glu | Thr | Asp | Ile | |
| | | | 2275 | | | | 2280 | | | | | 2285 | | | |
| gcc | aaa | aaa | aat | caa | agc | att | act | gac | ctt | aaa | cag | ctt | gta | aaa | 7247 |
| Ala | Lys | Lys | Asn | Gln | Ser | Ile | Thr | Asp | Leu | Lys | Gln | Leu | Val | Lys | |
| | | | 2290 | | | | 2295 | | | | | 2300 | | | |
| gaa | gca | aca | gag | aga | gaa | caa | aaa | gtt | aac | aaa | tac | aat | gaa | gac | 7292 |
| Glu | Ala | Thr | Glu | Arg | Glu | Gln | Lys | Val | Asn | Lys | Tyr | Asn | Glu | Asp | |
| | | | 2305 | | | | 2310 | | | | | 2315 | | | |
| ctt | gaa | caa | cag | att | aag | att | ctt | aaa | cat | gtt | cct | gaa | ggt | gct | 7337 |
| Leu | Glu | Gln | Gln | Ile | Lys | Ile | Leu | Lys | His | Val | Pro | Glu | Gly | Ala | |
| | | | 2320 | | | | 2325 | | | | | 2330 | | | |
| gag | aca | gag | caa | ggc | ctt | aaa | cgg | gag | ctt | caa | gtt | ctt | aga | tta | 7382 |
| Glu | Thr | Glu | Gln | Gly | Leu | Lys | Arg | Glu | Leu | Gln | Val | Leu | Arg | Leu | |
| | | | 2335 | | | | 2340 | | | | | 2345 | | | |
| gct | aat | cat | cag | ctg | gat | aaa | gag | aaa | gca | gaa | tta | atc | cat | cag | 7427 |
| Ala | Asn | His | Gln | Leu | Asp | Lys | Glu | Lys | Ala | Glu | Leu | Ile | His | Gln | |
| | | | 2350 | | | | 2355 | | | | | 2360 | | | |
| ata | gaa | gct | aac | aag | gac | caa | agt | gga | gct | gaa | agc | acc | ata | cct | 7472 |
| Ile | Glu | Ala | Asn | Lys | Asp | Gln | Ser | Gly | Ala | Glu | Ser | Thr | Ile | Pro | |
| | | | 2365 | | | | 2370 | | | | | 2375 | | | |
| gat | gct | gat | caa | cta | aag | gaa | aaa | ata | aaa | gat | cta | gag | aca | cag | 7517 |
| Asp | Ala | Asp | Gln | Leu | Lys | Glu | Lys | Ile | Lys | Asp | Leu | Glu | Thr | Gln | |
| | | | 2380 | | | | 2385 | | | | | 2390 | | | |
| ctc | aaa | atg | tca | gat | cta | gaa | aag | cag | cat | ttg | aag | gag | gaa | ata | 7562 |
| Leu | Lys | Met | Ser | Asp | Leu | Glu | Lys | Gln | His | Leu | Lys | Glu | Glu | Ile | |
| | | | 2395 | | | | 2400 | | | | | 2405 | | | |
| aag | aag | ctg | aaa | aaa | gaa | ctg | gaa | aat | ttt | gat | cct | tca | ttt | ttt | 7607 |
| Lys | Lys | Leu | Lys | Lys | Glu | Leu | Glu | Asn | Phe | Asp | Pro | Ser | Phe | Phe | |
| | | | 2410 | | | | 2415 | | | | | 2420 | | | |
| gaa | gaa | att | gaa | gat | ctt | aag | tat | aat | tac | aag | gaa | gaa | gtg | aag | 7652 |
| Glu | Glu | Ile | Glu | Asp | Leu | Lys | Tyr | Asn | Tyr | Lys | Glu | Glu | Val | Lys | |
| | | | 2425 | | | | 2430 | | | | | 2435 | | | |
| aag | aat | att | ctc | tta | gaa | gag | aag | gta | aaa | aaa | ctt | tca | gaa | caa | 7697 |
| Lys | Asn | Ile | Leu | Leu | Glu | Glu | Lys | Val | Lys | Lys | Leu | Ser | Glu | Gln | |
| | | | 2440 | | | | 2445 | | | | | 2450 | | | |
| ttg | gga | gtt | gaa | tta | act | agc | cct | gtt | gct | gct | tct | gaa | gag | ttt | 7742 |
| Leu | Gly | Val | Glu | Leu | Thr | Ser | Pro | Val | Ala | Ala | Ser | Glu | Glu | Phe | |
| | | | 2455 | | | | 2460 | | | | | 2465 | | | |
| gaa | gat | gaa | gaa | gaa | agt | cct | gtt | aat | ttc | ccc | att | tac | taaaggtcac | 7791 |
| Glu | Asp | Glu | Glu | Glu | Ser | Pro | Val | Asn | Phe | Pro | Ile | Tyr | | |
| | | | 2470 | | | | 2475 | | | | | | | | | ctataaactt tgtttcattt aactatttat taactttata agttaaatat acttggaaat 7851 aagcagttct ccgaactgta gtatttcctt ctcactacct tgtacctta tacttagatt 7911 ggaattctta ataaataaaa ttatatgaaa ttttcaactt attaaaaaaa aaaaaaaaa 7971 a 7972

<210> SEQ ID NO 3
<211> LENGTH: 2479
<212> TYPE: PRT
<213> ORGANISM: Homo sapiens

<400> SEQUENCE: 3

-continued

```
Met Pro Pro Asn Ile Asn Trp Lys Glu Ile Met Lys Val Asp Pro Asp
 1               5                  10                  15

Asp Leu Pro Arg Gln Glu Glu Leu Ala Asp Asn Leu Leu Ile Ser Leu
                20                  25                  30

Ser Lys Val Glu Val Asn Glu Leu Lys Ser Lys Gln Glu Asn Val
        35                  40                  45

Ile His Leu Phe Arg Ile Thr Gln Ser Leu Met Lys Met Lys Ala Gln
 50                  55                  60

Glu Val Glu Leu Ala Leu Glu Val Glu Lys Ala Gly Glu Glu Gln
 65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
                100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
        130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
                165                 170                 175

Cys Gln Asp Ile Ile Asp Tyr Gln Lys Gln Ile Asp Ser Gln Lys Glu
                180                 185                 190

Thr Leu Leu Ser Arg Arg Gly Glu Asp Ser Asp Tyr Arg Ser Gln Leu
                195                 200                 205

Ser Lys Lys Asn Tyr Glu Leu Ile Gln Tyr Leu Asp Glu Ile Gln Thr
210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
                260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Pro Ile Met Val
        290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
                340                 345                 350

Leu Gln Gln Gly Ile Gln Glu Arg Asp Ser Gln Ile Lys Met Leu Thr
                355                 360                 365

Glu Gln Val Glu Gln Tyr Thr Lys Glu Met Glu Lys Asn Thr Cys Ile
        370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415
```

```
Lys Glu Lys Thr Lys Glu Ala Glu Arg Thr Ala Glu Leu Ala Glu Ala
            420                 425                 430
Asp Ala Arg Glu Lys Asp Lys Glu Leu Val Glu Ala Leu Lys Arg Leu
            435                 440                 445
Lys Asp Tyr Glu Ser Gly Val Tyr Gly Leu Glu Asp Ala Val Val Glu
            450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
            485                 490                 495
Leu Asp Glu Asn Glu Ala Leu Arg Glu Arg Val Gly Leu Glu Pro Lys
            500                 505                 510
Thr Met Ile Asp Leu Thr Glu Phe Arg Asn Ser Lys His Leu Lys Gln
            515                 520                 525
Gln Gln Tyr Arg Ala Glu Asn Gln Ile Leu Leu Lys Glu Ile Glu Ser
            530                 535                 540
Leu Glu Glu Glu Arg Leu Asp Leu Lys Lys Lys Ile Arg Gln Met Ala
545                 550                 555                 560
Gln Glu Arg Gly Lys Arg Ser Ala Thr Ser Gly Leu Thr Thr Glu Asp
            565                 570                 575
Leu Asn Leu Thr Glu Asn Ile Ser Gln Gly Asp Arg Ile Ser Glu Arg
            580                 585                 590
Lys Leu Asp Leu Leu Ser Leu Lys Asn Met Ser Glu Ala Gln Ser Lys
            595                 600                 605
Asn Glu Phe Leu Ser Arg Glu Leu Ile Glu Lys Glu Arg Asp Leu Glu
            610                 615                 620
Arg Ser Arg Thr Val Ile Ala Lys Phe Gln Asn Lys Leu Lys Glu Leu
625                 630                 635                 640
Val Glu Glu Asn Lys Gln Leu Glu Glu Gly Met Lys Glu Ile Leu Gln
            645                 650                 655
Ala Ile Lys Glu Met Gln Lys Asp Pro Asp Val Lys Gly Gly Glu Thr
            660                 665                 670
Ser Leu Ile Ile Pro Ser Leu Glu Arg Leu Val Asn Ala Ile Glu Ser
            675                 680                 685
Lys Asn Ala Glu Gly Ile Phe Asp Ala Ser Leu His Leu Lys Ala Gln
            690                 695                 700
Val Asp Gln Leu Thr Gly Arg Asn Glu Glu Leu Arg Gln Glu Leu Arg
705                 710                 715                 720
Glu Ser Arg Lys Glu Ala Ile Asn Tyr Ser Gln Gln Leu Ala Lys Ala
            725                 730                 735
Asn Leu Lys Ile Asp His Leu Glu Lys Glu Thr Ser Leu Leu Arg Gln
            740                 745                 750
Ser Glu Gly Ser Asn Val Val Phe Lys Gly Ile Asp Leu Pro Asp Gly
            755                 760                 765
Ile Ala Pro Ser Ser Ala Ser Ile Ile Asn Ser Gln Asn Glu Tyr Leu
            770                 775                 780
Ile His Leu Leu Gln Glu Leu Glu Asn Lys Glu Lys Lys Leu Lys Asn
785                 790                 795                 800
Leu Glu Asp Ser Leu Glu Asp Tyr Asn Arg Lys Phe Ala Val Ile Arg
            805                 810                 815
His Gln Gln Ser Leu Leu Tyr Lys Glu Tyr Leu Ser Glu Lys Glu Thr
            820                 825                 830
Trp Lys Thr Glu Ser Lys Thr Ile Lys Glu Glu Lys Arg Lys Leu Glu
```

-continued

```
            835                 840                 845
Asp Gln Val Gln Gln Asp Ala Ile Lys Val Lys Glu Tyr Asn Asn Leu
    850                 855                 860
Leu Asn Ala Leu Gln Met Asp Ser Asp Glu Met Lys Lys Ile Leu Ala
865                 870                 875                 880
Glu Asn Ser Arg Lys Ile Thr Val Leu Gln Val Asn Glu Lys Ser Leu
                885                 890                 895
Ile Arg Gln Tyr Thr Thr Leu Val Glu Leu Glu Arg Gln Leu Arg Lys
                900                 905                 910
Glu Asn Glu Lys Gln Lys Asn Glu Leu Leu Ser Met Glu Ala Glu Val
                915                 920                 925
Cys Glu Lys Ile Gly Cys Leu Gln Arg Phe Lys Glu Met Ala Ile Phe
                930                 935                 940
Lys Ile Ala Ala Leu Gln Lys Val Val Asp Asn Ser Val Ser Leu Ser
945                 950                 955                 960
Glu Leu Glu Leu Ala Asn Lys Gln Tyr Asn Glu Leu Thr Ala Lys Tyr
                965                 970                 975
Arg Asp Ile Leu Gln Lys Asp Asn Met Leu Val Gln Arg Thr Ser Asn
                980                 985                 990
Leu Glu His Leu Glu Cys Glu Asn Ile Ser Leu Lys Glu Gln Val Glu
                995                 1000                1005
Ser Ile Asn Lys Glu Leu Glu Ile Thr Lys Glu Lys Leu His Thr
    1010                1015                1020
Ile Glu Gln Ala Trp Glu Gln Glu Thr Lys Leu Gly Asn Glu Ser
    1025                1030                1035
Ser Met Asp Lys Ala Lys Lys Ser Ile Thr Asn Ser Asp Ile Val
    1040                1045                1050
Ser Ile Ser Lys Lys Ile Thr Met Leu Glu Met Lys Glu Leu Asn
    1055                1060                1065
Glu Arg Gln Arg Ala Glu His Cys Gln Lys Met Tyr Glu His Leu
    1070                1075                1080
Arg Thr Ser Leu Lys Gln Met Glu Glu Arg Asn Phe Glu Leu Glu
    1085                1090                1095
Thr Lys Phe Ala Glu Leu Thr Lys Ile Asn Leu Asp Ala Gln Lys
    1100                1105                1110
Val Glu Gln Met Leu Arg Asp Glu Leu Ala Asp Ser Val Ser Lys
    1115                1120                1125
Ala Val Ser Asp Ala Asp Arg Gln Arg Ile Leu Glu Leu Glu Lys
    1130                1135                1140
Asn Glu Met Glu Leu Lys Val Glu Val Ser Lys Leu Arg Glu Ile
    1145                1150                1155
Ser Asp Ile Ala Arg Arg Gln Val Glu Ile Leu Asn Ala Gln Gln
    1160                1165                1170
Gln Ser Arg Asp Lys Glu Val Glu Ser Leu Arg Met Gln Leu Leu
    1175                1180                1185
Asp Tyr Gln Ala Gln Ser Asp Glu Lys Ser Leu Ile Ala Lys Leu
    1190                1195                1200
His Gln His Asn Val Ser Leu Gln Leu Ser Glu Ala Thr Ala Leu
    1205                1210                1215
Gly Lys Leu Glu Ser Ile Thr Ser Lys Leu Gln Lys Met Glu Ala
    1220                1225                1230
Tyr Asn Leu Arg Leu Glu Gln Lys Leu Asp Glu Lys Glu Gln Ala
    1235                1240                1245
```

```
Leu Tyr Tyr Ala Arg Leu Glu Gly Arg Asn Arg Ala Lys His Leu
    1250                1255                1260

Arg Gln Thr Ile Gln Ser Leu Arg Arg Gln Phe Ser Gly Ala Leu
    1265                1270                1275

Pro Leu Ala Gln Gln Glu Lys Phe Ser Lys Thr Met Ile Gln Leu
    1280                1285                1290

Gln Asn Asp Lys Leu Lys Ile Met Gln Glu Met Lys Asn Ser Gln
    1295                1300                1305

Gln Glu His Arg Asn Met Glu Asn Lys Thr Leu Glu Met Glu Leu
    1310                1315                1320

Lys Leu Lys Gly Leu Glu Glu Leu Ile Ser Thr Leu Lys Asp Thr
    1325                1330                1335

Lys Gly Ala Gln Lys Val Ile Asn Trp His Met Lys Ile Glu Glu
    1340                1345                1350

Leu Arg Leu Gln Glu Leu Lys Leu Asn Arg Glu Leu Val Lys Asp
    1355                1360                1365

Lys Glu Glu Ile Lys Tyr Leu Asn Asn Ile Ile Ser Glu Tyr Glu
    1370                1375                1380

Arg Thr Ile Ser Ser Leu Glu Glu Ile Val Gln Gln Asn Lys
    1385                1390                1395

Phe His Glu Glu Arg Gln Met Ala Trp Asp Gln Arg Glu Val Asp
    1400                1405                1410

Leu Glu Arg Gln Leu Asp Ile Phe Asp Arg Gln Gln Asn Glu Ile
    1415                1420                1425

Leu Asn Ala Ala Gln Lys Phe Glu Glu Ala Thr Gly Ser Ile Pro
    1430                1435                1440

Asp Pro Ser Leu Pro Leu Pro Asn Gln Leu Glu Ile Ala Leu Arg
    1445                1450                1455

Lys Ile Lys Glu Asn Ile Arg Ile Ile Leu Glu Thr Arg Ala Thr
    1460                1465                1470

Cys Lys Ser Leu Glu Glu Lys Leu Lys Glu Lys Glu Ser Ala Leu
    1475                1480                1485

Arg Leu Ala Glu Gln Asn Ile Leu Ser Arg Asp Lys Val Ile Asn
    1490                1495                1500

Glu Leu Arg Leu Arg Leu Pro Ala Thr Ala Glu Arg Glu Lys Leu
    1505                1510                1515

Ile Ala Glu Leu Gly Arg Lys Glu Met Glu Pro Lys Ser His His
    1520                1525                1530

Thr Leu Lys Ile Ala His Gln Thr Ile Ala Asn Met Gln Ala Arg
    1535                1540                1545

Leu Asn Gln Lys Glu Glu Val Leu Lys Lys Tyr Gln Arg Leu Leu
    1550                1555                1560

Glu Lys Ala Arg Glu Glu Gln Arg Glu Ile Val Lys Lys His Glu
    1565                1570                1575

Glu Asp Leu His Ile Leu His His Arg Leu Glu Leu Gln Ala Asp
    1580                1585                1590

Ser Ser Leu Asn Lys Phe Lys Gln Thr Ala Trp Asp Leu Met Lys
    1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635
```

```
Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680

Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
    1745                1750                1755

Ala Glu Glu Arg Ile Ile Ser Ala Thr Ser Gln Lys Glu Ala His
    1760                1765                1770

Leu Asn Val Gln Gln Ile Val Asp Arg His Thr Arg Glu Leu Lys
    1775                1780                1785

Thr Gln Val Glu Asp Leu Asn Glu Asn Leu Leu Lys Leu Lys Glu
    1790                1795                1800

Ala Leu Lys Thr Ser Lys Asn Arg Glu Asn Ser Leu Thr Asp Asn
    1805                1810                1815

Leu Asn Asp Leu Asn Asn Glu Leu Gln Lys Lys Gln Lys Ala Tyr
    1820                1825                1830

Asn Lys Ile Leu Arg Glu Lys Glu Glu Ile Asp Gln Glu Asn Asp
    1835                1840                1845

Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950

Asp Lys Glu Lys Leu Thr Leu Gln Arg Lys Leu Lys Thr Thr Gly
    1955                1960                1965

Met Thr Val Asp Gln Val Leu Gly Ile Arg Ala Leu Glu Ser Glu
    1970                1975                1980

Lys Glu Leu Glu Glu Leu Lys Lys Arg Asn Leu Asp Leu Glu Asn
    1985                1990                1995

Asp Ile Leu Tyr Met Arg Ala His Gln Ala Leu Pro Arg Asp Ser
    2000                2005                2010

Val Val Glu Asp Leu His Leu Gln Asn Arg Tyr Leu Gln Glu Lys
    2015                2020                2025

Leu His Ala Leu Glu Lys Gln Phe Ser Lys Asp Thr Tyr Ser Lys
```

```
              2030                2035                2040

Pro Ser  Ile Ser Gly Ile Glu  Ser Asp Asp His Cys  Gln Arg Glu
    2045                2050                2055

Gln Glu  Leu Gln Lys Glu Asn  Leu Lys Leu Ser Ser  Glu Asn Ile
    2060                2065                2070

Glu Leu  Lys Phe Gln Leu Glu  Gln Ala Asn Lys Asp  Leu Pro Arg
    2075                2080                2085

Leu Lys  Asn Gln Val Arg Asp  Leu Lys Glu Met Cys  Glu Phe Leu
    2090                2095                2100

Lys Lys  Glu Lys Ala Glu Val  Gln Arg Lys Leu Gly  His Val Arg
    2105                2110                2115

Gly Ser  Gly Arg Ser Gly Lys  Thr Ile Pro Glu Leu  Glu Lys Thr
    2120                2125                2130

Ile Gly  Leu Met Lys Lys Val  Val Glu Lys Val Gln  Arg Glu Asn
    2135                2140                2145

Glu Gln  Leu Lys Lys Ala Ser  Gly Ile Leu Thr Ser  Glu Lys Met
    2150                2155                2160

Ala Asn  Ile Glu Gln Glu Asn  Glu Lys Leu Lys Ala  Glu Leu Glu
    2165                2170                2175

Lys Leu  Lys Ala His Leu Gly  His Gln Leu Ser Met  His Tyr Glu
    2180                2185                2190

Ser Lys  Thr Lys Gly Thr Glu  Lys Ile Ile Ala Glu  Asn Glu Arg
    2195                2200                2205

Leu Arg  Lys Glu Leu Lys Lys  Glu Thr Asp Ala Ala  Glu Lys Leu
    2210                2215                2220

Arg Ile  Ala Lys Asn Asn Leu  Glu Ile Leu Asn Glu  Lys Met Thr
    2225                2230                2235

Val Gln  Leu Glu Glu Thr Gly  Lys Arg Leu Gln Phe  Ala Glu Ser
    2240                2245                2250

Arg Gly  Pro Gln Leu Glu Gly  Ala Asp Ser Lys Ser  Trp Lys Ser
    2255                2260                2265

Ile Val  Val Thr Arg Met Tyr  Glu Thr Lys Leu Lys  Glu Leu Glu
    2270                2275                2280

Thr Asp  Ile Ala Lys Lys Asn  Gln Ser Ile Thr Asp  Leu Lys Gln
    2285                2290                2295

Leu Val  Lys Glu Ala Thr Glu  Arg Glu Gln Lys Val  Asn Lys Tyr
    2300                2305                2310

Asn Glu  Asp Leu Glu Gln Gln  Ile Lys Ile Leu Lys  His Val Pro
    2315                2320                2325

Glu Gly  Ala Glu Thr Glu Gln  Gly Leu Lys Arg Glu  Leu Gln Val
    2330                2335                2340

Leu Arg  Leu Ala Asn His Gln  Leu Asp Lys Glu Lys  Ala Glu Leu
    2345                2350                2355

Ile His  Gln Ile Glu Ala Asn  Lys Asp Gln Ser Gly  Ala Glu Ser
    2360                2365                2370

Thr Ile  Pro Asp Ala Asp Gln  Leu Lys Glu Lys Ile  Lys Asp Leu
    2375                2380                2385

Glu Thr  Gln Leu Lys Met Ser  Asp Leu Glu Lys Gln  His Leu Lys
    2390                2395                2400

Glu Glu  Ile Lys Lys Leu Lys  Lys Glu Leu Glu Asn  Phe Asp Pro
    2405                2410                2415

Ser Phe  Phe Glu Glu Ile Glu  Asp Leu Lys Tyr Asn  Tyr Lys Glu
    2420                2425                2430
```

```
Glu Val Lys Lys Asn Ile Leu Leu Glu Glu Lys Val Lys Lys Leu
        2435                2440                2445

Ser Glu Gln Leu Gly Val Glu Leu Thr Ser Pro Val Ala Ala Ser
    2450                2455                2460

Glu Glu Phe Glu Asp Glu Glu Ser Pro Val Asn Phe Pro Ile
    2465                2470                2475

Tyr

<210> SEQ ID NO 4
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: 128 nucleotide aberrant CEO290 exon

<400> SEQUENCE: 4
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaatt                                                              128

<210> SEQ ID NO 5
<211> LENGTH: 997
<212> TYPE: PRT
<213> ORGANISM: Homo sapiens
<220> FEATURE:
<221> NAME/KEY: misc_feature
<222> LOCATION: (1)..(997)
<223> OTHER INFORMATION: Aberrant CEP290 polypeptide

<400> SEQUENCE: 5

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
            85                  90                  95

Glu Leu Glu Met Ala Gln Gln Ser Ala Gly Gly Arg Asp Thr Arg Phe
        100                 105                 110

Leu Arg Asn Glu Ile Cys Gln Leu Glu Lys Gln Leu Glu Gln Lys Asp
    115                 120                 125

Arg Glu Leu Glu Asp Met Glu Lys Glu Leu Glu Lys Glu Lys Lys Val
            130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
```

```
              195                 200                 205
Ser Lys Lys Asn Tyr Glu Leu Ile Gln Tyr Leu Asp Glu Ile Gln Thr
210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
                260                 265                 270

Gln Leu Lys Lys Glu Asn Asp His Tyr Gln Leu Gln Val Gln Glu Leu
            275                 280                 285

Thr Asp Leu Leu Lys Ser Lys Asn Glu Glu Asp Asp Pro Ile Met Val
            290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
                340                 345                 350

Leu Gln Gln Gly Ile Gln Glu Arg Asp Ser Gln Ile Lys Met Leu Thr
            355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
                420                 425                 430

Asp Ala Arg Glu Lys Asp Lys Glu Leu Val Glu Ala Leu Lys Arg Leu
            435                 440                 445

Lys Asp Tyr Glu Ser Gly Val Tyr Gly Leu Glu Asp Ala Val Val Glu
            450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
                500                 505                 510

Thr Met Ile Asp Leu Thr Glu Phe Arg Asn Ser Lys His Leu Lys Gln
            515                 520                 525

Gln Gln Tyr Arg Ala Glu Asn Gln Ile Leu Leu Lys Glu Ile Glu Ser
            530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
            595                 600                 605

Asn Glu Phe Leu Ser Arg Glu Leu Ile Glu Lys Glu Arg Asp Leu Glu
            610                 615                 620
```

```
Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
            645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
            675                 680                 685

Lys Asn Ala Glu Gly Ile Phe Asp Ala Ser Leu His Leu Lys Ala Gln
690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
            725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
            755                 760                 765

Ile Ala Pro Ser Ser Ala Ser Ile Ile Asn Ser Gln Asn Glu Tyr Leu
770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
            805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
            835                 840                 845

Asp Gln Val Gln Gln Asp Ala Ile Lys Val Lys Glu Tyr Asn Asn Leu
850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
            885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
            965                 970                 975

Arg Asp Ile Leu Gln Lys Asp Asn Met Leu Val Gln Arg Thr Ser Asn
            980                 985                 990

Leu Glu His Leu Glu
            995

<210> SEQ ID NO 6
<211> LENGTH: 143
<212> TYPE: DNA
<213> ORGANISM: Homo sapiens
<220> FEATURE:
```

```
<221> NAME/KEY: misc_feature
<222> LOCATION: (1)..(143)
<223> OTHER INFORMATION: 143 nucleotide motif

<400> SEQUENCE: 6
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaattgt gaatatctca tac                                             143

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: 42 nucleotide motif

<400> SEQUENCE: 7
acagatgtga gccaccgcac ctggccccag ttgtaattgt ga                         42

<210> SEQ ID NO 8
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 24 nucleotide motif

<400> SEQUENCE: 8
ccaccgcacc tggccccagt tgta                                             24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-1

<400> SEQUENCE: 9
taatcccagc actttaggag                                                  20

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-2

<400> SEQUENCE: 10
gggccaggtg cggtgg                                                      16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<223> OTHER INFORMATION: AON-3

<400> SEQUENCE: 11
aactggggcc aggtgcg                                                    17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-4

<400> SEQUENCE: 12
tacaactggg gccaggtg                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-5

<400> SEQUENCE: 13
actcacaatt acaactgggg                                                 20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SON-3

<400> SEQUENCE: 14
cgcacctggc cccagtt                                                    17

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15
tgctaagtac agggacatct tgc                                             23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
agactccact tgttcttta aggag                                            25

<210> SEQ ID NO 17
```

```
<211> LENGTH: 36
<212> TYPE: DNA
<213> ORGANISM: Homo sapiens

<400> SEQUENCE: 17
cacctggccc cagttgtaat tgtgaatatc tcatac                              36

<210> SEQ ID NO 18
<211> LENGTH: 36
<212> TYPE: RNA
<213> ORGANISM: Homo sapiens

<400> SEQUENCE: 18
caccuggccc caguuguaau ugugaauauc ucauac                              36

<210> SEQ ID NO 19
<211> LENGTH: 36
<212> TYPE: DNA
<213> ORGANISM: Homo sapiens

<400> SEQUENCE: 19
cacctggccc cagttgtaat tgtgagtatc tcatac                              36

<210> SEQ ID NO 20
<211> LENGTH: 36
<212> TYPE: RNA
<213> ORGANISM: Homo sapiens

<400> SEQUENCE: 20
caccuggccc caguuguaau ugugaguauc ucauac                              36

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auacuacuaa uuacaacugg g                                              21
```

ANTISENSE OLIGONUCLEOTIDES FOR THE TREATMENT OF LEBER CONGENITAL AMAUROSIS

CROSS-REFERENCE TO RELATED APPLICATIONS

The present application is a Continuation Application of U.S. application Ser. No. 16/197,865, filed Nov. 21, 2018, which is a Continuation Application of U.S. application Ser. No. 15/963,229, filed Apr. 26, 2018, which is a Continuation Application of U.S. application Ser. No. 15/656,635, filed Jul. 21, 2017, which is a Continuation Application of U.S. Application No. 14/342,776, filed Jun. 16, 2014, which is the U.S. National Phase of International Patent Application No. PCT/NL2012/050275, filed Apr. 25, 2012 and published as WO 2013/036105 A1, which claims priority to Netherlands Patent Application No. 2007351, filed Sep. 5, 2011, and U.S. Provisional Application No. 61/531,137, IO filed Sep. 6, 2011. The contents of these applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Jul. 17, 2017, is named 069818-9676SequenceListing.txt and is 229 KB.

FIELD OF THE INVENTION

The present invention relates to the fields of medicine and immunology. In particular, it relates to novel antisense oligonucleotides that may be used in the treatment, prevention and/or delay of Leber congenital amaurosis.

BACKGROUND OF THE INVENTION

Leber congenital amaurosis (LCA) is the most severe form of inherited retinal dystrophy, with an onset of disease symptoms in the first years of life (Leber, T., 1869) and an estimated prevalence of approximately 1 in 50,000 worldwide (Koenekoop et al, 2007; Stone, 2007). Genetically, LCA is a heterogeneous disease, with fifteen genes identified to date in which mutations are causative for LCA (den Hollander et al, 2008; Estrada-Cuzcano et al, 2011). The most frequently mutated LCA gene is CEP290, accounting for ~15% of all cases (Stone, 2007; den Hollander, 2008; den Hollander, 2006; Perrault et al, 2007). Severe mutations in CEP290 have been reported to cause a spectrum of systemic diseases that, besides retinal dystrophy, are characterized by brain defects, kidney malformations, polydactyly and/or obesity (Baal et al, 2007; den Hollander et al, 2008; Helou et al, 2007; Valente et al, 2006). There is no clear-cut genotype-phenotype correlation between the combination of CEP290 mutations and the associated phenotypes, but patients with LCA and early-onset retinal dystrophy very often carry hypomorphic alleles (Stone, 2007; den Hollander et al, 2006; Perrault et al, 2007; Coppieters et al, 2010; Liitink et al 2010). The by far most frequently occurring hypomorphic CEP290 mutation, especially in European countries and in the US, is a change in intron 26 of CEP290 (c.2991+1655A>G) (Stone, 2007; den Hollander et al, 2006; Perrault et al, 2007; Liitink et al, 2010). This mutation creates a cryptic splice donor site in intron 26 which results in the inclusion of an aberrant exon of 128 bp in the mutant CEP290 mRNA, and inserts a premature stop codon (p.C998X) (see FIG. 1). Besides the mutant CEP290 mRNA, also the wild-type transcript that lacks the aberrant exon is still produced, explaining the hypomorphic nature of this mutation (Estrada-Cuzcano et al, 2011).

LCA, and other retinal dystrophies, for long have been considered incurable diseases. However, the first phase I/II clinical trials using gene augmentation therapy have lead to promising results in a selected group of adult LCA/RP patients with mutations in the RPE65 gene (Bainbridge et al, 2008; Cideciyan et al, 2008; Hauswirth et al, 2008; Maguire et al, 2008). Unilateral subretinal injections of adeno-associated viruses particles carrying constructs encoding the wild-type RPE65 cDNA were shown to be safe and moderately effective in some patients, without causing any adverse effects. In a follow-up study using adults and children, visual improvements were more sustained, especially in the children who all gained ambulatory vision (Maguire et al, 2009). Together, these studies have shown the potential to treat LCA, and thereby enormously boosted the development of therapeutic strategies for other genetic subtypes of retinal dystrophies (den Hollander et al, 2010). However, due to the tremendous variety in gene size, and technical limitations of the vehicles that are used to deliver therapeutic constructs, gene augmentation therapy may not be applicable to all genes. The RPE65 cDNA is for instance only 1.6 kb, whereas the CEP290 cDNA amounts to about 7.4 kb, thereby exceeding the cargo size of many available vectors, including the presently used adeno-associated vectors (AAV). In addition, using gene replacement therapy, it is hard to control the expression levels of the therapeutic gene which for some genes need to be tightly regulated. It is therefore an objective of the present invention to provide a convenient therapeutic strategy for the prevention, treatment or delay of Leber congenital amaurosis as caused by an intronic mutation in CEP290.

DETAILED DESCRIPTION OF THE INVENTION

Surprisingly, it has now been demonstrated that specific antisense oligonucleotides (AONs) are able to block the aberrant splicing of CEP290 that is caused by the intronic LCA mutation.

Accordingly, in a first aspect the present invention provides an exon skipping molecule that binds to and/or is complementary to a polynucleotide with the nucleotide sequence as shown in SEQ ID NO: 6, preferably SEQ ID NO: 7, more preferably SEQ ID NO: 8, or a part thereof.

In all embodiments of the present invention, the terms "modulating splicing" and "exon skipping" are synonymous. In respect of CEP290, "modulating splicing" or "exon skipping" are to be construed as the exclusion of the aberrant 128 nucleotide exon (SEQ ID NO: 4) from the CEP290 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules The term pre-mRNA refers to a non-processed or partly processed precursor mRNA that is synthesized from a DNA template in the nucleus of a cell by transcription.

The term "antisense oligonucleotide" is understood to refer to a nucleotide sequence which is substantially complementary to a target nucleotide sequence in a pre-mRNA molecule, hrRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 6, 7 or 8 sequence, preferably in the context of the aberrant 128 nucleotide CEP290 exon (SEQ ID NO: 4) may be assessed via techniques known to the skilled person. A preferred technique is gel mobility shift assay as described in EP 1 619 249. In a preferred embodiment, an exon skipping molecule is said to bind to one of the specified sequences as soon as a binding of said molecule to a labeled sequence SEQ ID NO: 6, 7 or 8 is detectable in a gel mobility shift assay.

In all embodiments of the invention, an exon skipping molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 6, preferably SEQ ID NO: 7, more preferably SEQ ID NO. 8, or a part thereof as later defined herein.

The term "substantially complementary" used in the context of the present invention indicates that some mismatches in the antisense sequence are allowed as long as the functionality, i.e. inducing skipping of the aberrant 128 nucleotide CEP290 exon (SEQ ID NO: 4), is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The present invention provides a method for designing an exon skipping molecule, preferably an oligonucleotide able to induce skipping of the aberrant 128 nucleotide CEP290 exon (SEQ ID NO: 4). First, said oligonucleotide is selected to bind to one of SEQ ID NO: 6, 7 or 8 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity may be assessed by detecting the presence or an increasing amount of a neutralizing antibody or an antibody recognizing said oligonucleotide using a standard immunoassay.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 6, 7, or 8 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein preferably no CpG and/or wherein a more acceptable Tm and/or free energy are obtained by choosing a distinct sequence of CEP290 (including SEQ ID NO. 6, 7 or 8) to which the oligonucleotide is complementary. Alternatively, if an oligonucleotide complementary to a given stretch within SEQ ID NO: 6, 7 or 8, comprises a CpG, and/or does not have an acceptable Tm and/or free energy, the skilled person may improve any of these parameters by decreasing the length of the oligonucleotide, and/or by choosing a distinct stretch within any of SEQ ID NO: 6, 7 or 8 to which the oligonucleotide is complementary and/or by altering the chemistry of the oligonucleotide.

At any step of the method, an oligonucleotide of the invention is preferably an olignucleotide, which is still able to exhibit an acceptable level of functional activity. A functional activity of said oligonucleotide is preferably to induce the skipping of the aberrant 128 nucleotide CEP290 exon (SEQ ID NO. 4) to a certain extent, to provide an individual with a functional CEP290 protein and/or mRNA and/or at least in part decreasing the production of an aberrant CEP290 protein and/or mRNA. In a preferred embodiment, an oligonucleotide is said to induce skipping of the aberrant 128 nucleotide CEP290 exon (SEQ ID NO: 4), when the aberrant 128 nucleotide CEP290 exon (SEQ ID NO: 4) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferably, a nucleic acid molecule according to the invention, preferably an oligonucleotide, which comprises a sequence that is complementary or substantially complementary to a nucleotide sequence as shown in SEQ ID NO: 6, preferably SEQ ID NO: 7, more preferably SEQ ID NO: 8, or part thereof of CEP290 is such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an oligonucleotide according to the invention comprises or consists of a sequence that is complementary to part of SEQ ID NO: 6, 7 or 8. As an example, an oligonucleotide may comprise a sequence that is complementary to part of SEQ ID NO: 6, 7 or 8 and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides Additional flanking sequences may be used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an oligonucleotide is detectable. Optionally, said oligonucleotide may further be tested by transfection into retina cells of patients. Skipping of a targeted exon may be assessed by RT-PCR (as described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule.

An exon skipping molecule of the invention is preferably a nucleic acid molecule or nucleotide-based molecule, preferably an (antisense) oligonucleotide, which is complementary to a sequence selected from SEQ ID NO: 6, 7 and 8.

A preferred exon skipping molecule, according to the invention is a nucleic acid molecule comprising an antisense oligonucleotide which antisense oligonucleotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule of the invention is an antisense oligonucleotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule comprising or preferably consisting of an antisense oligonucleotide selected from the group consisting of: SEQ ID NO: 10, SEQ ID NO: 11, and SEQ ID NO: 12.

In a more preferred embodiment, the invention provides an exon skipping molecule comprising or preferably consisting of the antisense oligonucleotide SEQ ID NO: 10. It was found that this molecule is very efficient in modulating splicing of the aberrant 128 nucleotide CEP290 exon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 128 nucleotide CEP290 exon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO. 12. It was found that this molecule is very efficient in modulating splicing of the aberrant 128 nucleotide CEP290 exon. This preferred exon skipping molecule of the invention comprising SEQ ID NO: 12 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule according to the invention may contain one of more RNA residues, or one or more DNA residues, and/or one or more nucleotide analogues or equivalents, as will be further detailed herein below.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 128 nucleotide exon of CEP290. In a preferred embodiment, a combination of at least two antisense oligonucleotides are used in a method of the invention, such as two different antisense oligonucleotides, three different antisense oligonucleotides, four different anti sense oligonucleotides, or five different antisense oligonucleotides.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule according to the invention may be indirectly administrated using suitable means known in the art. When the exon skipping molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like.

Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al, 1998 or Suter D et al, 1999).

The exon skipping molecule according to the invention, preferably an antisense oligonucleotide, may be delivered as such. However, the exon skipping molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of aberrant 128 nucleotide CEP290 exon.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constitutent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CEP290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.1 and 20 mg/kg, preferably from 0.5 and 20 mg/kg.

A preferred exon skipping molecule according to the invention, is for the treatment of a CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congenital amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides the use of an exon skipping molecule according to the invention, or of a viral vector according to the invention, or a composition according to the invention for the preparation of a medicament, for the preparation of a medicament for treating a CEP290 related disease or condition requiring modulating splicing of CEP290 and for the preparation of a medicament for the prevention, treatment or delay of a CEP290 related disease or condition. A preferred CEP290 related disease or condition is Leber congenital amaurosis. Therefore in a further aspect, there is provided the use of an exon skipping molecule, viral vector or composition as defined herein for the preparation of a medicament, for the preparation of a medicament for treating a condition requiring modulating splicing of CEP290 and for the preparation of a medicament for the prevention, treatment or delay of a CEP290 related disease or condition. A preferred CEP290 related disease or condition is Leber congenital amaurosis. Each feature of said use has earlier been defined herein.

A treatment in a use or in a method according to the invention is at least one week, at least one month, at least several months, at least one year, at least 2, 3, 4, 5, 6 years or more. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the mutation of the patient, the number of exon skipping molecules (i.e. dose), the formulation of said molecule. The frequency may be ranged between at least once in two weeks, or three weeks or four weeks or five weeks or a longer time period.

Dose ranges of an exon skipping molecule, preferably an oligonucleotide according to the invention are preferably designed on the basis of rising dose studies in clinical trials (in vivo use) for which rigorous protocol requirements exist. An exon skipping molecule or an oligonucleotide as defined herein may be used at a dose which is ranged from 0.1 and 20 mg/kg, preferably from 0.5 and 20 mg/kg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nm. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1\times10^9$-$1\times10^{17}$ virus particles per injection, more preferably from $1\times10^{10}$-$1\times10^{12}$ virus particles per injection.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule according to the invention, or a viral vector according to the invention, or a composition according to the invention for use according to the invention may be suitable for administration to a cell, tissue and/or an organ is vivo of individuals already affected or at risk of developing a CEP290 related disease or condition, and may be administered in vivo, ex vivo or in vitro. Said exon skipping molecule according to the invention, or a viral vector according to the invention, or a composition according to the invention may be directly or indirectly administrated to a cell, tissue and/or an organ in vivo of an individual already affected by or at risk of developing a CEP290 related disease or condition, and may be administered directly or indirectly in vivo, ex vivo or in vitro. As Leber congenital amaurosis has a pronounced phenotype in retina cells, it is preferred that said cells are retina cells, it is further preferred that said tissue is the retina and/or it is further preferred that said organ comprises or consists of the eye.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vive or in vitro.

The invention further provides a method for the treatment of a CEP290 related disease or condition requiring modulating splicing of CEP290 of an individual in need thereof, said method comprising contacting a cell, preferably a retina cell, of said individual with an exon skipping molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro. A preferred CEP290 related disease or condition is Leber congenital amaurosis.

Unless otherwise indicated each embodiment as described herein may be combined with another embodiment as described herein.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function. This experiment is presently ongoing.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO. 1 containing the nucleic acid sequence coding for the polypeptide should prevail.

All patent and literature references cited in the present specification are hereby incorporated by reference in their entirety.

BRIEF DESCRIPTION OF THE DRAWINGS

FIGS. 2a, 2b and 2c AON-based rescue of aberrant CEP290 splicing
A) RT-PCR analysis of CEP290 mRNA isolated from lymphoblastoid cells of one control individuals and two individuals affected with LCA, that were cultured in the absence or presence of a selected AON (AON-3) direct against the aberrant CEP290 exonin a final concentration of 1.0 µM. The upper band represents the aberrant CEP290 splice product, whereas the lower band represents the wild-type CEP290 splice product. M: 100-bp marker. MQ: negative water control.
B) Specificity of AON-based rescue. Similar to A), cells were transfected with AON-3, or a sense oligonucleotide directed to the same target site (SON-3). Left panel: RT-PCR reaction using primers located in exon 26 and exon 27. Right panel: RT-PCR reaction using primers located in exon 26 and exon 31.
C) Dose-dependent rescue of CEP290 mRNA splicing. Similar to A), cells were transfected with different concentrations of the selected AON, ranging from 0.01 to 1.0 µM.

SEQUENCES

Figure 1:
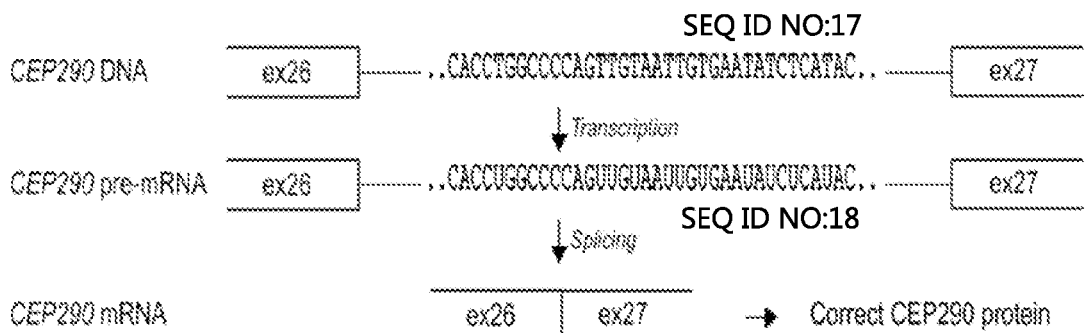
FIG. 1 CEP290 splicing and AON function
A) Normal CEP290 mRNA splicing of exons 26 and 27, resulting in wild-type CEP290 protein (figure discloses SEQ ID NOS 17-18, respectively, in order of appearance).
B) The most frequent LCA-causing mutation is an A-to-G transition (underlined and indicated with an asterisk) in intron 26 of CEP290. This mutation creates a splice donor site, which results in the inclusion of an aberrant exon to ~50% of the CEP290 mRNA and subsequent premature termination of the CEP290 protein (figure discloses SEQ ID NOS 19-20, respectively, in order of appearance).
C) Upon binding of sequence-specific AONs, factors involved in splicing will not recognize the aberrant splice donor site in intron 26, resulting in redirection of normal CEP290 splicing and synthesis of a correct CEP290 protein (figure discloses SEQ ID NOS 19, 21, and 20, respectively, in order of appearance).
Figure 1:
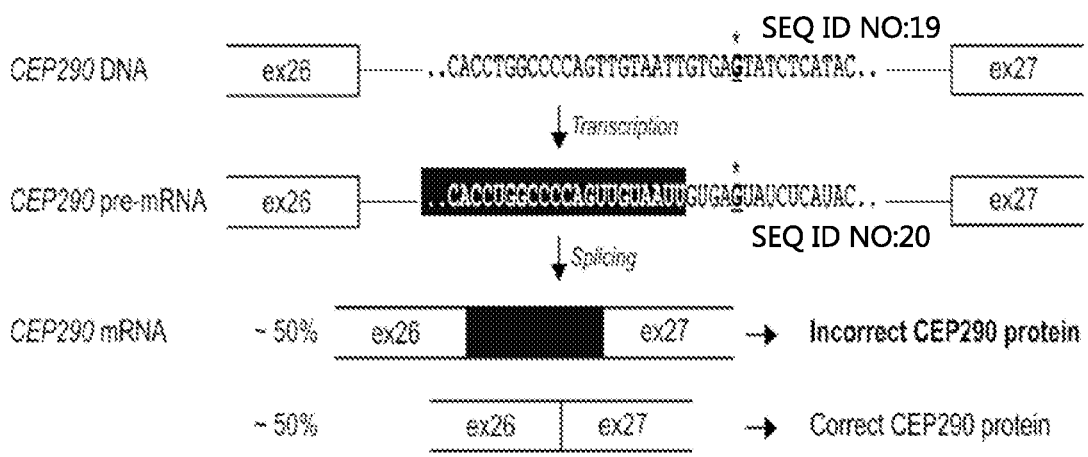
Figure 1:
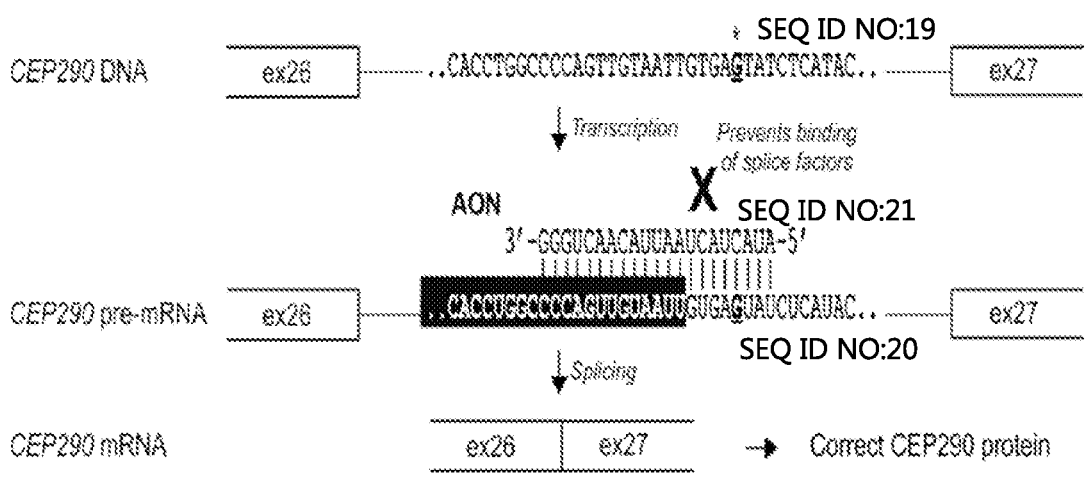

All sequences herein are depicted from 5'→3'

TABLE 1

Sequences as set forth in the Sequence Listing

| SEQ ID NO: | SEQ type | Description |
| --- | --- | --- |
| 1 | Genomic DNA | CEP290 |
| 2 | cDNA | CEP290 |
| 3 | PRT | CEP290 protein |
| 4 | DNA | 128 nucleotide aberrant CEP290 exon |
| 5 | PRT | CEP290 aberrant protein |
| 6 | Polynucleotide | 143 nucleotide motif |
| 7 | Polynucleotide | 42 nucleotide motif |
| 8 | Polynucleotide | 24 nucleotide motif |
| 9 | AON-1 | taatcccagcactttaggag |
| 10 | AON-2 | gggccaggtgcggtgg |
| 11 | AON-3 | aactggggccaggtgcg |
| 12 | AON-4 | tacaactggggccaggtg |
| 13 | AON-5 | actcacaattacaactgggg |
| 14 | SON-3 | cgcacctggccccagtt |
| 15 | PCR primer | tgctaagtacagggacatcttgc |
| 16 | PCR primer | agactccacttgttcttttaaggag |

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); Nucleic Acid Hybridization (Hames and Higgins, eds.).

Examples

Materials and Methods
Design Antisense Oligonucleotides

The 128-bp sequence of the aberrant CEP290 exon that is included into the mutant CEP290 mRNA was analyzed for the presence of exonic splice enhancer motifs using the ESE finder 3.0 program (rulai.cshl.edu/cgi-bin/tools/ESE3/esefinder.cgi?process=home). RNA antisense oligonucleotides were purchased from Eurogentec, and designed with a $T_m$ of 58° C., and modified with a 2'-O-methyl group at the sugar chain and a phosphothiorate backbone, and dissolved in phosphate buffered saline Cell Culture Human B-lymphoblasts cells of LCA patients homozygously carrying the intronic mutation in CEP290 were immortalized by transformation with the Eppstein-Barr virus, as described previously. (Wall F E, 1995). Cells were cultured in RPMI1640 medium (Gibco) containing 10% (v/v) fetal calf serum (Sigma), 1% 10 U/μl penicillin and 10 μg/μl streptomycin (Gibco), and 1% GlutaMAX (Gibco), at a density of $0.5\times10^6$ cells/ml. Cells were passaged twice a week.

Transfection of AONs

A day before transfection, $1.0\times10^6$ cells were seeded in each well of a 6-wells plate, in a total volume of 2 ml complete medium. Transfection mixtures were prepared by combining 2.5 μl AON in a desired concentration, or distilled water, 5 μl transfection reagent (ExGen in vitro 500, Fermentas) and 92.5 μl 150 mM NaCl, and incubated at room temperature for 10 minutes, before addition to the cells. Six hours after transfection, 8 ml of low-serum medium (complete medium with only 1% fetal calf serum) was added. Forty-eight hours after transfection, cells were collected and washed with 1×PBS, before directly proceeding to RNA isolation.

RNA Isolation and RT-PCR

Total RNA was isolated from transfected lymphoblastoid cells using the Nucleospin RNA II isolation kit (Machery Nagel), according to manufacturer's protocol. Subsequently, 1 μg of total RNA was used for cDNA synthesis using the iScript cDNA synthesis kit (Bio-Rad). Five percent of the cDNA was used for each PCR reaction. Part of the CEP290 cDNA was amplified under standard PCR conditions supplemented with 5% Q-solution (Qiagen), and using forward primer tgctaagtacagggacatcttgc (SEQ ID NO: 15) and reverse primer agactccacttgttcttttaaggag (SEQ ID NO: 16) that are located in exon 26 and exon 27 of the human CEP290 gene, respectively. PCR products were resolved on a 1.5% agarose gel. Bands presumably representing correctly and aberrantly spliced CEP290 were excised from the gel, purified using Nucleospin Extract II isolation kit and sequenced from both strands with the ABI PRISM Big Dye Terminator Cycle Sequencing V2.0 Ready Reaction kit and the ABI PRISM 3730 DNA analyzer (Applied Biosystems).

Introduction

Here, we describe the use of AONs to redirect normal splicing of CEP290 in patient-derived lymphoblast cells, and show a sequence-specific and dose-dependent decrease in levels of aberrantly spliced CEP290, thereby revealing the potential of AON-based therapy to treat CEP290-associated LCA.

Results

The intronic CEP290 mutation (c.2991+1655A>G) creates a cryptic splice donor site that results in the inclusion of an aberrant exon into the CEP290 mRNA (FIG. 1). Addition of AONs directed against the aberrant exon would prevent the insertion of this exon by preventing the binding of factors that are essential for splicing such as the U1- and U2snRNP complexes, and serine-arginine rich proteins, thereby restoring normal CEP290 splicing and protein synthesis (FIG. 1). AONs can target splice sites as well as exonic sequences, although in the particular case of the Duchenne muscular dystrophy DMD gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant CEP290 exon (128 nucleotides exonic sequence plus 15 nucleotides of intronic sequence on each side) was scrutinized for exonic splice enhancer binding motifs, using the ESE finder 3.0 program (Smith et al, 2006). At the 3'-end of the aberrant exon, two SC35-binding motifs were predicted (data not shown). Hence, the first AON was designed such that it encompassed these two motifs (designated AON-3, SEQ ID NO: 11), and being complementary to the (EP290 mRNA.

Figure 2A:
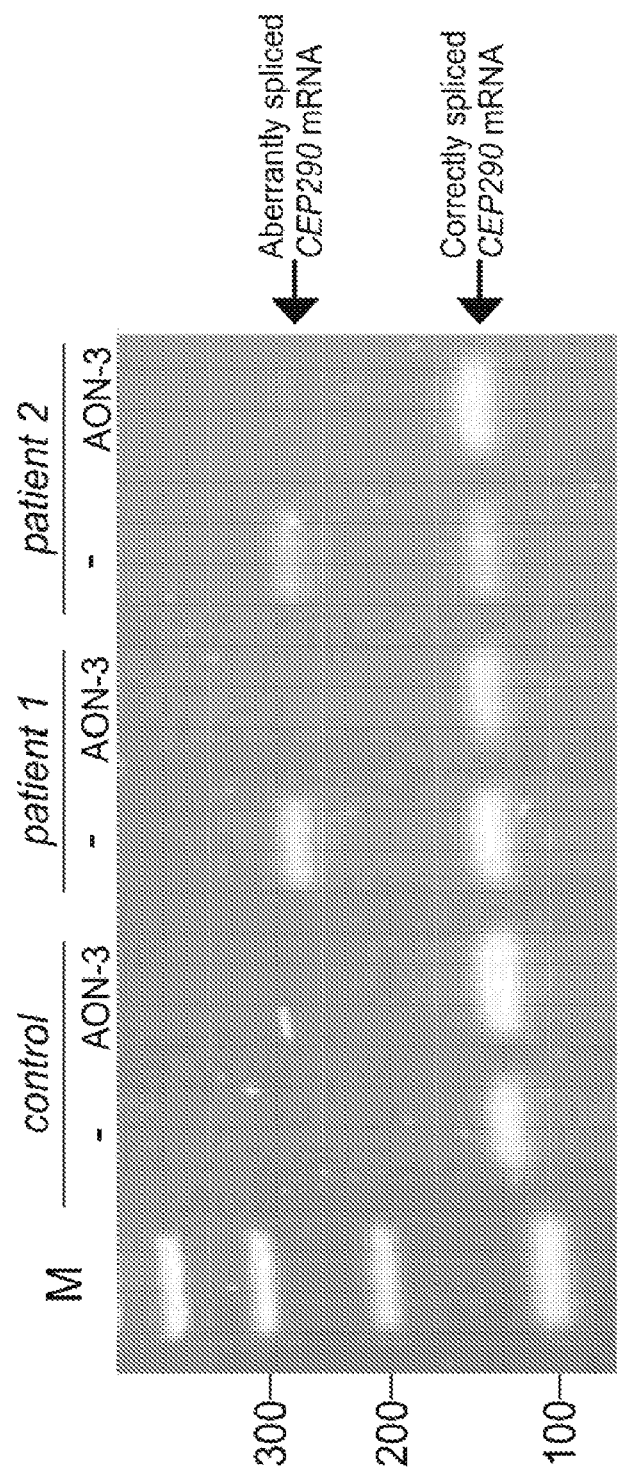
Figure 2B:
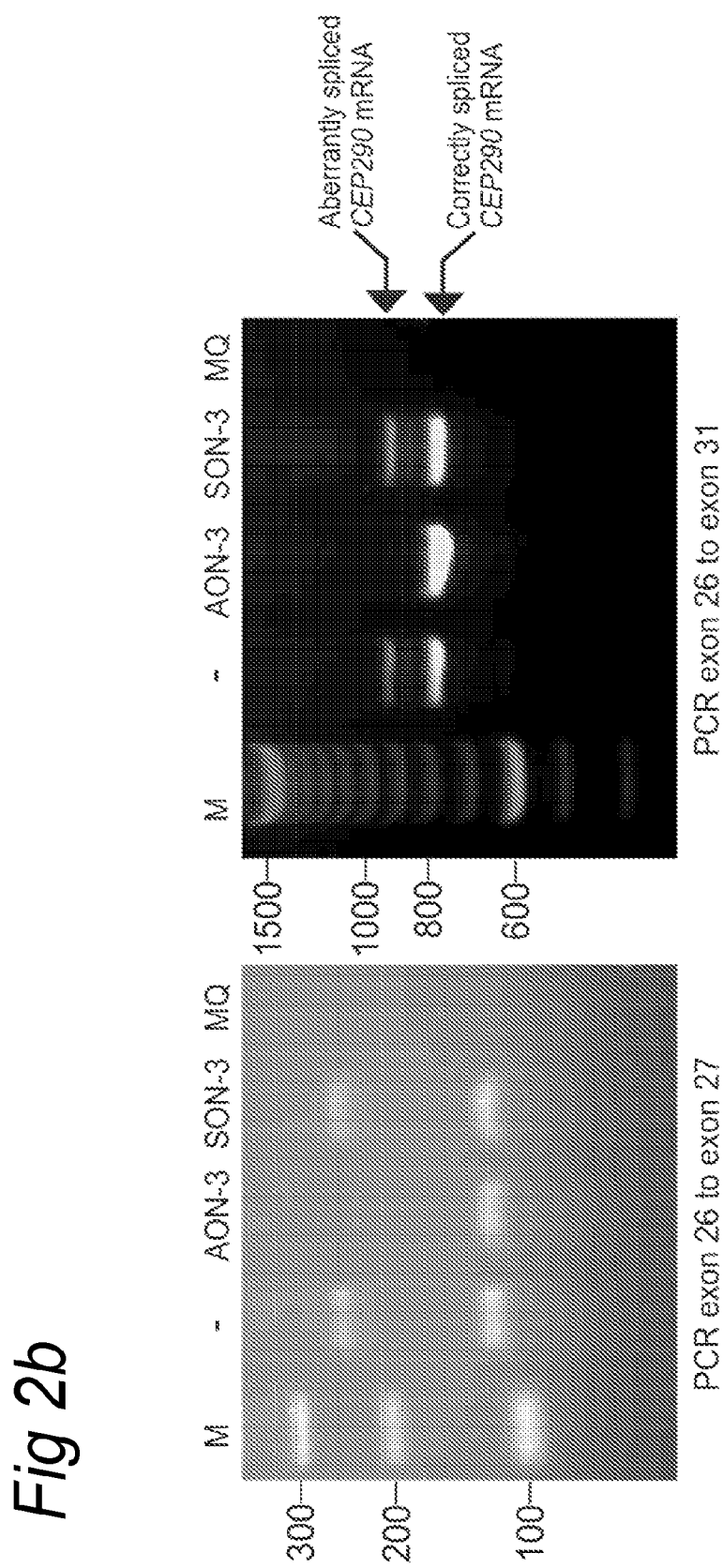

To determine whether AON-3 has exon-skipping potential in vitro, immortalized lymphoblastoid cells of two unrelated individuals with LCA homozygously carrying the intronic CEP290 founder mutation c.2991+1655A>G, as well as one control individual were cultured in the absence or presence of 1 μM AON-3. As expected, in the control individual, only a band representing correctly spliced CEP290 was observed, whereas in both affected individuals two products were present, one representing correctly spliced, and one representing aberrantly spliced CEP290 mRNA. Upon addition of AON-3, a strong decrease in aberrantly spliced CEP290 was noted, in both individuals with LCA (FIG. 2a). Next, the specificity of AON-3 was assessed by transfecting a sense oligonucleotide directed to the same target site (SON-3. SEQ ID NO: 14). RT-PCR analysis showed that in the cells transfected with SON-3, both the aberrantly spliced and the correctly spliced CEP290 mRNA molecules are still present (FIG. 2b, left panel), demonstrating the specificity of the antisense sequence. Using an additional pair of primers that amplifies larger products, similar results were obtained (FIG. 2b, right panel). Interestingly, the decrease in aberrantly spliced CEP290 appears to coincide with an increased intensity of the product representing correctly spliced CEP290 mRNA. These data indicate that the aberrant product is not degraded, but that the AON transfection truly induces exon skipping, resulting in the synthesis of more correctly spliced wild-type ('EP'290 mRNA. To determine the effective dose of AON-3, cells were transfected with various concentrations of AON-3, ranging from 0.01 to 1.0 μM. Even at the lowest concentration of 0.01 μM, a marked reduction in aberrantly spliced CEP290 was observed. The maximum amount of exon skipping was observed at 0.05 or 0.1 μM of AON, indicating that these concentrations are sufficient to convert almost all aberrantly spliced CEP290 (FIG. 2c).

Figure 3A:
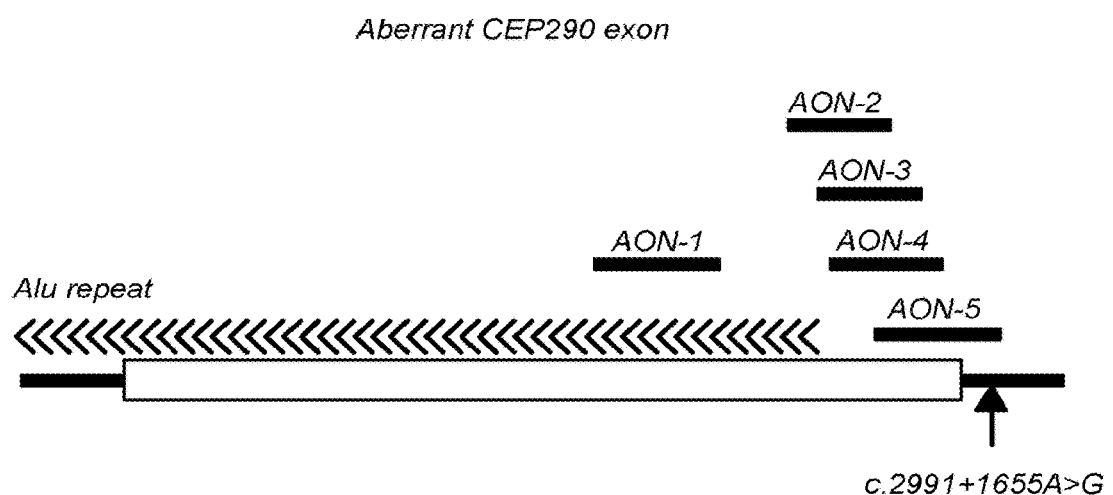
FIGS. 3a and 3b Sequence specificity in AON-based rescue of aberrant CEP290 splicing
A) Overview of the aberrant ('E'290 exon, and the relative positions of the AONs that were selected. The 5'-end of the aberrant exon is part of an Alu repeat.
B) RT-PCR analysis of CEP290 mRNA isolated from lymphoblastoid cells of an LCA patient that were cultured in the absence or presence of different AONs direct against the aberrant CEP290 exon (AON-1 to -5), or one sense oligonucleotide (SON-3). The AONs and SON were transfected in a final concentration of 0.1 µM. The upper band represents the aberrant CEP290 splice product, whereas the lower band represents the wild-type CEP290 splice product. M: 100-bp marker.
Figure 3B:
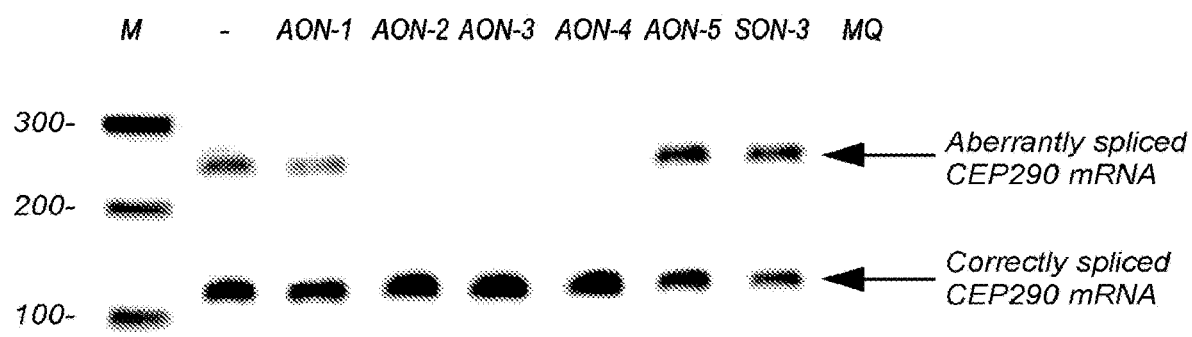

The effectiveness of AONs in splice modulation is thought to merely depend on the accessibility of the target mRNA molecule, and hence may differ tremendously between neighboring sequences. To determine whether this sequence specificity also applies for CEP290, several AONs were designed that target the aberrant CEP290 exon (Table 1). This exon consists of 128 base pairs, the majority of which are part of an Alu repeat, one of the most frequent repetitive elements in the human genome (Schmidt et al, 1982), covering the entire 5'-end of the aberrant exon (FIG. 3a). Hence, the majority of AONs were designed to be complementary to the 3'-end of the aberrant exon or the splice donor site (FIG. 3a). In total, five AONs were transfected at a final concentration of 0.1 μM, which was shown to be optimal for AON-3. Interestingly, besides AON-3, also AON-2 (SEQ ID NO: 10) and AON-4 (SEQ ID NO: 12) resulted in high levels of exon skipping. In contrast, AON-1 (SEQ ID NO: 9) that targets the Alu repeat region, and AON-5 (SEQ ID NO: 13) that is directed against the splice donor site, hardly showed any exon skipping potential (FIG. 3b). These data demonstrate the sequence specificity in AON-based exon skipping of CEP290 and highlight a small region of the aberrant CEP290 exon as a potential therapeutic target.

Discussion

In this study, we explored the therapeutic potential of AONs to correct a splice defect caused by an intronic mutation in CEP290. In immortalized lymphoblast cells of LCA patients homozygously carrying the intronic CEP290 mutation c.2991+1655A>G, transfection of some but not all AONs resulted in skipping of the aberrant exon, thereby almost fully restoring normal CEP290 splicing.

AONs have been the focus of therapeutic research for over a decade, for the treatment of a variety of genetic diseases (Hammond et al, 2011). These strategies include the use of AONs to block the recognition of aberrant splice sites, to alter the ratio between two naturally occurring splice isoforms, to induce skipping of exons that contain protein-truncating mutations, or to induce the skipping of exons in order to restore the reading-frame of a gene that is disrupted by a genomic deletion, allowing the synthesis of a (partially) functional protein (Hammond et al, 2011). The latter approach is already being applied in phase I/II clinical trials for the treatment of patients with Duchenne muscular dystrophy, with promising results (Kinali et al, 2009; van Deutekom et al, 2007).

The intronic CEP290 mutation is an ideal target for AON-based therapy, since this mutation results in the inclusion of an aberrant exon in the CEP290 mRNA which is normally not transcribed. Inducing skipping of this aberrant exon by AONs fully restores the normal CEP290 mRNA, allowing normal levels of CEP290 protein to be synthesized. A second major advantage is that although this AON-approach is a mutation-specific therapeutic strategy, the intronic CEP290 mutation is by far the most frequent LCA-causing mutation.[4] Based on the estimated prevalence of LCA (1:50,000), and the observed frequency of the intronic CEP290 mutation in Northern-Europe (26%) (Coppieters et al, 2010) and the U.S. (10%) (Stone, 2007), at least one thousand and, depending on the frequency of the mutation in other populations, perhaps many more individuals worldwide have LCA due to this mutation. Finally, although the LCA phenotype associated with CEP290 mutations is severe, it appears that the photoreceptor integrity, especially in the macula, as well as the anatomical structure of the visual connections to the brain, are relatively intact in LCA patients with CEP290 mutations, which would allow a window of opportunity for therapeutic intervention (Cideciyan et al, 2007).

The study described here provides a proof-of-principle of AON-based therapy for CEP290-associated LCA in vitro, using immortalized patient lymphoblast cells. In order to determine the true therapeutic potential of this method for treating LCA, additional studies are needed that include the development of therapeutic vectors, and assessment of efficacy and safety in animal models. Although naked AONs, or conjugated to cell-penetrating peptides, can be delivered to the retina by intraocular injections, the limited stability of the AONs would require multiple injections in each individual. In contrast, by using viral vectors, a single subretinal injection would suffice to allow a long-term expression of the therapeutic construct. Previously, others have used recombinant adeno-associated viral (rAAV) vectors carrying U1- or modified U7snRNA constructs to efficiently deliver AON sequences, in the mdx mouse model for DMD, or in DMD patient myoblasts, respectively (Geib et al, 2009; Goyenhalle et al, 2004) In line with this, AONs targeting the aberrant exon of CEP290 could be cloned within such constructs, and delivered to the retina by subretinal injections of rAAV-5 or -8 serotypes that efficiently transduce photoreceptor cells where the endogenous CEP290 gene is expressed (Alloca et al, 2007; Lebherz et al, 2008). Using rAAV-2 vectors, no long-lasting immune response was evoked upon subretinal injections of these vectors in patients with RPE65 mutations (Simonella et al, 2009), and also for rAAV-5 and rAAV-8, immune responses appear to be absent or limited, at least in animal models (Li et al, 2009; Vandenberghe et al, 2011). One final safety aspect concerns the specificity of the sequence that is used to block the splicing of the aberrant CEP290 exon. As stated before, the majority of this exon is part of an Alu repeat, and AONs directed against this repeat will likely bind at multiple sites in the human genome, increasing the chance to induce off-target effects. The AONs that were shown to be effective in this study do not fully target the Alu repeat sequence, but are also not completely unique in the human genome. However, when blasting against the EST database, no exact hits are found, indicating that at the level of expressed genes, these sequences are unlikely to induce off-target effects and deregulate normal splicing of other genes. To further study the efficacy and safety of AON-based therapy for CEP290-associated LCA in vivo, we are currently generating a transgenic knock-in mouse model that carries part of the human CEP290 gene (exon 26 to exon 27, with and without the intronic mutation) which is exchanged with its mouse counterpart. Compared to gene augmentation therapy, AON-based therapy has a number of advantages. First, in gene augmentation therapy, a ubiquitous or tissue-specific promoter is used to drive expression of the wild-type cDNA encoding the protein that is mutated in a certain patient. For instance in one clinical trial for RPE65 gene therapy, the chicken beta-actin promoter was used (Maguire et al, 2008). Using these but also fragments of the endogenous promoters, it is difficult to control the levels of expression of the therapeutic gene. In some cases, like for the RPE65 protein that has an enzymatic function, expression levels beyond those of the endogenous gene might not be harmful to the retina. For other genes however, including those that encode structural proteins like CEP290, tightly-regulated expression levels might be crucial for cell survival, and overexpression of the therapeutic protein might exert toxic effects. Using AONs, the therapeutic intervention occurs at the pre-mRNA level, and hence does not interfere with the endogenous expression levels of the target gene. A second issue is the use of the viral vector. Of a variety of different recombinant viral vectors, rAAVs are considered to be most suitable for treating retinal dystrophies, because of their relatively high transduction efficiency of retinal cells, and their limited immunogenicity. The major drawback of rAAVs however is their limited cargo size of 4.8 kb. Again, for some genes like RPE65, this is not a problem. For many other retinal genes however, like CEP290 (with an open reading frame of 7.4 kb), but also ABCA4 and USH2A, the size of their full-length cDNAs exceeds the cargo size of the currently available pool of rAAVs. One way to overcome this problem is to express cDNAs that express only partial proteins with residual activity, as has been suggested for CEP290 by expressing the N-terminal region of CEP290 in a zebrafish model (Baye et al, 2011). Other viral vectors, like lentivirus or adenoviruses have a higher cargo capacity that rAAVs (~8 kb), but are less efficient in transducing retinal cells, and adenoviruses have a higher immunogenic potential (den Hollander et al, 2010). For AON-based therapy, the size limitations of AAV are not a problem, since the small size of the AONs and the accompanying constructs easily fit within the available AAVs.

In conclusion, this study shows that administration of AONs to cultured patient cells almost fully corrects a splice defect that is caused by a frequent intronic mutation in CEP290 that causes LCA. These data warrant further research to determine the therapeutic potential of AON-based therapy for CEP290-associated LCA, in order to delay or cease the progression of this devastating blinding disease.

REFERENCE LIST

1. Leber, T. (1869). Uber Retinitis Pigmentosa und angeborene Amaurose. von Graefe's Archives Ophthalmology 15, 1-25.
2. Koenekoop, R. K., Lopez, I, den Hollander, A. I, Allikmets, R., and Cremers, F. P. (2007). Genetic testing for retinal dystrophies and dysfunctions: benefits, dilemmas and solutions. Clin Experiment Ophthalmol 35, 473-485.
3. Stone, E. M. (2007). Leber congenital amaurosis—a model for efficient genetic testing of heterogeneous disorders: LXIV Edward Jackson Memorial Lecture. Am J Ophthalmol 144, 791-811.
4. den Hollander, A. I., Roepman, R., Koenekoop, R. K., and Cremers, F. P. M. (2008). Leber congenital amaurosis: genes, proteins and disease mechanisms. Prog Retin Eye Res 27, 391-419.
5. Estrada-Cuzcano, A., Koenekoop, R. K., Coppieters, F., Kohl, S., Lopez, I., Collin, R. W. J., De Baere, E. B., Roeleveld, D., Marek, J., Bernd, A. et al (2011). IQCB1 mutations in patients with leber congenital amaurosis. Invest Ophthalmol Vis Sci 52, 834-839.
6. den Hollander, A. I., Koenekoop, R. K., Yzer, S., Lopez, I., Arends, M. L., Voesenek, K. E., Zonneveld, M. N., Strom, T. M., Meitinger, T., Brunner, H. G. et al (2006). Mutations in the CEP290 (NPHP6) gene are a frequent cause of Leber congenital amaurosis. Am J Hum Genet 79, 556-561.
7. Perrault, I., Delphin, N, Hanein, S, Gerber, S., Dutler, J. L., Roche, O., foort-Dhellemmes, S, Dollfus, H, Fazzi, E, Munnich, A et al (2007). Spectrum of NPHP6/CEP290 mutations in Leber congenital amaurosis and delineation of the associated phenotype. Hum Mutat 28, 416.
8. Baala, L., Audollent, S., Martinovic, J., Ozilou, C., Babron, M. C., Sivanandamoorthy, S., Saunier, S., Salomon, R., Gonzales, M., Rattenberry, E. et al (2007). Pleiotropic effects of CEP290 (NPHP6) mutations extend to Meckel syndrome. Am J Hum Genet 81, 170-179.
9. Frank, V., den Hollander, A. I., Bruchle, N. O., Zonneveld, M. N., Nurnberg, G., Becker, C., Du, B. G., Kendziorra, H., Roosing, S., Senderek, J. et al (2008). Mutations of the (CEP290 gene encoding a centrosomal protein cause Meckel-Gruber syndrome. Hum Mutat 29, 45-52.
10. Helou, J., Otto, E. A., Attanasio, M., Allen, S. J., Parisi, M. A., Glass, I., Utsch, B., Hashmi, S., Fazzi, E., Omran, H. et al (2007). Mutation analysis of NPHP6/CEP290 in patients with Joubert syndrome and Senior-Loken syndrome. J Med Genet 44, 657-663.
11. Valente, E. M., Silhavy, J. L., Brancati, F, Barrano, G., Krishnaswami, S. R., Castori, M., Lancaster, M. A., Boltshauser, E., Boccone, L., Al-Gazali, L. et al (2006). Mutations in CEP290, which encodes a centrosomal protein, cause pleiotropic forms of Joubert syndrome. Nat Genet 38, 623-625.
12. Coppieters, F., Casteels, I., Meire, F., De Jaegere S., Hooghe, S., van Regemorter N., Van Esch H., Matuleviciene, A., Nunes, L., Meersschaut, V. et al (2010). Genetic screening of LCA in Belgium: predominance of CEP290 and identification of potential modifier alleles in AH11 of CEP290-related phenotypes. Hum Mutat 31, E1709-E1766.
13. Littink, K. W., Pott, J. W., Collin, R. W. J., Kroes, H. Y., Verheij, J. B., Blokland, E. A., de Castro Miro M., Hoyng, C. B., Klaver, C. C., Koenekoop, R. K. et al (2010). A novel nonsense mutation in CEP290 induces exon skipping and leads to a relatively mild retinal phenotype. Invest Ophthalmol Vis Sci 51, 3646-3652.
14. Bainbridge, J. W., Smith, A. J., Barker, S. S., Robbie, S., Henderson, R., Balaggan, K., Viswanathan, A., Holder, G. E., Stockman, A., Tyler, N. et al (2008). Effect of gene therapy on visual function in Leber's congenital amaurosis N Engl J Med 358, 2231-2239.
15. Cideciyan, A. V, Aleman, T. S., Boye, S. L., Schwartz, S B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.
16. Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada-Mutations by Ocular Subretinal Injection of Adeno-Associated Virus Gene Vector: Short-Term Results. Hum Gene Ther
17. Maguire, A. M., Simonelli, F., Pierce, E. A., Pugh, E. N., Jr., Mingozzi, F., Bennicelli, J., Banfi, S., Marshall, K. A., Testa, F., Surace, E. M. et al (2008). Safety and efficacy of gene transfer for Leber's congenital amaurosis. N Engl J Med 358, 2240-2248.
18. Maguire, A. M., High, K. A., Auricchio, A., Wright, J. F., Pierce, E. A., Testa, F., Mingozzi, F., Bennicelli, J. L., Ying, G. S., Rossi, S. et al (2009). Age-dependent effects of RPE65 gene therapy for Leber's congenital amaurosis: a phase 1 dose-escalation trial. Lancet 374, 1597-1605.
19. den Hollander, A. I., Black, A., Bennett, J., and Cremers, F. P. M. (2010). Lighting a candle in the dark: advances in genetics and gene therapy of recessive retinal dystrophies. J Clin Invest 120, 3042-3053.
20. Aartsma-Rus, A., Houlleberghs, H., van Deutekom, J. C., van Ommen, G. J., and 't Hoen, P. A. (2010). Exonic sequences provide better targets for antisense oligonucleotides than splice site sequences in the modulation of Duchenne muscular dystrophy splicing. Oligonucleotides 20, 69-77.
21. Aartsma-Rus, A., van, V. L., Hirschi, M., Janson, A. A., Heemskerk, H., de Winter, C. L., de, K. S., van Deutekom, J. C., 't Hoen, P. A., and van Ommen, G. J. (2008). Guidelines for Antisense Oligonucleotide Design and Insight Into Splice-modulating Mechanisms. Mol Ther
22. Smith, P. J., Zhang, C., Wang, J., Chew, S. L., Zhang, M. Q., and Krainer, A. R. (2006). An increased specificity score matrix for the prediction of SF2/ASF-specific exonic splicing enhancers. Hum Mol Genet 15, 2490-2508.
23. Schmid, C. W. and Jelinek, W. R. (1982). The Alu family of dispersed repetitive sequences. Science 216, 1065-1070.
24. Hammond, S M and Wood, M. J. (2011). Genetic therapies for RNA mis-splicing diseases. Trends Genet 27, 196-205.
25. Kinali, M., rechavala-Gomeza, V., Feng, L., Cirak, S., Hunt, D., Adkin, C., Guglieri, M., Ashton, E., Abbs, S., Nihoyannopoulos, P. et al (2009). Local restoration of 26. van Deutekom, J. C., Janson, A. A., Ginjaar, I. B., Frankhuizen, W. S., Aartsma-Rus, A., Bremmer-Bout, M., Den Dunnen, J. T., Koop, K., van der Kooi, A. J., Goemans, N. M. et al (2007). Local dystrophin restoration with antisense oligonucleotide PRO051. N Engl J Med 357, 2677-2686.
27. Coppieters, F., Lefever, S., Leroy, B. P., and De, B. E. (2010). CEP290, a gene with many faces: mutation overview and presentation of CEP290 base. Hum Mutat 31, 1097-1108.
28. Cideciyan, A. V., Aleman, T. S., Jacobson, S. G., Khanna, H., Sumaroka, A., Aguirre, G. K., Schwartz, S. B., Windsor, E. A., He, S., Chang, B. et al (2007). Centrosomal-ciliary gene CEP290/NPHP6 mutations result in blindness with unexpected sparing of photoreceptors and visual brain: implications for therapy of Leber congenital amaurosis. Hum Mutat 28, 1074-1083.
29. Geib, T. and Hertel, K. J. (2009). Restoration of full-length SMN promoted by adenoviral vectors expressing RNA antisense oligonucleotides embedded in U7 snRNAs. PLoS One 4, e8204.
30. Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.
31. Allocca, M., Mussolino, C., Garcia-Hoyos, M., Sanges, D., Iodice, C., Petrillo, M., Vandenberghe, L. H., Wilson, J. M., Marigo, V., Surace, E. M. et al (2007). Novel adeno-associated virus serotypes efficiently transduce murine photoreceptors. J Virol 81, 11372-11380.
32. Lebherz, C., Maguire, A., Tang, W., Bennett, J., and Wilson, J. M. (2008). Novel AAV serotypes for improved ocular gene transfer. J Gene Med 10, 375-382.
33. Simonelli, F., Maguire, A. M., Testa, F., Pierce, E. A., Mingozzi, F., Bennicelli, J. L, Rossi, S., Marshall, K., Banfi, S., Surace, E. M et al (2009) Gene Therapy for Leber's Congenital Amaurosis is Safe and Effective Through 1.5 Years After Vector Administration. Mol Ther
34. Li, W., Kong, F., Li, X., Dai, X., Liu, X., Zheng, Q., Wu, R., Zhou, X., Lu, F., Chang, B. et al (2009). Gene therapy following subretinal AAV5 vector delivery is not affected by a previous intravitreal AAV5 vector administration in the partner eye. Mol Vis 15, 267-275.
35. Vandenberghe, L. H., Bell, P., Maguire, A. M., Cearley, C. N., Xiao, R., Calcedo, R., Wang, L., Castle, M. J., Maguire, A. C., Grant, R. et al (2011). Dosage Thresholds for AAV2 and AAV8 Photoreceptor Gene Therapy in Monkey. Sci Transl Med 3, 88ra54.
36. Baye, L. M., Patrinostro, X., Swaminathan, S., Beck, J. S., Zhang, Y., Stone, E. M., Sheffield, V. C., and Slusarski, D. C. (2011). The N-terminal region of centrosomal protein 290 (CEP290) restores vision in a zebrafish model of human blindness. Hum Mol Genet 20, 1467-1477.
37. Dorn and Kippenberger, Curr Opin Mol Ther 2008 10(1) 10-20
38. Nielsen, et al. (1991) Science 254, 1497-1500
39. Govindaraju and Kumar (2005) Chem. Commun, 495-497
40. Egholm et al (1993) Nature 365, 566-568
41. Morita et al. 2001. Nucleic Acid Res Supplement No. 1: 241-242
42. Gorman L, et al, Stable alteration of pre-mRNA splicing patterns by modified U7 small nuclear RNAs. Proc Natl Acad Sci USA 1998; 95(9):4929-34
43. Suter D, et al, Double-target antisense U7 snRNAs promote efficient skipping of an aberrant exon in three human beta-thalassemic mutations. Hum Mol Genet 1999; 8(13):2415-23
44. Remington: The Science and Practice of Pharmacy, 20th Edition. Baltimore, Md.: Lippincott Williams & Wilkins, 2000

The invention claimed is:

1. A method for treating Leber congenital amaurosis (LCA) caused by the mutation CEP290 (c.2991+1655A>G), comprising administering to the eye in a subject in need thereof an exon skipping antisense oligonucleotide having a length from 8 to 128 nucleotides and having 90% to 100% complementarity to a sequence within SEQ ID NO:6, wherein said antisense oligonucleotide comprises one or more modifications to increase nuclease resistance.

2. The method according to claim 1, wherein said administration is intraocular injection of said antisense oligonucleotide.

3. The method according to claim 2, wherein the antisense oligonucleotide is for administration at a dose in an amount ranging from 0.1 to 20 mg/kg.

4. The method according to claim 1, wherein said antisense oligonucleotide has a length from 12 to 30 nucleotides.

5. The method according to claim 1, wherein said antisense oligonucleotide comprises or consists of a sequence selected from the group consisting of SEQ ID NO: 10, SEQ ID NO: 11, and SEQ ID NO: 12.

6. The method according to claim 1, wherein said one or more modifications to increase nuclease resistance is a substitution in one of the non-bridging oxygens in a phosphodiester linkage.

7. The method according to claim 6, wherein said antisense oligonucleotide comprises one or more phosphorothioate linkages.

8. The method according to claim 1, wherein said antisense oligonucleotide comprises one or more sugar moieties mono- or di-substituted at the 2', 3', and/or 5' position.

9. The method according to claim 8, wherein said one or more sugar moieties is monosubstituted at the 2' position with an alkyl group or an O-alkyl group.

10. The method according to claim 9, wherein said monosubstituted sugar moiety is a ribose.

11. The method according to claim 10, wherein said modified ribose is a 2'-O-alkyl modified ribose, a 2'-O-methyl modified ribose, a 2'-O-ethyl modified ribose, a 2'-O-propyl modified ribose, and/or substituted derivatives thereof.

12. The method according to claim 11, wherein said modified ribose is a 2'-O-methoxyethyl modified ribose.

13. The method according to claim 11, wherein said substituted derivatives are halogenated derivatives.

\* \* \* \* \*

UNITED STATES PATENT AND TRADEMARK OFFICE
CERTIFICATE OF CORRECTION

| | |
|---|---|
| PATENT NO. | : 11,279,933 B2 |
| APPLICATION NO. | : 16/842157 |
| DATED | : March 22, 2022 |
| INVENTOR(S) | : Robert Wilhelmus Johanna Collin et al. |

It is certified that error appears in the above-identified patent and that said Letters Patent is hereby corrected as shown below:

In the Specification

Column 1, Line 19, delete "IO filed" and insert -- filed --

Signed and Sealed this
Fourteenth Day of March, 2023

*Katherine Kelly Vidal*

Katherine Kelly Vidal
*Director of the United States Patent and Trademark Office*